US011015210B2

(12) United States Patent
Faust et al.

(10) Patent No.: US 11,015,210 B2
(45) Date of Patent: May 25, 2021

(54) CONSTRUCTS AND METHODS FOR DELIVERING MOLECULES VIA VIRAL VECTORS WITH BLUNTED INNATE IMMUNE RESPONSES

(71) Applicants: Joseph E. Rabinowitz, Elkins Park, PA (US); The Trustees of the University of Pennsylvania, Philadelphia, PA (US)

(72) Inventors: Susan M. Faust, Philadelphia, PA (US); Joseph E. Rabinowitz, Elkins Park, PA (US); James M. Wilson, Glen Mills, PA (US)

( * ) Notice: Subject to any disclaimer, the term of this patent is extended or adjusted under 35 U.S.C. 154(b) by 0 days.

(21) Appl. No.: 15/099,651

(22) Filed: Apr. 15, 2016

(65) Prior Publication Data

US 2016/0222414 A1 Aug. 4, 2016

Related U.S. Application Data

(63) Continuation of application No. 14/211,666, filed on Mar. 14, 2014, now abandoned.

(60) Provisional application No. 61/785,368, filed on Mar. 14, 2013.

(51) Int. Cl.
*C12N 15/86* (2006.01)
*C07H 21/04* (2006.01)
*A61K 48/00* (2006.01)
*C12N 7/00* (2006.01)

(52) U.S. Cl.
CPC .......... *C12N 15/86* (2013.01); *A61K 48/0058* (2013.01); *A61K 48/0075* (2013.01); *A61K 48/0091* (2013.01); *C12N 7/00* (2013.01); *C07H 21/04* (2013.01); *C12N 2750/14141* (2013.01); *C12N 2750/14142* (2013.01); *C12N 2750/14143* (2013.01); *C12N 2800/24* (2013.01)

(58) Field of Classification Search
CPC .. C12N 15/86; C12N 15/8645; C12N 15/117; C12N 2750/14143; C07H 21/04
USPC ............................ 435/320.1; 536/23.1, 24.1
See application file for complete search history.

(56) References Cited

U.S. PATENT DOCUMENTS

2004/0053870 A1 3/2004 Yew et al.
2011/0070241 A1 3/2011 Yang et al.
2012/0009222 A1 1/2012 Yew et al.

FOREIGN PATENT DOCUMENTS

WO WO 2007/036233 A2 * 4/2007
WO WO 2011/126808 10/2011

OTHER PUBLICATIONS

Yang, Yiping, 2011, 20110070241 A1.*
Faust et al., Oct. 2012, Human Gene Therapy, vol. 23, No. 10, pp. A115.
Yew, Nelson, 2007, US 20070003521 A1.
Hyde et al., 2008, Nature Biotechnology, vol. 26, No. 5, p. 549-551.
Garcia et al., 2014, US 20140107186 A1, effective filing date, Mar. 11, 2011.
Nam et al, "Structure of adeno-associated virus serotype 8, a gene therapy vector", J Virol., vol. 81(22) pp. 12260-12271 (Nov. 2007).
Xie et al, "The atomic structure of adeno-associated virus (AAV-2), a vector for human gene therapy", PNAS, vol. 99(16) pp. 10405-10410 (Aug. 2002).
Govindasamy et al, "Structurally mapping the diverse phenotype of adeno-associated virus serotype 4", J. Virol., vol. 80(23) pp. 11556-11570 (Dec. 2006).
Kotin et al, "Site-specific integration by adeno-associated virus" PNAS, vol. 87(6) pp. 2211-2215 (Mar. 1990).
Zhu et al, "The TLR9-MyD88 pathway is critical for adaptive immune responses to adeno-associated virus gene therapy vectors in mice", J. Clin. Invest., vol. 119(8) pp. 2388-2398 (Aug. 2009).
Rogers et al, "Innate Immune Responses to AAV Vectors", Front Microbiol., vol. 2 (Article 194) pp. 1-10 (Sep. 2011).
Satya et al, "A pattern matching algorithm for codon optimization and CpG motif-engineering in DNA expression vectors", IEEE, Proceedings of the 2003 IEEE Bioinformatics Conference. CSB2003, pp. 294-305 (Aug. 2003).
Faust et al, "CpG-depleted adeno-associated virus vectors evade immune detection" J. Clin. Invest. vol. 123(7) pp. 2994-3001 (Jun. 2013).
Faust et al, "Escaping Immune Activation through the Use of CpG-Depleted AAV Vectors" Simultaneous Oral Abstract Sessions: Immunologic & Host Responses in Gene & Cell Therapy, Abstract 108 (May 16, 2013) E-published Apr. 2013.
Breous et al., *Gastroenterology*, 141: 348-357 (2011).
Hosel et al., *Hepatology*, 55(1): 287-297 (2012).
Karman et al., *PLOS One*, 7(4): 1-11 e34684 (2012).

(Continued)

*Primary Examiner* — Shin Lin Chen
(74) *Attorney, Agent, or Firm* — Neal, Gerber & Eisenberg LLP

(57) ABSTRACT

A CpG-modified recombinant adeno-associated viral (AAV) vector is described. The vector carries a nucleic acid molecule comprising AAV inverted terminal repeat (ITR) sequences and an exogenous gene sequence under the control of regulatory sequences which control expression of the gene product, in which the nucleic acid sequences carried by the vector are modified to significantly reduce CpG dinucleotides such that an immune response to the vector is reduced as compared to the unmodified AAV vector. Also provided are methods and regimens for delivering transgenes using these AAV viral vectors, in which the innate immune response to the vector and/or transgene is significantly modulated.

37 Claims, 49 Drawing Sheets

Specification includes a Sequence Listing.

(56) References Cited

OTHER PUBLICATIONS

Mays et al., *The Journal of Immunology*, 182: 6051-6060 (2009).
Mingozzi et al., *Current Gene Therapy*, 11: 321-330 (2011).
Mingozzi et al., *The American Society of Gene & Cell Therapy*, 20(7): 1410-1416 (2012).
Nayak et al., *Gene Therapy*, 17: 295-304 (2010).
Wang et al., *Frontiers in Microbiology*, 2(201): 1-6 (2011).
Wang et al., *Journal of Molecular and Cellular Cardiology*, 50: 793-802 (2011).
Wright, *Molecular Therapy*, 28(3): 1-3 (2020).
Zhu et al., *The Journal of Clinical Investigation*, 119(8): 2388-2398 (2009).
George, Lindsey, *Blood*, BLD-2020-009285-C (2020).
Konkle et al., *Blood*, BLD-2019-004625R1 (2020).
Wright, J., *Molecular Therapy*, 28(3):1-3 (2020).

* cited by examiner

FIG. 11A

```
        LacZ alignment
  1                                                    50
CpG+LacZ     (1) ATGACCATGATTACGGATTCACTGGCCGTCGTTTTACAACGTCGTGACTG
CpG-LacZ     (1) ----------------ATGGAC--CCTGTTGTGCTGCAAAGGAGAGACTG
Consensus    (1)                 AT  AC   C GT GT  T CAA G  G GACTG
                 51                                             100
CpG+LacZ    (51) GGAAAACCCTGGCGTTACCCAACTTAATCGCCTTGCAGCACATCCCCCTT
CpG-LacZ    (33) GGAGAACCCTGGAGTGACCCAGCTCAACAGACTGGCTGCCCACCCTCCCT
Consensus   (51) GGA AACCCTGG GT ACCCA CT AA  G CT GC GC CA CC CC T
                 101                                            150
CpG+LacZ   (101) TCGCCAGCTGGCGTAATAGCGAAGAGGCCCGCACCGATCGCCCTTCCCAA
CpG-LacZ    (83) TTGCCTCTTGGAGGAACTCTGAGGAAGCCAGGACAGACAGGCCCAGCCAG
Consensus  (101) T GCC   TGG G AA    GA GA GCC G AC GA  G CC   CCA
                 151                                            200
CpG+LacZ   (151) CAGTTGCGCAGCCTGAATGGCGAATGGCGCTTTGCCTGGTTTCCGGCACC
CpG-LacZ   (133) CAGCTCAGGTCTCTCAATGGAGAGTGGAGGTTTGCCTGGTTCCCTGCCCC
Consensus  (151) CAG T  G    CT AATGG GA TGG G TTTGCCTGGTT CC GC CC
                 201                                            250
CpG+LacZ   (201) AGAAGCGGTGCCGGAAAGCTGGCTGGAGTGCGATCTTCCTGAGGCCGATA
CpG-LacZ   (183) TGAAGCTGTGCCTGAGTCTTGGCTGGAGTGTGACCTCCCAGAGGCTGACA
Consensus  (201)  GAAGC GTGCC GA    TGGCTGGAGTG GA CT CC GAGGC GA A
                 251                                            300
CpG+LacZ   (251) CTGTCGTCGTCCCCTCAAACTGGCAGATGCACGGTTACGATGCGCCCATC
CpG-LacZ   (233) CTGTTGTGGTGCCCAGCAACTGGCAGATGCATGGCTATGATGCCCCCATC
Consensus  (251) CTGT GT GT CCC   AACTGGCAGATGCA GG TA GATGC CCCATC
                 301                                            350
CpG+LacZ   (301) TACACCAACGTGACCTATCCCATTACGGTCAATCCGCCGTTTGTTCCCAC
CpG-LacZ   (283) TACACCAATGTCACCTACCCCATCACTGTGAACCCCCCTTTTGTGCCCAC
Consensus  (301) TACACCAA GT ACCTA CCCAT AC GT AA CC CC TTTGT CCCAC
                 351                                            400
CpG+LacZ   (351) GGAGAATCCGACGGGTTGTTACTCGCTCACATTTAATGTTGATGAAAGCT
CpG-LacZ   (333) TGAGAACCCCACTGGCTGCTACAGCCTGACCTTCAATGTTGATGAGAGCT
Consensus  (351)  GAGAA CC AC GG TG TAC   CT AC TT AATGTTGATGA AGCT
                 401                                            450
CpG+LacZ   (401) GGCTACAGGAAGGCCAGACGCGAATTATTTTTGATGGCGTTAACTCGGCG
CpG-LacZ   (383) GGCTGCAAGAAGGCCAGACCAGGATCATCTTTGATGGAGTCAACTCTGCC
Consensus  (401) GGCT CA GAAGGCCAGAC  G AT AT TTTGATGG GT AACTC GC
                 451                                            500
CpG+LacZ   (451) TTTCATCTGTGGTGCAACGGGCGCTGGGTCGGTTACGGCCAGGACAGTCG
CpG-LacZ   (433) TTCCACCTCTGGTGCAATGGCAGGTGGGTGGGCTATGGCCAAGACAGCAG
Consensus  (451) TT CA CT TGGTGCAA GG  G TGGGT GG TA GGCCA GACAG  G
                 501                                            550
CpG+LacZ   (501) TTTGCCGTCTGAATTTGACCTGAGCGCATTTTTACGCGCCGGAGAAAACC
CpG-LacZ   (483) GCTGCCCTCTGAGTTTGACCTCTCTGCCTTCCTCAGAGCTGGAGAGAACA
Consensus  (501)   TGCC TCTGA TTTGACCT    GC TT  T  G GC GGAGA AAC
                 551                                            600
CpG+LacZ   (551) GCCTCGCGGTGATGGTGCTGCGCTGGAGTGACGGCAGTTATCTGGAAGAT
CpG-LacZ   (533) GGCTGGCTGTCATGGTGCTCAGGTGGTCTGATGGCAGCTACCTGGAAGAC
Consensus  (551) G CT GC GT ATGGTGCT  G TGG  TGA GGCAG TA CTGGAAGA
                 601                                            650
CpG+LacZ   (601) CAGGATATGTGGCGGATGAGCGGCATTTTCCGTGACGTCTCGTTGCTGCA
CpG-LacZ   (583) CAAGACATGTGGAGGATGTCTGGCATCTTCAGGGATGTGAGCCTGCTGCA
Consensus  (601) CA GA ATGTGG GGATG   GGCAT TTC G GA GT     TGCTGCA
                 651                                            700
```

FIG. 11B

```
 CpG+LacZ   (651) TAAACCGACTACACAAATCAGCGATTTCCATGTTGCCACTCGCTTTAATG
 CpG-LacZ   (633) CAAGCCCACCACCCAGATTTCTGACTTCCATGTTGCCACCAGGTTCAATG
Consensus   (651)  AA CC AC AC CA AT    GA TTCCATGTTGCCAC  G TT AATG
                  701                                            750
 CpG+LacZ   (701) ATGATTTCAGCCGCGCTGTACTGGAGGCTGAAGTTCAGATGTGCGGCGAG
 CpG-LacZ   (683) ATGACTTCAGCAGAGCTGTGCTGGAGGCTGAGGTGCAGATGTGTGGAGAA
Consensus   (701) ATGA TTCAGC G GCTGT CTGGAGGCTGA GT CAGATGTG GG GA
                  751                                            800
 CpG+LacZ   (751) TTGCGTGACTACCTACGGGTAACAGTTTCTTTATGGCAGGGTGAAACGCA
 CpG-LacZ   (733) CTCAGAGACTACCTGAGAGTCACAGTGAGCCTCTGGCAAGGTGAGACCCA
Consensus   (751)  T  G GACTACCT  G GT ACAGT     T TGGCA GGTGA AC CA
                  801                                            850
 CpG+LacZ   (801) GGTCGCCAGCGGCACCGCGCCTTTCGGCGGTGAAATTATCGATGAGCGTG
 CpG-LacZ   (783) GGTGGCCTCTGGCACAGCCCCCTTTGGAGGAGAGATCATTGATGAGAGAG
Consensus   (801) GGT GCC   GGCAC GC CC TT GG GG GA AT AT GATGAG G G
                  851                                            900
 CpG+LacZ   (851) GTGGTTATGCCGATCGCGTCACACTACGTCTGAACGTCGAAAACCCGAAA
 CpG-LacZ   (833) GAGGCTATGCTGACAGAGTCACCCTGAGGCTCAATGTGGAGAACCCCAAG
Consensus   (851) G GG TATGC GA  G GTCAC CT  G CT AA GT GA AACCC AA
                  901                                            950
 CpG+LacZ   (901) CTGTGGAGCGCCGAAATCCCGAATCTCTATCGTGCGGTGGTTGAACTGCA
 CpG-LacZ   (883) CTGTGGTCTGCTGAGATCCCCAACCTCTACAGGGCTGTTGTTGAGCTGCA
Consensus   (901) CTGTGG   GC GA ATCCC AA CTCTA  G GC GT GT GA CTGCA
                  951                                           1000
 CpG+LacZ   (951) CACCGCCGACGGCACGCTGATTGAAGCAGAAGCCTGCGATGTCGGTTTCC
 CpG-LacZ   (933) CACTGCTGATGGCACCCTGATTGAAGCTGAAGCCTGTGATGTTGGATTCA
Consensus   (951) CAC GC GA GGCAC CTGATTGAAGC GAAGCCTG GATGT GG TTC
                  1001                                          1050
 CpG+LacZ  (1001) GCGAGGTGCGGATTGAAAATGGTCTGCTGCTGCTGAACGGCAAGCCGTTG
 CpG-LacZ   (983) GAGAAGTCAGGATTGAGAATGGCCTGCTGCTGCTCAATGGCAAGCCTCTG
Consensus  (1001) G GA GT  GGATTGA AATGG CTGCTGCTGCT AA GGCAAGCC  TG
                  1051                                          1100
 CpG+LacZ  (1051) CTGATTCGAGGCGTTAACCGTCACGAGCATCATCCTCTGCATGGTCAGGT
 CpG-LacZ  (1033) CTCATCAGGGGAGTCAACAGGCATGAGCACCACCCTCTGCATGGACAAGT
Consensus  (1051) CT AT  G GG GT AAC G CA GAGCA CA CCTCTGCATGG CA GT
                  1101                                          1150
 CpG+LacZ  (1101) CATGGATGAGCAGACGATGGTGCAGGATATCCTGCTGATGAAGCAGAACA
 CpG-LacZ  (1083) GATGGATGAACAGACAATGGTGCAAGATATCCTGCTAATGAAGCAGAACA
Consensus  (1101)  ATGGATGA CAGAC ATGGTGCA GATATCCTGCT ATGAAGCAGAACA
                  1151                                          1200
 CpG+LacZ  (1151) ACTTTAACGCCGTGCGCTGTTCGCATTATCCGAACCATCCGCTGTGGTAC
 CpG-LacZ  (1133) ACTTCAATGCTGTCAGGTGCTCTCACTACCCCAACCACCCTCTCTGGTAC
Consensus  (1151) ACTT AA GC GT  G TG TC CA TA CC AACCA CC CT TGGTAC
                  1201                                          1250
 CpG+LacZ  (1201) ACGCTGTGCGACCGCTACGGCCTGTATGTGGTGGATGAAGCCAATATTGA
 CpG-LacZ  (1183) ACCCTGTGTGACAGGTATGGCCTGTATGTTGTTGATGAAGCCAACATTGA
Consensus  (1201) AC CTGTG GAC G TA GGCCTGTATGT GT GATGAAGCCAA ATTGA
                  1251                                          1300
 CpG+LacZ  (1251) AACCCACGGCATGGTGCCAATGAATCGTCTGACCGATGATCCGCGCTGGC
 CpG-LacZ  (1233) GACACATGGCATGGTGCCCATGAACAGGCTCACAGATGACCCCAGGTGGC
Consensus  (1251)  AC CA GGCATGGTGCC ATGAA  G CT AC GATGA CC  G TGGC
                  1301                                          1350
 CpG+LacZ  (1301) TACCGGCGATGAGCGAACGCGTAACGCGAATGGTGCAGCGCGATCGTAAT
 CpG-LacZ  (1283) TGCCTGCCATGTCTGAGAGAGTGACCAGGATGGTGCAGAGAGACAGGAAC
```

FIG. 11C

```
Consensus  (1301) T CC GC ATG   GA  G GT AC  G ATGGTGCAG G GA  G AA
                  1351                                             1400
 CpG+LacZ  (1351) CACCCGAGTGTGATCATCTGGTCGCTGGGGAATGAATCAGGCCACGGCGC
 CpG-LacZ  (1333) CACCCCTCTGTGATCATCTGGTCTCTGGGCAATGAGTCTGGACATGGAGC
Consensus  (1351) CACCC   TGTGATCATCTGGTC CTGGG AATGA TC GG CA GG GC
                  1401                                             1450
 CpG+LacZ  (1401) TAATCACGACGCGCTGTATCGCTGGATCAAATCTGTCGATCCTTCCCGCC
 CpG-LacZ  (1383) CAACCATGATGCTCTCTACAGGTGGATCAAGTCTGTTGACCCCAGCAGAC
Consensus  (1401)  AA CA GA GC CT TA  G TGGATCAA TCTGT GA CC   C G C
                  1451                                             1500
 CpG+LacZ  (1451) CGGTGCAGTATGAAGGCGGCGGAGCCGACACCACGGCCACCGATATTATT
 CpG-LacZ  (1433) CTGTGCAGTATGAAGGAGGTGGAGCAGACACCACAGCCACAGACATCATC
Consensus  (1451) C GTGCAGTATGAAGG GG GGAGC GACACCAC GCCAC GA AT AT
                  1501                                             1550
 CpG+LacZ  (1501) TGCCCGATGTACGCGCGCGTGGATGAAGACCAGCCCTTCCCGGCTGTGCC
 CpG-LacZ  (1483) TGCCCCATGTATGCCAGGGTTGATGAGGACCAGCCCTTCCCTGCTGTGCC
Consensus  (1501) TGCCC ATGTA GC  G GT GATGA GACCAGCCCTTCCC GCTGTGCC
                  1551                                             1600
 CpG+LacZ  (1551) GAAATGGTCCATCAAAAAATGGCTTTCGCTACCTGGAGAGACGCGCCCGC
 CpG-LacZ  (1533) CAAGTGGAGCATCAAGAAGTGGCTCTCTCTGCCTGGAGAGACCAGACCTC
Consensus  (1551)  AA TGG  CATCAA AA TGGCT TC CT CCTGGAGAGAC  G CC C
                  1601                                             1650
 CpG+LacZ  (1601) TGATCCTTTGCGAATACGCCCACGCGATGGGTAACAGTCTTGGCGGTTTC
 CpG-LacZ  (1583) TGATCCTGTGTGAATATGCACATGCAATGGGCAACTCTCTGGGAGGCTTT
Consensus  (1601) TGATCCT TG GAATA GC CA GC ATGGG AAC  TCT GG GG TT
                  1651                                             1700
 CpG+LacZ  (1651) GCTAAATACTGGCAGGCGTTTCGTCAGTATCCCCGTTTACAGGGCGGCTT
 CpG-LacZ  (1633) GCCAAGTACTGGCAAGCCTTCAGACAGTACCCCAGGCTGCAAGGAGGATT
Consensus  (1651) GC AA TACTGGCA GC TT  G CAGTA CCC G  T CA GG GG TT
                  1701                                             1750
 CpG+LacZ  (1701) CGTCTGGGACTGGGTGGATCAGTCGCTGATTAAATATGATGAAAACGGCA
 CpG-LacZ  (1683) TGTGTGGGACTGGGTGGACCAATCTCTCATCAAGTATGATGAGAATGGCA
Consensus  (1701)  GT TGGGACTGGGTGGA CA TC CT AT AA TATGATGA AA GGCA
                  1751                                             1800
 CpG+LacZ  (1751) ACCCGTGGTCGGCTTACGGCGGTGATTTTGGCGATACGCCGAACGATCGC
 CpG-LacZ  (1733) ACCCCTGGTCTGCCTATGGAGGAGACTTTGGTGACACCCCAATGACAGG
Consensus  (1751) ACCC TGGTC GC TA GG GG GA TTTGG GA AC CC AA GA  G
                  1801                                             1850
 CpG+LacZ  (1801) CAGTTCTGTATGAACGGTCTGGTCTTTGCCGACCGCACGCCGCATCCAGC
 CpG-LacZ  (1783) CAGTTCTGCATGAATGGCCTGGTCTTTGCAGACAGGACCCCTCACCCTGC
Consensus  (1801) CAGTTCTG ATGAA GG CTGGTCTTTGC GAC G AC CC CA CC GC
                  1851                                             1900
 CpG+LacZ  (1851) GCTGACGGAAGCAAAACACCAGCAGCAGTTTTTCCAGTTCCGTTTATCCG
 CpG-LacZ  (1833) CCTCACAGAGGCCAAGCACCAGCAACAGTTCTTCCAGTTCAGGCTGTCTG
Consensus  (1851)  CT AC GA GC AA CACCAGCA CAGTT TTCCAGTTC G  T TC G
                  1901                                             1950
 CpG+LacZ  (1901) GGCAAACCATCGAAGTGACCAGCGAATACCTGTTCCGTCATAGCGATAAC
 CpG-LacZ  (1883) GACAGACCATTGAGGTGACATCTGAGTACCTCTTCAGGCACTCTGACAAT
Consensus  (1901) G CA ACCAT GA GTGAC    GA TACCT TTC G CA    GA AA
                  1951                                             2000
 CpG+LacZ  (1951) GAGCTCCTGCACTGGATGGTGGCGCTGGATGGTAAGCCGCTGGCAAGCGG
 CpG-LacZ  (1933) GAGCTCCTGCACTGGATGGTGGCCCTGGATGGCAAGCCTCTGGCTTCTGG
Consensus  (1951) GAGCTCCTGCACTGGATGGTGGC CTGGATGG AAGCC CTGGC    GG
                  2001                                             2050
```

FIG. 11D

```
 CpG+LacZ  (2001) TGAAGTGCCTCTGGATGTCGCTCCACAAGGTAAACAGTTGATTGAACTGC
 CpG-LacZ  (1983) TGAGGTGCCTCTGGATGTGGCCCCTCAAGGAAAGCAGCTGATTGAACTGC
Consensus  (2001) TGA GTGCCTCTGGATGT GC CC CAAGG AA CAG TGATTGAACTGC
                  2051                                           2100
 CpG+LacZ  (2051) CTGAACTACCGCAGCCGGAGAGCGCCGGCCAACTCTGGCTCACAGTACGC
 CpG-LacZ  (2033) CTGAGCTGCCTCAGCCAGAGTCTGCTGGACAACTGTGGCTAACAGTGAGG
Consensus  (2051) CTGA CT CC CAGCC GAG   GC GG CAACT TGGCT ACAGT  G 
                  2101                                           2150
 CpG+LacZ  (2101) GTAGTGCAACCGAACGCGACCGCATGGTCAGAAGCCGGGCACATCAGCGC
 CpG-LacZ  (2083) GTGGTTCAGCCCAATGCAACAGCTTGGTCTGAGCAGGCCACATCTCTGC
Consensus  (2101) GT GT CA CC AA GC AC GC TGGTC GA GC GG CACATC   GC
                  2151                                           2200
 CpG+LacZ  (2151) CTGGCAGCAGTGGCGTCTGGCGGAAAACCTCAGTGTGACGCTCCCCGCCG
 CpG-LacZ  (2133) ATGGCAGCAGTGGAGGCTGGCTGAGAACCTCTCTGTGACCCTGCCTGCTG
Consensus  (2151)  TGGCAGCAGTGG G CTGGC GA AACCTC  TGTGAC CT CC GC G
                  2201                                           2250
 CpG+LacZ  (2201) CGTCCCACGCCATCCCGCATCTGACCACCAGCGAAATGGATTTTTGCATC
 CpG-LacZ  (2183) CCTCTCATGCCATCCCTCACCTGACAACATCTGAAATGGACTTCTGCATT
Consensus  (2201) C TC CA GCCATCCC CA CTGAC AC    GAAATGGA TT TGCAT 
                  2251                                           2300
 CpG+LacZ  (2251) GAGCTGGGTAATAAGCGTTGGCAATTTAACCGCCAGTCAGGCTTTCTTTC
 CpG-LacZ  (2233) GAGCTGGGCAACAAGAGATGGCAGTTCAACAGGCAGTCTGGCTTCCTGTC
Consensus  (2251) GAGCTGGG AA AAG G TGGCA TT AAC G CAGTC GGCTT CT TC
                  2301                                           2350
 CpG+LacZ  (2301) ACAGATGTGGATTGGCGATAAAAACCAACTGCTGACGCCGCTGCGCGATC
 CpG-LacZ  (2283) TCAGATGTGGATTGGAGACAAGAAGCAGCTCCTCACCCCTCTCAGGGACC
Consensus  (2301)  CAGATGTGGATTGG GA AA AA CA CT CT AC CC CT  G GA C
                  2351                                           2400
 CpG+LacZ  (2351) AGTTCACCCGTGCACCGCTGGATAACGACATTGGCGTAAGTGAAGCGACC
 CpG-LacZ  (2333) AATTCACCAGGCCTCCTCTGGACAATGACATTGGAGTGTCTGAGGCCACC
Consensus  (2351) A TTCACC G GC CC CTGGA AA GACATTGG GT   TGA GC ACC
                  2401                                           2450
 CpG+LacZ  (2401) CGCATTGACCCTAACGCCTGGGTCGAACGCTGGAAGGCGGCGGGCCATTA
 CpG-LacZ  (2383) AGGATTGACCCAAATGCTTGGGTGGAGAGGTGGAAGGCTGCTGGACACTA
Consensus  (2401)  G ATTGACCC AA GC TGGGT GA  G TGGAAGGC GC GG CA TA
                  2451                                           2500
 CpG+LacZ  (2451) CCAGGCCGAAGCAGCGTTGTTGCAGTGCACGGCAGATACACTTGCTGATG
 CpG-LacZ  (2433) CCAGGCTGAGGCTGCCCTGCTCCAGTGCACAGCAGACACCCTGGCTGATG
Consensus  (2451) CCAGGC GA GC GC  TG T CAGTGCAC GCAGA AC CT GCTGATG
                  2501                                           2550
 CpG+LacZ  (2501) CGGTGCTGATTACGACCGCTCACCGCGTGGCAGCATCAGGGGAAAACCTTA
 CpG-LacZ  (2483) CTGTTCTGATCACCACAGCCCATGCTTTGGCAGCACCAAGGCAAGACCCTG
Consensus  (2501) C GT CTGAT AC AC GC CA GC TGGCAGCA CA GG AA ACC T 
                  2551                                           2600
 CpG+LacZ  (2551) TTTATCAGCCGGAAAACCTACCGGATTGATGGTAGTGGTCAAATGGCGAT
 CpG-LacZ  (2533) TTCATCAGCAGAAAGACCTACAGGATTGATGGCTCTGGACAGATGGCAAT
Consensus  (2551) TT ATCAGC G AA ACCTAC GGATTGATGG   TGG CA ATGGC AT
                  2601                                           2650
 CpG+LacZ  (2601) TACCGTTGATGTTGAAGTGGCGAGCGATACACCGCATCCGGCGCGGATTG
 CpG-LacZ  (2583) CACAGTGGATGTGGAGGTTGCCTCTGACACACCTCAACCTGCAAGGATTG
Consensus  (2601)  AC GT GATGT GA GT GC    GA ACACC CA CC GC  GGATTG
                  2651                                           2700
 CpG+LacZ  (2651) GCCTGAACTGCCAGCTGGCGCAGGTAGCAGAGCGGGTAAACTGGCTCGGA
 CpG-LacZ  (2633) GCCTGAACTGTCAACTGGCACAGGTGGCTGAGAGGCTGAACTGGCTGGGC
```

FIG. 11E

Consensus (2651) GCCTGAACTG CA CTGGC CAGGT GC GAG GGGT AACTGGCT GG
2701 2750
CpG+LacZ (2701) TTAGGGCCGCAAGAAAACTATCCCGACCGCCTTACTGCCGCCTGTTTTGA
CpG-LacZ (2683) TTAGGCCCTCAGGAGAACTACCCTGACAGGCTGACAGCTGCCTGCTTTGA
Consensus (2701) TTAGG CC CA GA AACTA CC GAC G CT AC GC GCCTG TTTGA
2751 2800
CpG+LacZ (2751) CCGCTGGGATCTGCCATTGTCAGACATGTATACCCCGTACGTCTTCCCGA
CpG-LacZ (2733) CAGGTGGGACCTGCCTCTGTCTGACATGTACACCCCTTATGTGTTCCCTT
Consensus (2751) C G TGGGA CTGCC  TGTC GACATGTA ACCCC TA GT TTCCC
2801 2850
CpG+LacZ (2801) GCGAAAACGGTCTGCGCTGCGGAACGCGCGAATTGAATTATGGCCCACAC
CpG-LacZ (2783) CTGAGAATGGCCTGAGGTGTGGCACCAGGGAGCTGAACTATGGTCCTCAC
Consensus (2801)   GA AA GG CTG G TG GG AC  G GA  TGAA TATGG CC CAC
2851 2900
CpG+LacZ (2851) CAGTGGCGCGGCGACTTCCAGTTCAACATCAGCCCGCTACAGTCAACAGCA
CpG-LacZ (2833) CAGTGGAGGGGAGACTTCCAGTTCAACATCTCCAGGTACTCTCAGCAACA
Consensus (2851) CAGTGG G GG GACTTCCAGTTCAACATC  C G TAC  TCA CA CA
2901 2950
CpG+LacZ (2901) ACTGATGGAAACCAGCCATCGCCATCTGCTGCACGCGGAAGAAGGCACAT
CpG-LacZ (2883) GCTCATGGAAACCTCTCACAGGCACCTGCTCCATGCAGAGGAGGGCACCT
Consensus (2901)  CT ATGGAAACC   CA  G CA CTGCT CA GC GA GA GG AC T
2951 3000
CpG+LacZ (2951) GGCTGAATATCGACGGTTTCCATATGGGAATTGGTGGCGACGACTCCTGG
CpG-LacZ (2933) GGCTGAACATTGATGGCTTCCACATGGGCATTGGAGGAGATGACTCTTGG
Consensus (2951) GGCTGAA AT GA GG TTCCA ATGGG ATTGG GG GA GACTC TGG
3001 3050
CpG+LacZ (3001) AGCCCGTCAGTAATCCGCGGGAATTCCAGCTGAGCGCCGGTCGGTACCATTA
CpG-LacZ (2983) TCTCCTTCTGTGTCTGCTGATTCCAGTTATCTGCTGGCAGGGTACCACTA
Consensus (3001)    CC TC GT TC GC GA TTCCAG T    GC GG  GGTACCA TA
3051 3072
CpG+LacZ (3051) CCAGTTGGTCTGGTGTCAAAAA
CpG-LacZ (3033) TCAGCTGGTGTGGTGCCAGAAG
Consensus (3051)  CAG TGGT TGGTG CA AA

FIG. 12A

```
                                                 1
50
   hTnT intron 9 with S100A1 exons      (1)
GAATTCTGTACAGTAGCTTCCACCATGGGCTCTGAGCTGGAGACAGCTAT
h TnnT cardiac Exons 9-10 intron 9      (1)
--------------------------------------------------
                         Consensus      (1)
                                                  51
100
   hTnT intron 9 with S100A1 exons     (51)
GAGACCCTGATCAATGTGTTCCATGCCCACTCTGGCAAGGAGGGAGACAA
h TnnT cardiac Exons 9-10 intron 9      (1) -
-AGAAGGCCAAGGAGCTGTGGCAGAGCATCTATAACTTGGAGGCAGAGAA
                         Consensus     (51)
GAGA     A   A  TGT  CA   C  CT T  C  GGAGG AGA A
                                                  101
150
   hTnT intron 9 with S100A1 exons    (101)
AGTACAAGCTGAGCAAGAAGGAGCTGAAGGAGCTGCTCCAGACAGAGCTG
h TnnT cardiac Exons 9-10 intron 9     (50)
AGTTCGACCTGC----AGGAGAAGTTCAAGCAGC-------A--GAAATA
                         Consensus    (101)
AGT C A CTG    AG AG AG T AAG AGC        A  GA  T
                                                  151
200
   hTnT intron 9 with S100A1 exons    (151)
TCTGGCTTCCTGGATGCCCAGAAGGTGAGTGCCATGCTGTCCCCAGCCCA
h TnnT cardiac Exons 9-10 intron 9     (87)
TGAGG-----TGG--GCC------------GCCATGCTGTCCCC-GCCCA
                         Consensus    (151)
T  GG     TGG  GCC            GCCATGCTGTCCCC GCCCA
                                                  201
250
   hTnT intron 9 with S100A1 exons    (201)
GCATCTCCATCTCACACTCCTCCTGGTTCACTGGGTCCTGGTAATACTG-
h TnnT cardiac Exons 9-10 intron 9    (117)
GCATCTCCATCTCACACTCCTCCTGGTTCACTGGGTCC-GGTAATACTGC
                         Consensus    (201)
GCATCTCCATCTCACACTCCTCCTGGTTCACTGGGTCC GGTAATACTG
                                                  251
300
   hTnT intron 9 with S100A1 exons    (250)
-----GTCCCTGGGTCCCTGTCCCTATTCCCCAACAGCCCCCTTCAGCTC
h TnnT cardiac Exons 9-10 intron 9    (166)
TGCAGGTCCCTGGGTCCCTGTCCCTATTCCCCAACAGCCCCCTTCAGCTC
                         Consensus    (251)
     GTCCCTGGGTCCCTGTCCCTATTCCCCAACAGCCCCCTTCAGCTC
                                                  301
350
   hTnT intron 9 with S100A1 exons    (295)
CTGCATCTGCCCCTGCTGCCTGGCCTTCAGCAGTGTTCCATGTCCACC-C
h TnnT cardiac Exons 9-10 intron 9    (216)
CTGCATCTGCCCCTGCTGCCTGGCCTTCAGCAGTGTTCCATGTCCACCGC
                         Consensus    (301)
CTGCATCTGCCCCTGCTGCCTGGCCTTCAGCAGTGTTCCATGTCCACC C
```

FIG. 12B

```
                                              351
400
  hTnT intron 9 with S100A1 exons    (344)
ATTGACCACTGCTTGCTGGAAGTGTCTGAGAGCTC-CTGGGGCTGAGCAG
h TnnT cardiac Exons 9-10 intron 9    (266)
ATTGACGACTGCTTGCTGGAAGTGTCTGAGAGCTCGCTGGGGCTGAGCAG
                          Consensus    (351)
ATTGAC ACTGCTTGCTGGAAGTGTCTGAGAGCTC CTGGGGCTGAGCAG
                                              401
450
  hTnT intron 9 with S100A1 exons    (393)
AGACACTTTCCTGGTGTTCCAACCCTGGGGGTCTCCAACAC-TTGAGGCA
h TnnT cardiac Exons 9-10 intron 9    (316)
AGACACTTTCCTGGTGTTCCAACCCTGGGGGTCTCCAACACGTTGAGGCA
                          Consensus    (401)
AGACACTTTCCTGGTGTTCCAACCCTGGGGGTCTCCAACAC TTGAGGCA
                                              451
500
  hTnT intron 9 with S100A1 exons    (442)
GCAGCTCAGTGATCTGAGCTGGTTACAAGGACCTGGATGCACCAAGCCAA
h TnnT cardiac Exons 9-10 intron 9    (366)
GCAGCTCAGTGATCTGAGCTGGTTACAAGGACCAGGATGCACCAAGCCA-
                          Consensus    (451)
GCAGCTCAGTGATCTGAGCTGGTTACAAGGACC GGATGCACCAAGCCA
                                              501
550
  hTnT intron 9 with S100A1 exons    (492)
GGACCCCCAGTGGAAGGGGAGTGCTGCCAACAGAGAGGTGCTTCTCCCCA
h TnnT cardiac Exons 9-10 intron 9    (415)
GGACCCCCAGTGGAAGGGGAGTGCTGCCAACAGAGAGGTGCTTCTCCCCA
                          Consensus    (501)
GGACCCCCAGTGGAAGGGGAGTGCTGCCAACAGAGAGGTGCTTCTCCCCA
                                              551
600
  hTnT intron 9 with S100A1 exons    (542)
CATACACCCAAGGTCCTGGTGTGGGCACAATTAGGCTGAGCCTCAAGCTC
h TnnT cardiac Exons 9-10 intron 9    (465)
CATACACCCAAGGTCCTGGTGTGGGCACAATTAGGCTGAGCCTCAAGCTC
                          Consensus    (551)
CATACACCCAAGGTCCTGGTGTGGGCACAATTAGGCTGAGCCTCAAGCTC
                                              601
650
  hTnT intron 9 with S100A1 exons    (592)
ACAGTCTTT-GGAGTCCTATGTGCACTAATGAGGGTCTTAGGTGAACAGA
h TnnT cardiac Exons 9-10 intron 9    (515)
ACAGTCTTTCGGAGTCCTATGTGCACTAATGAGGGTCTTAGGTGAACAGA
                          Consensus    (601)
ACAGTCTTT GGAGTCCTATGTGCACTAATGAGGGTCTTAGGTGAACAGA
                                              651
```

FIG. 12C 700
hTnT intron 9 with S100A1 exons (641)
CACT-GGCAAGGAAATGGCTTAGAGGACACTGATGCTGCATACCATGAGC
h TnnT cardiac Exons 9-10 intron 9 (565)
CACCAGGCAAGGAAATGGCTTAGAGGACACTGATGCTGCATACCG-GAGC
Consensus (651)
CAC GGCAAGGAAATGGCTTAGAGGACACTGATGCTGCATACC GAGC
701

750
hTnT intron 9 with S100A1 exons (690)
TTAGACCTGGGC-CCAGTCCTTCCTTACCCACCACCCCCAGCCCCTGGTC
h TnnT cardiac Exons 9-10 intron 9 (614)
TTAGACCTGGGCGCCAGTCCTTCCTTACCCACCACCCCCGAGCCCCGGTC
Consensus (701)
TTAGACCTGGGC CCAGTCCTTCCTTACCCACCACCCCC CCC GGTC
751

800
hTnT intron 9 with S100A1 exons (739)
CCTAGGGCCTCTTTGCTACCTAAGGGAAGAACTTCAGCTTCCCCTGGAAG
h TnnT cardiac Exons 9-10 intron 9 (664)
CC-AGGGCCTCTTTGCTACCTAAGGGAAGAA-TTCAGCTTCCCCTGGAAG
Consensus (751)
CC AGGGCCTCTTTGCTACCTAAGGGAAGAA TTCAGCTTCCCCTGGAAG
801

850
hTnT intron 9 with S100A1 exons (789)
GTCTCCTTTGCTGCTCCTGCCAAACCACTCCTCCCTGGGCAAGAAGCCCC
h TnnT cardiac Exons 9-10 intron 9 (712)
GTCTCCTTTGCTGCTCCTGCCAAACCACTCCTCCCTGGGCAAGAAGCCCC
Consensus (801)
GTCTCCTTTGCTGCTCCTGCCAAACCACTCCTCCCTGGGCAAGAAGCCCC
851

900
hTnT intron 9 with S100A1 exons (839)
T-GCTGGGCTGGCT----------TGGCTAC-GGGTACTCCCACCTCCCA
h TnnT cardiac Exons 9-10 intron 9 (762)
TCGCTGGGCAGGCTCAGGCTGCAGTGGCTACAGGGTACTCCCACCTCCCA
Consensus (851)
T GCTGGGC GGCT TGGCTAC GGGTACTCCCACCTCCCA
901

950
hTnT intron 9 with S100A1 exons (877)
ATA-GGAGAGAGGCTGTATTGCCTGGTGACAGTGGCATGGACTTTGGAGC
h TnnT cardiac Exons 9-10 intron 9 (812)
ATACGGAGAGAGGCTGTATTGCCTGGTGACAGTGGCATGGACTTTGGAGC
Consensus (901)
ATA GGAGAGAGGCTGTATTGCCTGGTGACAGTGGCATGGACTTTGGAGC
951

FIG. 12D

```
1000
   hTnT intron 9 with S100A1 exons    (926)
CATAATGCCTGGGTTGAATTTCTACCTGTGCCCCTCACTGGCTGTGTGAC
h TnnT cardiac Exons 9-10 intron 9    (862)
CATAATGCCTGGGTTGAATTTCTACCTGTGCCCCTCACTGGCTGTGTGAC
                         Consensus    (951)
CATAATGCCTGGGTTGAATTTCTACCTGTGCCCCTCACTGGCTGTGTGAC
                                            1001
1050
   hTnT intron 9 with S100A1 exons    (976)
ATTGGCAGAGTTAGTCCACTGTTCCTTGCCTCCATTTCCACATGGTAACA
h TnnT cardiac Exons 9-10 intron 9    (912)
ATTGGGTGAGTTAGTCCACTGTTCCTTGCCTCCATTTCCACA-GGTAACA
                         Consensus   (1001)
ATTGG  GAGTTAGTCCACTGTTCCTTGCCTCCATTTCCACA GGTAACA
                                            1051
1100
   hTnT intron 9 with S100A1 exons   (1026)
CTACAATATACTTCAGAGGGTGATTGTGAGGGTTACAGAGATAATACTAA
h TnnT cardiac Exons 9-10 intron 9    (961)
CTACAATATACTTCAGAGGGTGATTGTGAGGGTTACAGAGATAATACTAA
                         Consensus   (1051)
CTACAATATACTTCAGAGGGTGATTGTGAGGGTTACAGAGATAATACTAA
                                            1101
1150
   hTnT intron 9 with S100A1 exons   (1076)
TTGTTATTATTGCTATAGTGTTCCAACCACTGTTCCAAGCATGTCCCATG
h TnnT cardiac Exons 9-10 intron 9   (1011)
TTGTTATTATTGCTATAGTGTTCCAACCACTGTTCCAAGCATGTCCCATG
                         Consensus   (1101)
TTGTTATTATTGCTATAGTGTTCCAACCACTGTTCCAAGCATGTCCCATG
                                            1151
1200
   hTnT intron 9 with S100A1 exons   (1126)
TATTAACTTACTATGCCCTCATAGCAGCCCTATGGGTTCATATCTGGGAA
h TnnT cardiac Exons 9-10 intron 9   (1061)
TATTAACTTACTATGCCCTCATAGCAGCCCTATGGGTTCATATCTGGGAA
                         Consensus   (1151)
TATTAACTTACTATGCCCTCATAGCAGCCCTATGGGTTCATATCTGGGAA
                                            1201
1250
   hTnT intron 9 with S100A1 exons   (1176)
GGTGCTCAGAA--GAGCCTGGCACCCACTAAATGCTCAGCA--TGTCAGC
h TnnT cardiac Exons 9-10 intron 9   (1111)
GGTGCTCAGGACAGAGCCTGGCACCCACTAAATGCTCAGCAGGTGTCAGC
                         Consensus   (1201)
GGTGCTCAG A  GAGCCTGGCACCCACTAAATGCTCAGCA  TGTCAGC
                                            1251
```

FIG. 12E 1300
hTnT intron 9 with S100A1 exons (1222)
CATTGTTATGGCCTCTCTAGTCCTGTGCCTTCCACTTTTTTCTCTTTTTT
h TnnT cardiac Exons 9-10 intron 9 (1161)
CATTGTTATGGCCTCTCTAGTCCTGTGCCTTCCACTTTTTTCTCTTTTTT
Consensus (1251)
CATTGTTATGGCCTCTCTAGTCCTGTGCCTTCCACTTTTTTCTCTTTTTT
1301

1350
hTnT intron 9 with S100A1 exons (1272)
TGGTTCCACACTGAACTCTGCACCAAGCCAAAGGACACAGATTTGCCAAA
h TnnT cardiac Exons 9-10 intron 9 (1211)
TGGTTCCACACTGAACTCTGCACCGGCCAACAGGACACAGATTTGCCAAA
Consensus (1301)
TGGTTCCACACTGAACTCTGCACC   C A AGGACACAGATTTGCCAAA
1351

1400
hTnT intron 9 with S100A1 exons (1322)
CTTTGGGGCAGCACCT-----GGGTGGTGCATGGGGATGCTACTGCTCAA
h TnnT cardiac Exons 9-10 intron 9 (1261)
CTTTGGGGCAGCACCCTGCAGGGGTGGTGCATGGGGATGCTACTGCTCAA
Consensus (1351)
CTTTGGGGCAGCACC      GGGTGGTGCATGGGGATGCTACTGCTCAA
1401

1450
hTnT intron 9 with S100A1 exons (1367)
AGGGCACAGCTTCCTGGGATGGTGGGCAGCTGGGCATGGGTGCCCCAGAG
h TnnT cardiac Exons 9-10 intron 9 (1311)
AGGGCACAGCTTCC-GGGATGGTGGGCAGCTGGGCAGGGGTGCCCCAGAG
Consensus (1401)
AGGGCACAGCTTCC GGGATGGTGGGCAGCTGGGCA GGGTGCCCCAGAG
1451

1500
hTnT intron 9 with S100A1 exons (1417)
GGGTCTGGGGCTGGGCTGCTAGGAGGGCTCCATGACACAGCCTCCAGCTT
h TnnT cardiac Exons 9-10 intron 9 (1360)
GGGTCTGGGGCTGGGCTGCTAGGAGGGCTCCATGACACAGCCTCCAGCTT
Consensus (1451)
GGGTCTGGGGCTGGGCTGCTAGGAGGGCTCCATGACACAGCCTCCAGCTT
1501

1550
hTnT intron 9 with S100A1 exons (1467)
TGTGCCCAGCTCTCAGAGGCCCTTCTTATGGGACTCTCATATCCTGAACC
h TnnT cardiac Exons 9-10 intron 9 (1410)
TGTGCCCAGCTCTCAGAGGCCCTTCTTATGGGACTCTCATATCCTGAACC
Consensus (1501)
TGTGCCCAGCTCTCAGAGGCCCTTCTTATGGGACTCTCATATCCTGAACC
1551

1600
hTnT intron 9 with S100A1 exons (1517)
TATTATGGCCCTGGGACCCCACAGTGGGAGGCCCATGAGGCATCCTGGAA
h TnnT cardiac Exons 9-10 intron 9 (1460)
TATTATGGCCCTGGGACCCCACAGTGGGAGGCCCATGAGGCATCCTGGAA
Consensus (1551)
TATTATGGCCCTGGGACCCCACAGTGGGAGGCCCATGAGGCATCCTGGAA

FIG. 12F

```
                                                    1601
1650
   hTnT intron 9 with S100A1 exons  (1567)
GGCTTCTCCTTGGCTTCTGCCTGTGGTACAAGG-CCCCTCCTGTCCCTTA
h TnnT cardiac Exons 9-10 intron 9  (1510)
G-CTTCTCCTTGGCTTCTGCCTGTGGTACACGGGCCCCTCCTGACCCTTA
                          Consensus  (1601)
G CTTCTCCTTGGCTTCTGCCTGTGGTACA GG CCCCTCCTG CCCTTA
                                                    1651
1700
   hTnT intron 9 with S100A1 exons  (1616)
ACTATCCTA-CCCCTCCTACTCTTCCATGCTCCTCCTTCTCCTCCTGCAC
h TnnT cardiac Exons 9-10 intron 9  (1559)
ACTATCCTAACCCCTCCTACTCTTCCATGCTCCTCCTTCTCCTCCTGCAC
                          Consensus  (1651)
ACTATCCTA CCCCTCCTACTCTTCCATGCTCCTCCTTCTCCTCCTGCAC
                                                    1701
1750
   hTnT intron 9 with S100A1 exons  (1665)
TGCTGCACTCAGCCCCCTTCTCCCCATCCCCTGGCCACC------CCTGA-
h TnnT cardiac Exons 9-10 intron 9  (1609)
TGCTGCACTCAGCCCCCTTCTCCCCATCCCCAGGCCACCTGGGACCTGAG
                          Consensus  (1701)
TGCTGCACTCAGCCCCCTTCTCCCCATCCCC GGCCACC      CCTGA
                                                    1751
1800
   hTnT intron 9 with S100A1 exons  (1709)
CCA---------TCCTCCTTGCTCTTTGTCCTTCCC-CTTTTCTTGCAGGAT
h TnnT cardiac Exons 9-10 intron 9  (1659)
CCAGTCAGCTCCAGCGTTGCTCTTTGTCCTTCCCACTTTTCTTGCAGA--
                          Consensus  (1751)
CCA       TCC  C TTGCTCTTTGTCCTTCCC CTTTTCTTGCAG
                                                    1801
1850
   hTnT intron 9 with S100A1 exons  (1752)
GTGGATGCTGTGGACAAGGTGATGAAGGAGCTGGATGAGAATGGAGATGG
h TnnT cardiac Exons 9-10 intron 9  (1707)
-TCAATGTTCTCCGAAACAGGATCAACGA---TAACCAGAAAGT------
                          Consensus  (1801)
T  ATG T T    AA   GAT AA GA     A  AGAA G
                                                    1851
1900
   hTnT intron 9 with S100A1 exons  (1802)
GGAGGTGGACTTCCAGGAGTATGTGGTGCTGGTGGCTGCCCTGACAGTGG
h TnnT cardiac Exons 9-10 intron 9  (1747)
--------------------------------------------------
                          Consensus  (1851)
                                                    1901
```

FIG. 12G

```
1950
   hTnT intron 9 with S100A1 exons  (1852)
CCTGCAACAACTTCTTCTGGGAGAACAGCTGATGGTCTGCTAGCTCTAGA
h TnnT cardiac Exons 9-10 intron 9  (1747)
--------------------------------------------------
                         Consensus  (1901)
                                           1951
   hTnT intron 9 with S100A1 exons  (1902)
GGATCC
h TnnT cardiac Exons 9-10 intron 9  (1747)
------
                         Consensus  (1951)
```

FIG 13A

```
        Luciferase Alignment +/-CpG

             1                                                 50
Luciferase +CpG    (1) ATGGAAGATGCCAAAAACATTAAGAAGGGCCCAGCGCCATTCTACCCACT
Luciferase CpG-    (1) ATGGAAGATGCCAAAAACATTAAGAAGGGCCCAGCTCCATTCTACCCACT
      Consensus    (1) ATGGAAGATGCCAAAAACATTAAGAAGGGCCCAGC CCATTCTACCCACT

                       51                                               100
Luciferase +CpG   (51) CGAAGACGGGACCGCCGGCGAGCAGCTGCACAAAGCCATGAAGCGCTACG
Luciferase CpG-   (51) GGAAGATGGGACAGCTGGAGAGCAGCTGCACAAAGCCATGAAGAGATATG
      Consensus   (51)  GAAGA GGGAC GC GG GAGCAGCTGCACAAAGCCATGAAG G TA G

                       101                                              150
Luciferase +CpG  (101) CCCTGGTGCCCGGCACCATCGCCTTTACCGACGCACATATCGAGGTGGAC
Luciferase CpG-  (101) CCCTGGTGCCTGGCACCATTGCCTTTACAGATGCACATATTGAGGTGGAC
      Consensus  (101) CCCTGGTGCC GGCACCAT GCCTTTAC GA GCACATAT GAGGTGGAC

                       151                                              200
Luciferase +CpG  (151) ATTACCTACGCCGAGTACTTCGAGATGAGCGTTCGGCTGGCAGAAGCTAT
Luciferase CpG-  (151) ATTACCTATGCTGAGTACTTTGAGATGTCTGTTAGACTGGCAGAAGCTAT
      Consensus  (151) ATTACCTA GC GAGTACTT GAGATG   GTT G CTGGCAGAAGCTAT

                       201                                              250
Luciferase +CpG  (201) GAAGCGCTATGGGCTGAATACAAACCATCGGATCGTGGTGTGCAGCGAGA
Luciferase CpG-  (201) GAAGAGATATGGGCTGAATACAAACCATAGGATTGTGGTGTGCTCTGAGA
      Consensus  (201) GAAG G TATGGGCTGAATACAAACCAT GGAT GTGGTGTGC   GAGA

                       251                                              300
Luciferase +CpG  (251) ATAGCTTGCAGTTCTTCATGCCCGTGTTGGGTGCCCTGTTCATCGGTGTG
Luciferase CpG-  (251) ATAGCTTGCAGTTCTTCATGCCTGTGTTGGGTGCCCTGTTCATTGGTGTG
      Consensus  (251) ATAGCTTGCAGTTCTTCATGCC GTGTTGGGTGCCCTGTTCAT GGTGTG

                       301                                              350
Luciferase +CpG  (301) GCTGTGGCCCCAGCTAACGACATCTACAACGAGCGCGAGCTGCTGAACAG
Luciferase CpG-  (301) GCTGTGGCCCCAGCTAATGACATCTACAATGAGAGAGAGCTGCTGAACAG
      Consensus  (301) GCTGTGGCCCCAGCTAA GACATCTACAA GAG G GAGCTGCTGAACAG

                       351                                              400
Luciferase +CpG  (351) CATGGGCATCAGCCAGCCCACCGTCGTATTCGTGAGCAAGAAAGGGCTGC
Luciferase CpG-  (351) CATGGGCATCAGCCAGCCCACAGTGGTATTTGTGAGCAAGAAAGGGCTGC
      Consensus  (351) CATGGGCATCAGCCAGCCCAC GT GTATT GTGAGCAAGAAAGGGCTGC

                       401                                              450
Luciferase +CpG  (401) AAAAGATCCTCAACGTGCAAAAGAAGCTACCGATCATACAAAAGATCATC
Luciferase CpG-  (401) AAAAGATCCTCAATGTGCAAAAGAAGCTACCCATCATACAAAAGATCATC
      Consensus  (401) AAAAGATCCTCAA GTGCAAAAGAAGCTACC ATCATACAAAAGATCATC

                       451                                              500
Luciferase +CpG  (451) ATCATGGATAGCAAGACCGACTACCAGGGCTTCCAAAGCATGTACACCTT
Luciferase CpG-  (451) ATCATGGATAGCAAGACAGACTACCAGGGCTTCCAAAGCATGTATACCTT
      Consensus  (451) ATCATGGATAGCAAGAC GACTACCAGGGCTTCCAAAGCATGTA ACCTT

                       501                                              550
Luciferase +CpG  (501) CGTGACTTCCCATTTGCCACCCGGCTTCAACGAGTACGACTTCGTGCCCG
Luciferase CpG-  (501) TGTGACTTCCCATTTGCCACCTGGCTTCAATGAGTATGACTTTGTGCCTG
      Consensus  (501)  GTGACTTCCCATTTGCCACC GGCTTCAA GAGTA GACTT GTGCC G
```

FIG 13B

```
                            551                                              600
Luciferase +CpG     (551)   AGAGCTTCGACCGGGACAAAACCATCGCCCTGATCATGAACAGTAGTGGC
Luciferase CpG-     (551)   AGAGCTTTGACAGAGACAAAACCATTGCCCTGATCATGAACAGTAGTGGC
      Consensus     (551)   AGAGCTT GAC G GACAAAACCAT GCCCTGATCATGAACAGTAGTGGC

                            601                                              650
Luciferase +CpG     (601)   AGTACCGGATTGCCCAAGGGCGTAGCCCTACCGCACCGCACCGCTTGTGT
Luciferase CpG-     (601)   AGTACAGGATTGCCCAAGGGAGTAGCCCTACCTCACAGAACAGCTTGTGT
      Consensus     (601)   AGTAC GGATTGCCCAAGGG GTAGCCCTACC CAC G AC GCTTGTGT

                            651                                              700
Luciferase +CpG     (651)   CCGATTCAGTCATGCCCGCGACCCCATCTTCGGCAACCAGATCATCCCCG
Luciferase CpG-     (651)   CAGATTCAGTCATGCCAGGGACCCCATCTTTGGCAACCAGATCATCCCTG
      Consensus     (651)   C GATTCAGTCATGCC G GACCCCATCTT GGCAACCAGATCATCCC G

                            701                                              750
Luciferase +CpG     (701)   ACACCGCTATCCTCAGCGTGGTGCCATTTCACCACCGGCTTCGGCATGTTC
Luciferase CpG-     (701)   ACACAGCTATCCTCTCTGTGGTGCCATTTCATCATGGCTTTGGCATGTTC
      Consensus     (701)   ACAC GCTATCCTC   GTGGTGCCATTTCA CA GGCTT GGCATGTTC

                            751                                              800
Luciferase +CpG     (751)   ACCACGCTGGGCTACTTGATCTGCGGCTTTCGGGTCGTGCTCATGTACCG
Luciferase CpG-     (751)   ACCACCCTGGGCTACTTGATCTGTGGCTTTAGGGTGGTGCTCATGTATAG
      Consensus     (751)   ACCAC CTGGGCTACTTGATCTG GGCTTT GGGT GTGCTCATGTA  G

                            801                                              850
Luciferase +CpG     (801)   CTTCGAGGAGGAGCTATTCTTGCGCAGCTTGCAAGACTATAAGATTCAAT
Luciferase CpG-     (801)   ATTTGAGGAGGAGCTATTCTTGAGGAGCTTGCAAGACTATAAGATTCAAT
      Consensus     (801)    TT GAGGAGGAGCTATTCTTG G AGCTTGCAAGACTATAAGATTCAAT

                            851                                              900
Luciferase +CpG     (851)   CTGCCCTGCTGGTGCCCACACTATTTAGCTTCTTCGCTAAGAGCACTCTC
Luciferase CpG-     (851)   CTGCCCTGCTGGTGCCCACACTATTTAGCTTCTTTGCTAAGAGCACTCTC
      Consensus     (851)   CTGCCCTGCTGGTGCCCACACTATTTAGCTTCTT GCTAAGAGCACTCTC

                            901                                              950
Luciferase +CpG     (901)   ATCGACAAGTACGACCTAAGCAACTTGCACGAGATCGCCAGCGGCGGGGC
Luciferase CpG-     (901)   ATTGACAAGTATGACCTAAGCAACTTGCATGAGATTGCCTCTGGAGGGGC
      Consensus     (901)   AT GACAAGTA GACCTAAGCAACTTGCA GAGAT GCC   GG GGGGC

                            951                                             1000
Luciferase +CpG     (951)   GCCGCTCAGCAAGGAGGTAGGTGAGGCCGTGGCCAAACGCTTCCACCTAC
Luciferase CpG-     (951)   CCCTCTCAGCAAGGAGGTAGGTGAGGCTGTGGCCAAAAGGTTCCACCTAC
      Consensus     (951)    CC CTCAGCAAGGAGGTAGGTGAGGC GTGGCCAAA G TTCCACCTAC

                            1001                                            1050
Luciferase +CpG    (1001)   CAGGCATCCGCCAGGGCTACGGCCTGACAGAAACAACCAGCGCCATTCTG
Luciferase CpG-    (1001)   CAGGCATCAGGCAGGGCTATGGCCTGACAGAAACAACCTCTGCCATTCTG
      Consensus    (1001)   CAGGCATC G CAGGGCTA GGCCTGACAGAAACAACC   GCCATTCTG

                            1051                                            1100
Luciferase +CpG    (1051)   ATCACCCCCGAAGGGGACGACAAGCCTGGCGCAGTAGGCAAGGTGGTGCC
Luciferase CpG-    (1051)   ATCACCCCTGAAGGGGATGACAAGCCTGGAGCAGTAGGCAAGGTGGTGCC
      Consensus    (1051)   ATCACCCC GAAGGGGA GACAAGCCTGG GCAGTAGGCAAGGTGGTGCC
```

FIG 13C

```
                           1101                                             1150
Luciferase +CpG   (1101)  CTTCTTCGAGGCTAAGGTGGTGGACTTGGACACCGGTAAGACACTGGGTG
Luciferase CpG-   (1101)  CTTCTTTGAGGCTAAGGTGGTGGACTTGGACACAGGTAAGACACTGGGTG
      Consensus   (1101)  CTTCTT GAGGCTAAGGTGGTGGACTTGGACAC GGTAAGACACTGGGTG

                           1151                                             1200
Luciferase +CpG   (1151)  TGAACCAGCGCGGCGAGCTGTGCGTCCGTGGCCCCATGATCATGAGCGGC
Luciferase CpG-   (1151)  TGAACCAGAGAGGAGAGCTGTGTGTCAGGGGCCCCATGATCATGTCTGGC
      Consensus   (1151)  TGAACCAG G GG GAGCTGTG GTC G GGCCCCATGATCATG   GGC

                           1201                                             1250
Luciferase +CpG   (1201)  TACGTTAACAACCCCGAGGCTACAAACGCTCTCATCGACAAGGACGGCTG
Luciferase CpG-   (1201)  TATGTTAACAACCCTGAGGCTACAAATGCTCTCATTGACAAGGATGGCTG
      Consensus   (1201)  TA GTTAACAACCC GAGGCTACAAA GCTCTCAT GACAAGGA GGCTG

                           1251                                             1300
Luciferase +CpG   (1251)  GCTGCACAGCGGCGACATCGCCTACTGGGACGAGGACGAGCACTTCTTCA
Luciferase CpG-   (1251)  GCTGCACTCTGGAGACATTGCCTACTGGGATGAGGATGAGCACTTCTTCA
      Consensus   (1251)  GCTGCAC   GG GACAT GCCTACTGGGA GAGGA GAGCACTTCTTCA

                           1301                                             1350
Luciferase +CpG   (1301)  TCGTGGACCGGCTGAAGAGCCTGATCAAATACAAGGGCTACCAGGTAGCC
Luciferase CpG-   (1301)  TTGTGGACAGGCTGAAGAGCCTGATCAAATACAAGGGCTACCAGGTAGCC
      Consensus   (1301)  T GTGGAC GGCTGAAGAGCCTGATCAAATACAAGGGCTACCAGGTAGCC

                           1351                                             1400
Luciferase +CpG   (1351)  CCAGCCGAACTGGAGAGCATCCTGCTGCAACACCCCAACATCTTCGACGC
Luciferase CpG-   (1351)  CCAGCTGAACTGGAGAGCATCCTGCTGCAACACCCCAACATCTTTGATGC
      Consensus   (1351)  CCAGC GAACTGGAGAGCATCCTGCTGCAACACCCCAACATCTT GA GC

                           1401                                             1450
Luciferase +CpG   (1401)  CGGGGTCGCCGGCCTGCCCGACGACGATGCCGGCGAGCTGCCCGCCGCAG
Luciferase CpG-   (1401)  TGGGGTGGCTGGCCTGCCTGATGATGATGCAGGAGAGCTGCCAGCAGCAG
      Consensus   (1401)   GGGGT GC GGCCTGCC GA GA GATGC GG GAGCTGCC GC GCAG

                           1451                                             1500
Luciferase +CpG   (1451)  TCGTCGTGCTGGAACACGGTAAAACCATGACCGAGAAGGAGATCGTGGAC
Luciferase CpG-   (1451)  TTGTGGTGCTGGAACATGGTAAAACCATGACAGAGAAGGAGATTGTGGAC
      Consensus   (1451)  T GT GTGCTGGAACA GGTAAAACCATGAC GAGAAGGAGAT GTGGAC
                           1501                                             1550
Luciferase +CpG   (1501)  TATGTGGCCAGCCAGGTTACAACCGCCAAGAAGCTGCGCGGTGGTGTTGT
Luciferase CpG-   (1501)  TATGTGGCCAGCCAGGTTACAACAGCCAAGAAGCTGAGAGGTGGTGTTGT
      Consensus   (1501)  TATGTGGCCAGCCAGGTTACAAC GCCAAGAAGCTG G GGTGGTGTTGT
                           1551                                             1600
Luciferase +CpG   (1551)  GTTCGTGGACGAGGTGCCTAAAGGACTGACCGGCAAGTTGGACGCCCGCA
Luciferase CpG-   (1551)  GTTTGTGGATGAGGTGCCTAAAGGACTGACAGGCAAGTTGGATGCCAGAA
      Consensus   (1551)  GTT GTGGA GAGGTGCCTAAAGGACTGAC GGCAAGTTGGA GCC G A
                           1601                                             1650
Luciferase +CpG   (1601)  AGATCCGCGAGATTCTCATTAAGGCCAAGAAGGGCGGCAAGATCGCCGTG
Luciferase CpG-   (1601)  AGATCAGAGAGATTCTCATTAAGGCCAAGAAGGGAGGCAAGATTGCTGTG
      Consensus   (1601)  AGATC G GAGATTCTCATTAAGGCCAAGAAGGG GGCAAGAT GC GTG
```

FIG 14A

```
                                              1                                      40
     pTJU28-ssCMV-S100A1+intron-CpG     (1)  GAATTCTTGGCCAGTCCCTCTCTGCGCGCTCGCTCGCTCA
          S100A1 hTnT intron 9 ANF 3'   (1)  ----------------------------------------
h TnnT cardiac Exons 9-10 intron 9      (1)  ----------------------------------------
                          Consensus     (1)

                                              41                                     80
     pTJU28-ssCMV-S100A1+intron-CpG    (41)  CTGAGGCCTGGATACCAAAGGTATCCAGACTCCTAGGCTT
          S100A1 hTnT intron 9 ANF 3'   (1)  ----------------------------------------
h TnnT cardiac Exons 9-10 intron 9      (1)  ----------------------------------------
                          Consensus    (41)

                                              81                                    120
     pTJU28-ssCMV-S100A1+intron-CpG    (81)  TGCCTAGGAGGCCTCAGTGAGCGAGCGAGCGCGCAGAGAG
          S100A1 hTnT intron 9 ANF 3'   (1)  ----------------------------------------
h TnnT cardiac Exons 9-10 intron 9      (1)  ----------------------------------------
                          Consensus    (81)

                                              121                                   160
     pTJU28-ssCMV-S100A1+intron-CpG   (121)  GGAGTGGCCAACTCCATCACTAGGGGTTCCTGCAGGAGTC
          S100A1 hTnT intron 9 ANF 3'   (1)  ----------------------------------------
h TnnT cardiac Exons 9-10 intron 9      (1)  ----------------------------------------
                          Consensus   (121)

                                              161                                   200
     pTJU28-ssCMV-S100A1+intron-CpG   (161)  AATGGGAAAAACCCATTGGAGCCAAGTACACTGACTCAAT
          S100A1 hTnT intron 9 ANF 3'   (1)  ----------------------------------------
h TnnT cardiac Exons 9-10 intron 9      (1)  ----------------------------------------
                          Consensus   (161)

                                              201                                   240
     pTJU28-ssCMV-S100A1+intron-CpG   (201)  AGGGACTTTCCATTGGGTTTTGCCCAGTACATAAGGTCAA
          S100A1 hTnT intron 9 ANF 3'   (1)  ----------------------------------------
h TnnT cardiac Exons 9-10 intron 9      (1)  ----------------------------------------
                          Consensus   (201)

                                              241                                   280
     pTJU28-ssCMV-S100A1+intron-CpG   (241)  TAGGGGGTGAGTCAACAGGAAAGTCCCATTGGAGCCAAGT
          S100A1 hTnT intron 9 ANF 3'   (1)  ----------------------------------------
h TnnT cardiac Exons 9-10 intron 9      (1)  ----------------------------------------
                          Consensus   (241)

                                              281                                   320
     pTJU28-ssCMV-S100A1+intron-CpG   (281)  ACATTGAGTCAATAGGGACTTTCCAATGGGTTTTGCCCAG
          S100A1 hTnT intron 9 ANF 3'   (1)  ----------------------------------------
h TnnT cardiac Exons 9-10 intron 9      (1)  ----------------------------------------
                          Consensus   (281)

                                              321                                   360
     pTJU28-ssCMV-S100A1+intron-CpG   (321)  TACATAAGGTCAATGGGAGGTAAGCCAATGGGTTTTTCCC
          S100A1 hTnT intron 9 ANF 3'   (1)  ----------------------------------------
h TnnT cardiac Exons 9-10 intron 9      (1)  ----------------------------------------
                          Consensus   (321)
```

FIG 14B

```
                                       361                                    400
   pTJU28-ssCMV-S100A1+intron-CpG (361) ATTACTGACATGTATACTGAGTCATTAGGGACTTTCCAAT
        S100A1 hTnT intron 9 ANF 3'   (1) ----------------------------------------
h TnnT cardiac Exons 9-10 intron 9   (1) ----------------------------------------
                          Consensus (361)

                                       401                                    440
   pTJU28-ssCMV-S100A1+intron-CpG (401) GGGTTTTGCCCAGTACATAAGGTCAATAGGGGTGAATCAA
        S100A1 hTnT intron 9 ANF 3'   (1) ----------------------------------------
h TnnT cardiac Exons 9-10 intron 9   (1) ----------------------------------------
                          Consensus (401)

                                       441                                    480
   pTJU28-ssCMV-S100A1+intron-CpG (441) CAGGAAAGTCCCATTGGAGCCAAGTACACTGAGTCAATAG
        S100A1 hTnT intron 9 ANF 3'   (1) ----------------------------------------
h TnnT cardiac Exons 9-10 intron 9   (1) ----------------------------------------
                          Consensus (441)

                                       481                                    520
   pTJU28-ssCMV-S100A1+intron-CpG (481) GGACTTTCCATTGGGTTTTGCCCAGTACAAAAGGTCAATA
        S100A1 hTnT intron 9 ANF 3'   (1) ----------------------------------------
h TnnT cardiac Exons 9-10 intron 9   (1) ----------------------------------------
                          Consensus (481)

                                       521                                    560
   pTJU28-ssCMV-S100A1+intron-CpG (521) GGGGGTGAGTCAATGGGTTTTTCCCATTATTGGCACATAC
        S100A1 hTnT intron 9 ANF 3'   (1) ----------------------------------------
h TnnT cardiac Exons 9-10 intron 9   (1) ----------------------------------------
                          Consensus (521)

                                       561                                    600
   pTJU28-ssCMV-S100A1+intron-CpG (561) ATAAGGTCAATAGGGGTGACTAGTGGAGAAGAGCATGCTT
        S100A1 hTnT intron 9 ANF 3'   (1) ----------------------------------------
h TnnT cardiac Exons 9-10 intron 9   (1) ----------------------------------------
                          Consensus (561)

                                       601                                    640
   pTJU28-ssCMV-S100A1+intron-CpG (601) GAGGGCTGAGTGCCCCTCAGTGGGCAGAGAGCACATGGCC
        S100A1 hTnT intron 9 ANF 3'   (1) ----------------------------------------
h TnnT cardiac Exons 9-10 intron 9   (1) ----------------------------------------
                          Consensus (601)

                                       641                                    680
   pTJU28-ssCMV-S100A1+intron-CpG (641) CACAGTCCCTGAGAAGTTGGGGGGAGGGGTGGGCAATTGA
        S100A1 hTnT intron 9 ANF 3'   (1) ----------------------------------------
h TnnT cardiac Exons 9-10 intron 9   (1) ----------------------------------------
                          Consensus (641)
```

FIG 14C

```
                                                  681                                   720
     pTJU28-ssCMV-S100A1+intron-CpG    (681)  ACTGGTGCCTAGAGAAGGTGGGGCTTGGGTAAACTGGGAA
        S100A1 hTnT intron 9 ANF 3'      (1)  ----------------------------------------
h TnnT cardiac Exons 9-10 intron 9       (1)  ----------------------------------------
                          Consensus    (681)

                                              721                                   760
     pTJU28-ssCMV-S100A1+intron-CpG    (721)  AGTGATGTGGTGTACTGGCTCCACCTTTTTCCCCAGGGTG
        S100A1 hTnT intron 9 ANF 3'      (1)  ----------------------------------------
h TnnT cardiac Exons 9-10 intron 9       (1)  ----------------------------------------
                          Consensus    (721)

                                              761                                   800
     pTJU28-ssCMV-S100A1+intron-CpG    (761)  GGGGAGAACCATATATAAGTGCAGTAGTCTCTGTGAACAT
        S100A1 hTnT intron 9 ANF 3'      (1)  ----------------------------------------
h TnnT cardiac Exons 9-10 intron 9       (1)  ----------------------------------------
                          Consensus    (761)

                                              801                                   840
     pTJU28-ssCMV-S100A1+intron-CpG    (801)  TCAAGCTTCTGCCTTCTCCCTCCTGTGAGTTTGGTAAGTC
        S100A1 hTnT intron 9 ANF 3'      (1)  ----------------------------------------
h TnnT cardiac Exons 9-10 intron 9       (1)  ----------------------------------------
                          Consensus    (801)

                                              841                                   880
     pTJU28-ssCMV-S100A1+intron-CpG    (841)  ACTGACTGTCTATGCCTGGGAAAGGGTGGGCAGGAGATGG
        S100A1 hTnT intron 9 ANF 3'      (1)  ----------------------------------------
h TnnT cardiac Exons 9-10 intron 9       (1)  ----------------------------------------
                          Consensus    (841)

                                              881                                   920
     pTJU28-ssCMV-S100A1+intron-CpG    (881)  GGCAGTGCAGGAAAAGTGGCACTATGAACCCTGCAGCCCT
        S100A1 hTnT intron 9 ANF 3'      (1)  ----------------------------------------
h TnnT cardiac Exons 9-10 intron 9       (1)  ----------------------------------------
                          Consensus    (881)

                                              921                                   960
     pTJU28-ssCMV-S100A1+intron-CpG    (921)  AGGAATGCATCTAGACAATTGTACTAACCTTCTTCTCTTT
        S100A1 hTnT intron 9 ANF 3'      (1)  ----------------------------------------
h TnnT cardiac Exons 9-10 intron 9       (1)  ----------------------------------------
                          Consensus    (921)

                                              961                                  1000
     pTJU28-ssCMV-S100A1+intron-CpG    (961)  CCTCTCCTGACAGGTTGGTGTACAGTAGCTTCCACCATGG
        S100A1 hTnT intron 9 ANF 3'      (1)  ------------GAAATCTGTACAGTAGCTTCCACCATGG
h TnnT cardiac Exons 9-10 intron 9       (1)  ----------------------------------------
                          Consensus    (961)              G  T  TGTACAGTAGCTTCCACCATGG

                                              1001                                 1040
     pTJU28-ssCMV-S100A1+intron-CpG   (1001)  GCTCTGAGCTGGAGACAGCTATGGAGACCCTGATCAATGT
        S100A1 hTnT intron 9 ANF 3'     (29)  GCTCTGAGCTGGAGACAGCTATGGAGACCCTGATCAATGT
h TnnT cardiac Exons 9-10 intron 9       (1)  -----------------------GAGAAGGCCAAGGAGCT
                          Consensus   (1001)  GCTCTGAGCTGGAGACAGCTATGGAGACCCTGATCAATGT
```

FIG 14D

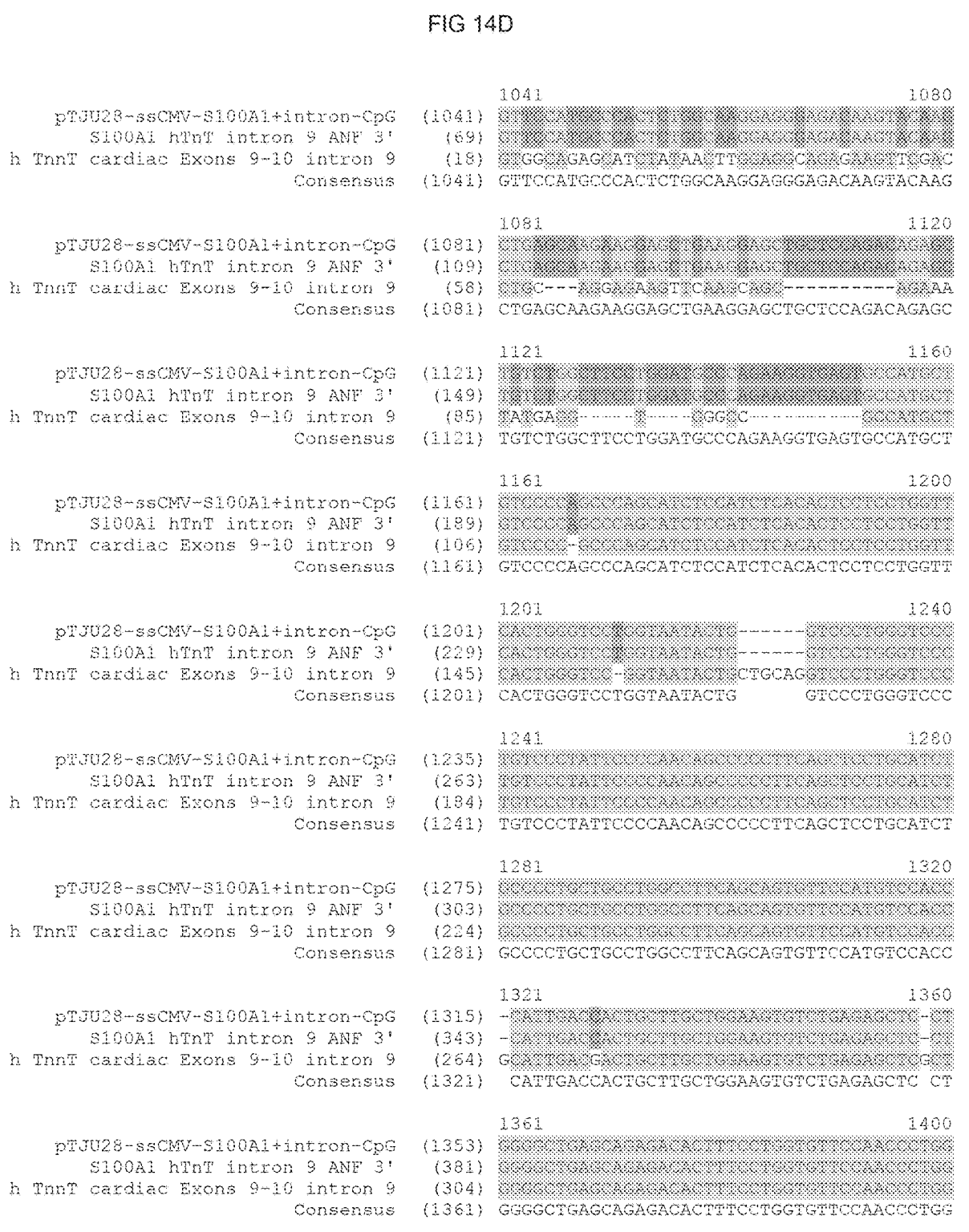

```
                                                1041                                   1080
pTJU28-ssCMV-S100A1+intron-CpG   (1041) [illegible]
   S100A1 hTnT intron 9 ANF 3'     (69) [illegible]
h TnnT cardiac Exons 9-10 intron 9 (18) [illegible]
                         Consensus (1041) GTTCCATGCCCACTCTGGCAAGGAGGGAGACAAGTACAAG

                                                1081                                   1120
pTJU28-ssCMV-S100A1+intron-CpG   (1081) [illegible]
   S100A1 hTnT intron 9 ANF 3'    (109) [illegible]
h TnnT cardiac Exons 9-10 intron 9 (58) [illegible]
                         Consensus (1081) CTGAGCAAGAAGGAGCTGAAGGAGCTGCTCCAGACAGAGC

                                                1121                                   1160
pTJU28-ssCMV-S100A1+intron-CpG   (1121) [illegible]
   S100A1 hTnT intron 9 ANF 3'    (149) [illegible]
h TnnT cardiac Exons 9-10 intron 9 (85) [illegible]
                         Consensus (1121) TGTCTGGCTTCCTGGATGCCCAGAAGGTGAGTGCCATGCT

                                                1161                                   1200
pTJU28-ssCMV-S100A1+intron-CpG   (1161) [illegible]
   S100A1 hTnT intron 9 ANF 3'    (189) [illegible]
h TnnT cardiac Exons 9-10 intron 9 (106) [illegible]
                         Consensus (1161) GTCCCCAGCCCAGCATCTCCATCTCACACTCCTCCTGGTT

                                                1201                                   1240
pTJU28-ssCMV-S100A1+intron-CpG   (1201) [illegible]
   S100A1 hTnT intron 9 ANF 3'    (229) [illegible]
h TnnT cardiac Exons 9-10 intron 9 (145) [illegible]
                         Consensus (1201) CACTGGGTCCTGGTAATACTG      GTCCCTGGGTCCC

                                                1241                                   1280
pTJU28-ssCMV-S100A1+intron-CpG   (1235) [illegible]
   S100A1 hTnT intron 9 ANF 3'    (263) [illegible]
h TnnT cardiac Exons 9-10 intron 9 (184) [illegible]
                         Consensus (1241) TGTCCCTATTCCCCAACAGCCCCCTTCAGCTCCTGCATCT

                                                1281                                   1320
pTJU28-ssCMV-S100A1+intron-CpG   (1275) [illegible]
   S100A1 hTnT intron 9 ANF 3'    (303) [illegible]
h TnnT cardiac Exons 9-10 intron 9 (224) [illegible]
                         Consensus (1281) GCCCCTGCTGCCTGGCCTTCAGCAGTGTTCCATGTCCACC

                                                1321                                   1360
pTJU28-ssCMV-S100A1+intron-CpG   (1315) [illegible]
   S100A1 hTnT intron 9 ANF 3'    (343) [illegible]
h TnnT cardiac Exons 9-10 intron 9 (264) [illegible]
                         Consensus (1321)  CATTGACCACTGCTTGCTGGAAGTGTCTGAGAGCTC CT

                                                1361                                   1400
pTJU28-ssCMV-S100A1+intron-CpG   (1353) [illegible]
   S100A1 hTnT intron 9 ANF 3'    (381) [illegible]
h TnnT cardiac Exons 9-10 intron 9 (304) [illegible]
                         Consensus (1361) GGGGCTGAGCAGAGACACTTTCCTGGTGTTCCAACCCTGG
```

FIG 14E

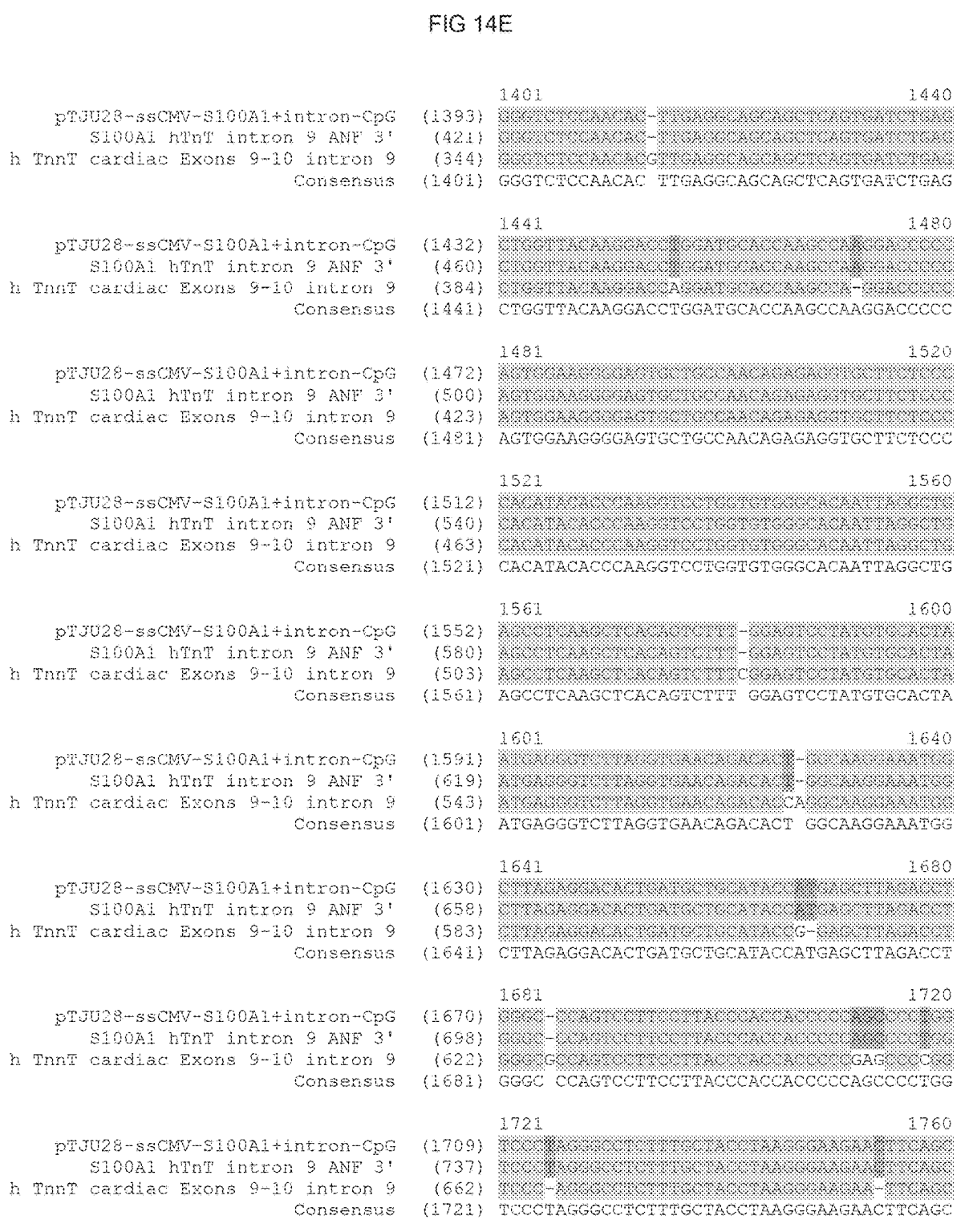

```
                                                  1401                                 1440
pTJU28-ssCMV-S100A1+intron-CpG       (1393)  [illegible]
    S100A1 hTnT intron 9 ANF 3'       (421)  [illegible]
h TnnT cardiac Exons 9-10 intron 9    (344)  [illegible]
                        Consensus    (1401)  GGGTCTCCAACAC TTGAGGCAGCAGCTCAGTGATCTGAG

                                                  1441                                 1480
pTJU28-ssCMV-S100A1+intron-CpG       (1432)  [illegible]
    S100A1 hTnT intron 9 ANF 3'       (460)  [illegible]
h TnnT cardiac Exons 9-10 intron 9    (384)  [illegible]
                        Consensus    (1441)  CTGGTTACAAGGACCTGGATGCACCAAGCCAAGGACCCCC

                                                  1481                                 1520
pTJU28-ssCMV-S100A1+intron-CpG       (1472)  [illegible]
    S100A1 hTnT intron 9 ANF 3'       (500)  [illegible]
h TnnT cardiac Exons 9-10 intron 9    (423)  [illegible]
                        Consensus    (1481)  AGTGGAAGGGGAGTGCTGCCAACAGAGAGGTGCTTCTCCC

                                                  1521                                 1560
pTJU28-ssCMV-S100A1+intron-CpG       (1512)  [illegible]
    S100A1 hTnT intron 9 ANF 3'       (540)  [illegible]
h TnnT cardiac Exons 9-10 intron 9    (463)  [illegible]
                        Consensus    (1521)  CACATACACCCAAGGTCCTGGTGTGGGCACAATTAGGCTG

                                                  1561                                 1600
pTJU28-ssCMV-S100A1+intron-CpG       (1552)  [illegible]
    S100A1 hTnT intron 9 ANF 3'       (580)  [illegible]
h TnnT cardiac Exons 9-10 intron 9    (503)  [illegible]
                        Consensus    (1561)  AGCCTCAAGCTCACAGTCTTT GGAGTCCTATGTGCACTA

                                                  1601                                 1640
pTJU28-ssCMV-S100A1+intron-CpG       (1591)  [illegible]
    S100A1 hTnT intron 9 ANF 3'       (619)  [illegible]
h TnnT cardiac Exons 9-10 intron 9    (543)  [illegible]
                        Consensus    (1601)  ATGAGGGTCTTAGGTGAACAGACACT GGCAAGGAAATGG

                                                  1641                                 1680
pTJU28-ssCMV-S100A1+intron-CpG       (1630)  [illegible]
    S100A1 hTnT intron 9 ANF 3'       (658)  [illegible]
h TnnT cardiac Exons 9-10 intron 9    (583)  [illegible]
                        Consensus    (1641)  CTTAGAGGACACTGATGCTGCATACCATGAGCTTAGACCT

                                                  1681                                 1720
pTJU28-ssCMV-S100A1+intron-CpG       (1670)  [illegible]
    S100A1 hTnT intron 9 ANF 3'       (698)  [illegible]
h TnnT cardiac Exons 9-10 intron 9    (622)  [illegible]
                        Consensus    (1681)  GGGC CCAGTCCTTCCTTACCCACCACCCCCAGCCCCTGG

                                                  1721                                 1760
pTJU28-ssCMV-S100A1+intron-CpG       (1709)  [illegible]
    S100A1 hTnT intron 9 ANF 3'       (737)  [illegible]
h TnnT cardiac Exons 9-10 intron 9    (662)  [illegible]
                        Consensus    (1721)  TCCCTAGGGCCTCTTTGCTACCTAAGGGAAGAACTTCAGC
```

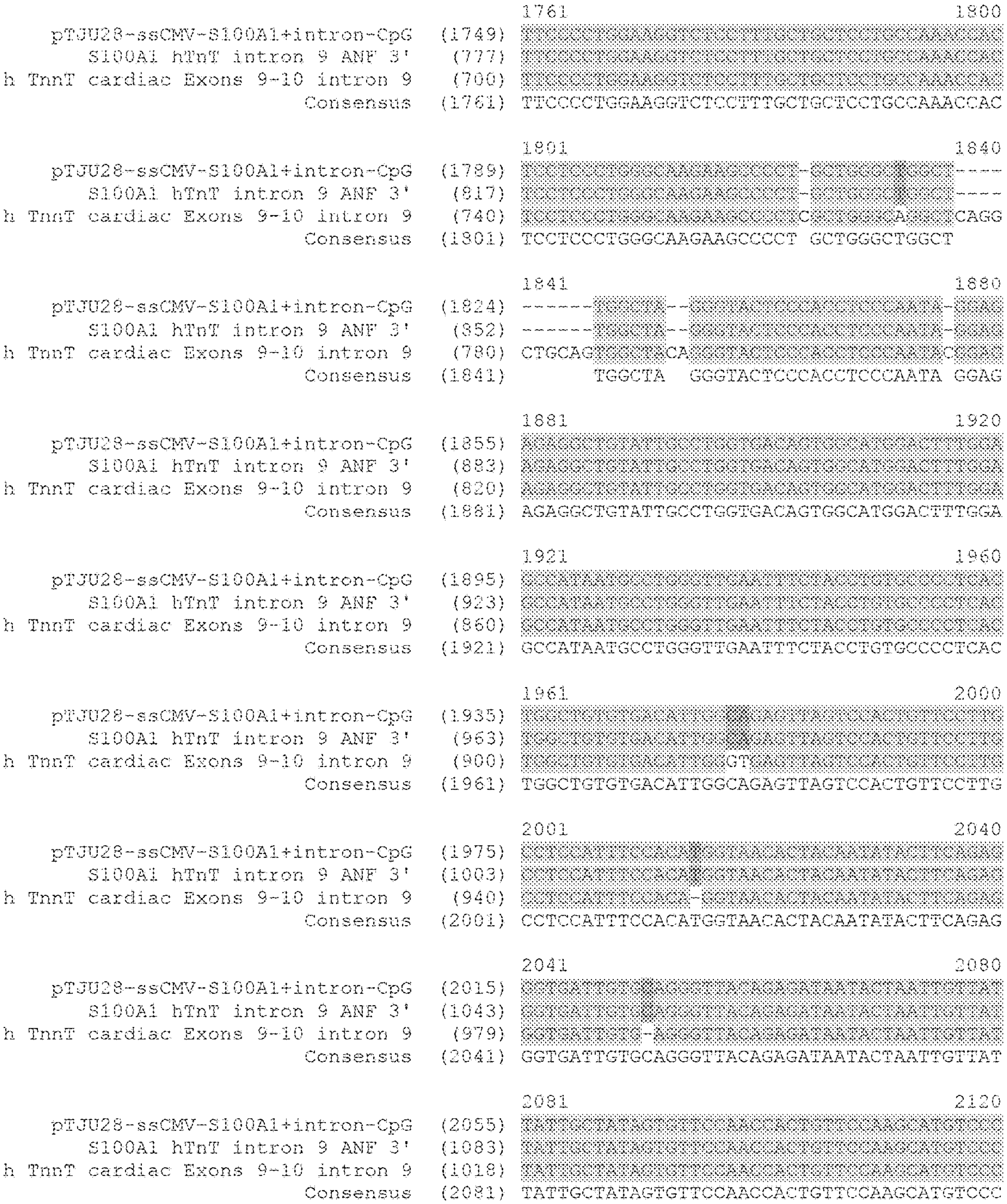

FIG 14F

```
                                              1761                                    1800
pTJU28-ssCMV-S100A1+intron-CpG  (1749)
         S100A1 hTnT intron 9 ANF 3'  (777)
h TnnT cardiac Exons 9-10 intron 9  (700)
                       Consensus  (1761) TTCCCTGGAAGGTCTCCTTTGCTGCTCCTGCCAAACCAC

                                              1801                                    1840
pTJU28-ssCMV-S100A1+intron-CpG  (1789)
         S100A1 hTnT intron 9 ANF 3'  (817)
h TnnT cardiac Exons 9-10 intron 9  (740)
                       Consensus  (1801) TCCTCCCTGGGCAAGAAGCCCCT GCTGGGCTGGCT

                                              1841                                    1880
pTJU28-ssCMV-S100A1+intron-CpG  (1824)
         S100A1 hTnT intron 9 ANF 3'  (852)
h TnnT cardiac Exons 9-10 intron 9  (780) CTGCAG
                       Consensus  (1841)       TGGCTA   GGGTACTCCCACCTCCCAATA GGAG

                                              1881                                    1920
pTJU28-ssCMV-S100A1+intron-CpG  (1855)
         S100A1 hTnT intron 9 ANF 3'  (883)
h TnnT cardiac Exons 9-10 intron 9  (820)
                       Consensus  (1881) AGAGGCTGTATTGCCTGGTGACAGTGGCATGGACTTTGGA

                                              1921                                    1960
pTJU28-ssCMV-S100A1+intron-CpG  (1895)
         S100A1 hTnT intron 9 ANF 3'  (923)
h TnnT cardiac Exons 9-10 intron 9  (860)
                       Consensus  (1921) GCCATAATGCCTGGGTTGAATTTCTACCTGTGCCCCTCAC

                                              1961                                    2000
pTJU28-ssCMV-S100A1+intron-CpG  (1935)
         S100A1 hTnT intron 9 ANF 3'  (963)
h TnnT cardiac Exons 9-10 intron 9  (900)
                       Consensus  (1961) TGGCTGTGTGACATTGGCAGAGTTAGTCCACTGTTCCTTG

                                              2001                                    2040
pTJU28-ssCMV-S100A1+intron-CpG  (1975)
         S100A1 hTnT intron 9 ANF 3'  (1003)
h TnnT cardiac Exons 9-10 intron 9  (940)
                       Consensus  (2001) CCTCCATTTCCACATGGTAACACTACAATATACTTCAGAG

                                              2041                                    2080
pTJU28-ssCMV-S100A1+intron-CpG  (2015)
         S100A1 hTnT intron 9 ANF 3'  (1043)
h TnnT cardiac Exons 9-10 intron 9  (979)
                       Consensus  (2041) GGTGATTGTGCAGGGTTACAGAGATAATACTAATTGTTAT

                                              2081                                    2120
pTJU28-ssCMV-S100A1+intron-CpG  (2055)
         S100A1 hTnT intron 9 ANF 3'  (1083)
h TnnT cardiac Exons 9-10 intron 9  (1018)
                       Consensus  (2081) TATTGCTATAGTGTTCCAACCACTGTTCCAAGCATGTCCC
```

FIG 14G

```
                                              2121                                  2160
 pTJU28-ssCMV-S100A1+intron-CpG    (2095)    ATGTATTAACTTACTATGCCCTCATAGCAGCCCTATGGGT
      S100A1 hTnT intron 9 ANF 3'  (1123)    ATGTATTAACTTACTATGCCCTCATAGCAGCCCTATGGGT
h TnnT cardiac Exons 9-10 intron 9 (1058)    ATGTATTAACTTACTATGCCCTCATAGCAGCCCTATGGGT
                         Consensus (2121)    ATGTATTAACTTACTATGCCCTCATAGCAGCCCTATGGGT

                                              2161                                  2200
 pTJU28-ssCMV-S100A1+intron-CpG    (2135)    TCATATCTGGGAAGGTGCTCAGAA--GAGCCTGGCACCCA
      S100A1 hTnT intron 9 ANF 3'  (1163)    TCATATCTGGGAAGGTGCTCAGAA--GAGCCTGGCACCCA
h TnnT cardiac Exons 9-10 intron 9 (1098)    TCATATCTGGGAAGGTGCTCAGGACAGAGCCTGGCACCCA
                         Consensus (2161)    TCATATCTGGGAAGGTGCTCAGAA  GAGCCTGGCACCCA

                                              2201                                  2240
 pTJU28-ssCMV-S100A1+intron-CpG    (2173)    CTAAATGCTCAGCA--TGTCAGCCATTGTTATGGCCTCTC
      S100A1 hTnT intron 9 ANF 3'  (1201)    CTAAATGCTCAGCA--TGTCAGCCATTGTTATGGCCTCTC
h TnnT cardiac Exons 9-10 intron 9 (1138)    CTAAATGCTCAGCAGGTGTCAGCCATTGTTATGGCCTCTC
                         Consensus (2201)    CTAAATGCTCAGCA  TGTCAGCCATTGTTATGGCCTCTC

                                              2241                                  2280
 pTJU28-ssCMV-S100A1+intron-CpG    (2211)    TAGTCCTGTGCCTTCCACTTTTTTCTCTTTTTTTGGTTCC
      S100A1 hTnT intron 9 ANF 3'  (1239)    TAGTCCTGTGCCTTCCACTTTTTTCTCTTTTTTTGGTTCC
h TnnT cardiac Exons 9-10 intron 9 (1178)    TAGTCCTGTGCCTTCCACTTTTTTCTCTTTTTTTGGTTCC
                         Consensus (2241)    TAGTCCTGTGCCTTCCACTTTTTTCTCTTTTTTTGGTTCC

                                              2281                                  2320
 pTJU28-ssCMV-S100A1+intron-CpG    (2251)    ACACTGAACTCTGCACCAAGCCAAAGGACACAGATTTGCC
      S100A1 hTnT intron 9 ANF 3'  (1279)    ACACTGAACTCTGCACCAAGCCAAAGGACACAGATTTGCC
h TnnT cardiac Exons 9-10 intron 9 (1218)    ACACTGAACTCTGCACCGGCCAACAAGGACACAGATTTGCC
                         Consensus (2281)    ACACTGAACTCTGCACCAAGCCAAAGGACACAGATTTGCC

                                              2321                                  2360
 pTJU28-ssCMV-S100A1+intron-CpG    (2291)    AAACTTTGGGGCAGCACCT-----GGGTGGTGCATGGGGA
      S100A1 hTnT intron 9 ANF 3'  (1319)    AAACTTTGGGGCAGCACCT-----GGGTGGTGCATGGGGA
h TnnT cardiac Exons 9-10 intron 9 (1258)    AAACTTTGGGGCAGCACCCTGCAGGGGTGGTGCATGGGGA
                         Consensus (2321)    AAACTTTGGGGCAGCACCT     GGGTGGTGCATGGGGA

                                              2361                                  2400
 pTJU28-ssCMV-S100A1+intron-CpG    (2326)    TGCTACTGCTCAAAGGGCACAGCTTCCTGGGATGGTGGGC
      S100A1 hTnT intron 9 ANF 3'  (1354)    TGCTACTGCTCAAAGGGCACAGCTTCCTGGGATGGTGGGC
h TnnT cardiac Exons 9-10 intron 9 (1298)    TGCTACTGCTCAAAGGGCACAGCTTCC-GGGATGGTGGGC
                         Consensus (2361)    TGCTACTGCTCAAAGGGCACAGCTTCCTGGGATGGTGGGC

                                              2401                                  2440
 pTJU28-ssCMV-S100A1+intron-CpG    (2366)    AGCTGGGCATGGGTGCCCCAGAGGGGTCTGGGGCTGGGCT
      S100A1 hTnT intron 9 ANF 3'  (1394)    AGCTGGGCATGGGTGCCCCAGAGGGGTCTGGGGCTGGGCT
h TnnT cardiac Exons 9-10 intron 9 (1337)    AGCTGGGCAGGGGTGCCCCAGAGGGGTCTGGGGCTGGGCT
                         Consensus (2401)    AGCTGGGCATGGGTGCCCCAGAGGGGTCTGGGGCTGGGCT

                                              2441                                  2480
 pTJU28-ssCMV-S100A1+intron-CpG    (2406)    GCTAGGAGGGCTCCATGACACAGCCTCCAGCTTTGTGCCC
      S100A1 hTnT intron 9 ANF 3'  (1434)    GCTAGGAGGGCTCCATGACACAGCCTCCAGCTTTGTGCCC
h TnnT cardiac Exons 9-10 intron 9 (1377)    GCTAGGAGGGCTCCATGACACAGCCTCCAGCTTTGTGCCC
                         Consensus (2441)    GCTAGGAGGGCTCCATGACACAGCCTCCAGCTTTGTGCCC
```

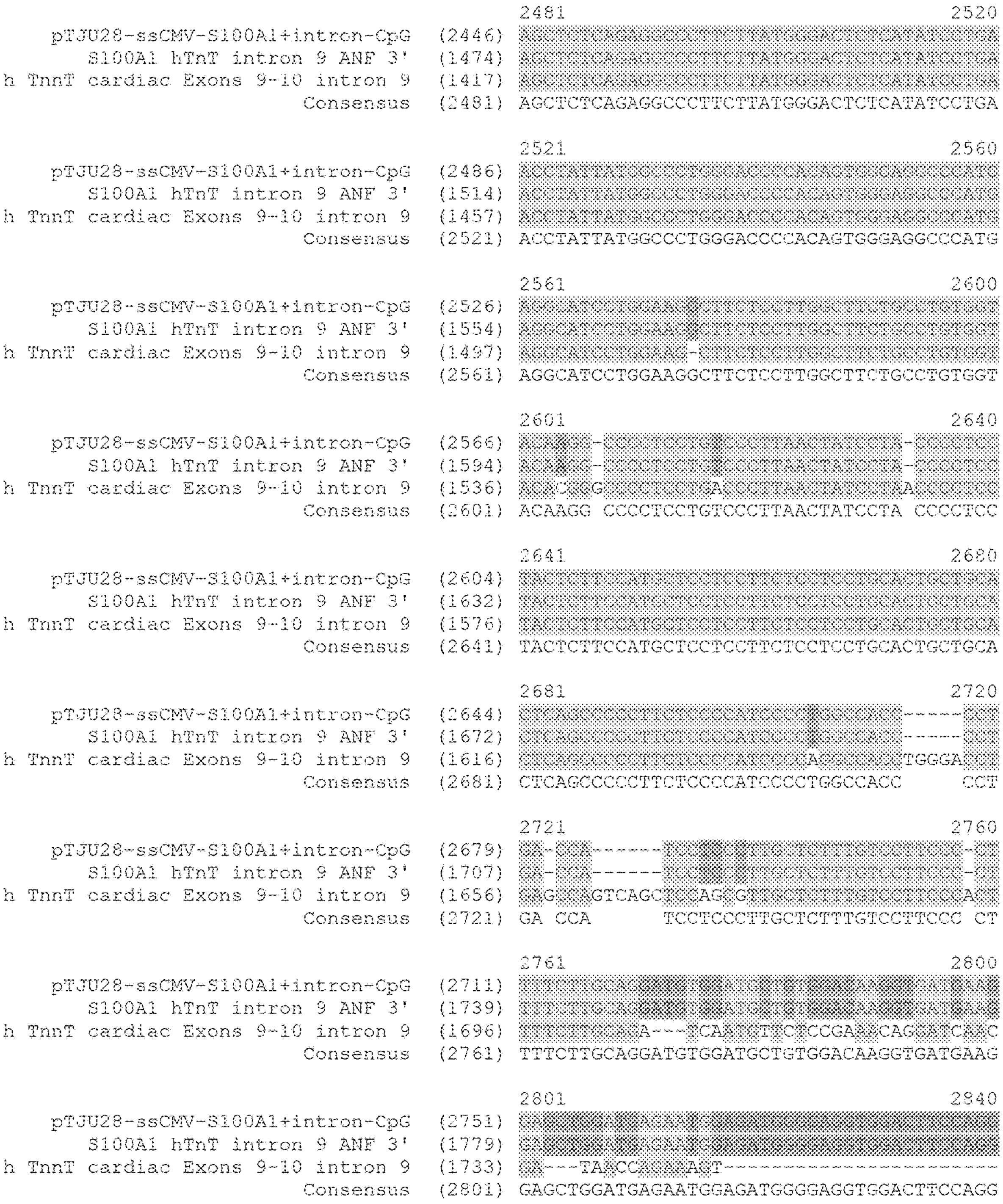

FIG 14H

```
                                        2481                         2520
pTJU28-ssCMV-S100A1+intron-CpG  (2446)
       S100A1 hTnT intron 9 ANF 3'  (1474)
h TnnT cardiac Exons 9-10 intron 9  (1417)
                     Consensus  (2481) AGCTCTCAGAGGCCCTTCTTATGGGACTCTCATATCCTGA

                                        2521                         2560
pTJU28-ssCMV-S100A1+intron-CpG  (2486)
       S100A1 hTnT intron 9 ANF 3'  (1514)
h TnnT cardiac Exons 9-10 intron 9  (1457)
                     Consensus  (2521) ACCTATTATGGCCCTGGGACCCCACAGTGGGAGGCCCATG

                                        2561                         2600
pTJU28-ssCMV-S100A1+intron-CpG  (2526)
       S100A1 hTnT intron 9 ANF 3'  (1554)
h TnnT cardiac Exons 9-10 intron 9  (1497)
                     Consensus  (2561) AGGCATCCTGGAAGGCTTCTCCTTGGCTTCTGCCTGTGGT

                                        2601                         2640
pTJU28-ssCMV-S100A1+intron-CpG  (2566)
       S100A1 hTnT intron 9 ANF 3'  (1594)
h TnnT cardiac Exons 9-10 intron 9  (1536)
                     Consensus  (2601) ACAAGG CCCCTCCTGTCCCTTAACTATCCTA CCCCTCC

                                        2641                         2680
pTJU28-ssCMV-S100A1+intron-CpG  (2604)
       S100A1 hTnT intron 9 ANF 3'  (1632)
h TnnT cardiac Exons 9-10 intron 9  (1576)
                     Consensus  (2641) TACTCTTCCATGCTCCTCCTTCTCCTCCTGCACTGCTGCA

                                        2681                         2720
pTJU28-ssCMV-S100A1+intron-CpG  (2644)
       S100A1 hTnT intron 9 ANF 3'  (1672)
h TnnT cardiac Exons 9-10 intron 9  (1616)
                     Consensus  (2681) CTCAGCCCCCTTCTCCCATCCCCTGGCCACC    CCT

                                        2721                         2760
pTJU28-ssCMV-S100A1+intron-CpG  (2679)
       S100A1 hTnT intron 9 ANF 3'  (1707)
h TnnT cardiac Exons 9-10 intron 9  (1656)
                     Consensus  (2721) GA CCA       TCCTCCCTTGCTCTTTGTCCTTCCC CT

                                        2761                         2800
pTJU28-ssCMV-S100A1+intron-CpG  (2711)
       S100A1 hTnT intron 9 ANF 3'  (1739)
h TnnT cardiac Exons 9-10 intron 9  (1696)
                     Consensus  (2761) TTTCTTGCAGGATGTGGATGCTGTGGACAAGGTGATGAAG

                                        2801                         2840
pTJU28-ssCMV-S100A1+intron-CpG  (2751)
       S100A1 hTnT intron 9 ANF 3'  (1779)
h TnnT cardiac Exons 9-10 intron 9  (1733)
                     Consensus  (2801) GAGCTGGATGAGAATGGAGATGGGGAGGTGGACTTCCAGG
```

FIG 14I

```
                                           2841                                   2880
    pTJU28-ssCMV-S100A1+intron-CpG  (2791)
         S100A1 hTnT intron 9 ANF 3'  (1819)
h TnnT cardiac Exons 9-10 intron 9  (1747) ----------------------------------------
                          Consensus  (2841) AGTATGTGGTGCTGGTGGCTGCCCTGACAGTGGCCTGCAA

                                           2881                                   2920
    pTJU28-ssCMV-S100A1+intron-CpG  (2831)
         S100A1 hTnT intron 9 ANF 3'  (1859)
h TnnT cardiac Exons 9-10 intron 9  (1747) ----------------------------------------
                          Consensus  (2881) CAACTTCTTCTGGGAGAACAGCTGAAGATAACAGCCAGGG

                                           2921                                   2960
    pTJU28-ssCMV-S100A1+intron-CpG  (2871)
         S100A1 hTnT intron 9 ANF 3'  (1899)
h TnnT cardiac Exons 9-10 intron 9  (1747) ----------------------------------------
                          Consensus  (2921) AGGACAAGCAGGGCTGGGCCTAGGGACAGACTGCAAGAGG

                                           2961                                   3000
    pTJU28-ssCMV-S100A1+intron-CpG  (2911)
         S100A1 hTnT intron 9 ANF 3'  (1939)
h TnnT cardiac Exons 9-10 intron 9  (1747) ----------------------------------------
                          Consensus  (2961) CTCCTGTCCCCTGGGGTCTCTGCTGCATTTGTGTCATCTT

                                           3001                                   3040
    pTJU28-ssCMV-S100A1+intron-CpG  (2951)
         S100A1 hTnT intron 9 ANF 3'  (1979)
h TnnT cardiac Exons 9-10 intron 9  (1747) ----------------------------------------
                          Consensus  (3001) GTTGATGGAGTTGTGATCATCCCATCTAAGCTAGCTTCCT

                                           3041                                   3080
    pTJU28-ssCMV-S100A1+intron-CpG  (2991)
         S100A1 hTnT intron 9 ANF 3'  (2019)
h TnnT cardiac Exons 9-10 intron 9  (1747) ----------------------------------------
                          Consensus  (3041) GTCAACACTTCTCACATCTTATGCTAACTGTAGATAAAGT

                                           3081                                   3120
    pTJU28-ssCMV-S100A1+intron-CpG  (3031)
         S100A1 hTnT intron 9 ANF 3'  (2059)
h TnnT cardiac Exons 9-10 intron 9  (1747) ----------------------------------------
                          Consensus  (3081) GGTTTGATGGTGACTTCCTCCTCTCCCACCCCATGCATTA

                                           3121                                   3160
    pTJU28-ssCMV-S100A1+intron-CpG  (3071)
         S100A1 hTnT intron 9 ANF 3'  (2099)
h TnnT cardiac Exons 9-10 intron 9  (1747) ----------------------------------------
                          Consensus  (3121) AATTTTAAGGTAGAACCTCACCTGTTACTGAAAGTGGTTT

                                           3161                                   3200
    pTJU28-ssCMV-S100A1+intron-CpG  (3111)
         S100A1 hTnT intron 9 ANF 3'  (2139)
h TnnT cardiac Exons 9-10 intron 9  (1747) ----------------------------------------
                          Consensus  (3161) GAAAGTGAATAAACTTCAGCACCATACAGAAGACAAATGC
```

FIG 14J

| | | |
|---|---|---|
| | | 3201 3240 |
| pTJU28-ssCMV-S100A1+intron-CpG | (3151) | [illegible] |
| S100A1 hTnT intron 9 ANF 3' | (2179) | [illegible] |
| h TnnT cardiac Exons 9-10 intron 9 | (1747) | ---------------------------------------- |
| Consensus | (3201) | CTGCTTGGTGTGCTTTCTTTCTTCTTGGGAAGATGGTCTG |
| | | 3241 3280 |
| pTJU28-ssCMV-S100A1+intron-CpG | (3191) | [illegible]CCTAGTGATGGAGTTGGCCACTC |
| S100A1 hTnT intron 9 ANF 3' | (2219) | [illegible]----------------------- |
| h TnnT cardiac Exons 9-10 intron 9 | (1747) | ---------------------------------------- |
| Consensus | (3241) | CTAGCTCTAGAGGATCC |
| | | 3281 3320 |
| pTJU28-ssCMV-S100A1+intron-CpG | (3231) | CCTCTCTGCGCGCTCGCTCGCTCACTGAGGCCTCCTAGGC |
| S100A1 hTnT intron 9 ANF 3' | (2236) | ---------------------------------------- |
| h TnnT cardiac Exons 9-10 intron 9 | (1747) | ---------------------------------------- |
| Consensus | (3281) | |
| | | 3321 3360 |
| pTJU28-ssCMV-S100A1+intron-CpG | (3271) | AAAGCCTAGGAGTCTGGATACCTTTGGTATCCAGGCCTCA |
| S100A1 hTnT intron 9 ANF 3' | (2236) | ---------------------------------------- |
| h TnnT cardiac Exons 9-10 intron 9 | (1747) | ---------------------------------------- |
| Consensus | (3321) | |
| | | 3361 3400 |
| pTJU28-ssCMV-S100A1+intron-CpG | (3311) | GTGAGCGAGCGAGCGCGCAGAGAGGGACTGGCCAAGCTTG |
| S100A1 hTnT intron 9 ANF 3' | (2236) | ---------------------------------------- |
| h TnnT cardiac Exons 9-10 intron 9 | (1747) | ---------------------------------------- |
| Consensus | (3361) | |
| | | 3401 3440 |
| pTJU28-ssCMV-S100A1+intron-CpG | (3351) | GCGTAATCATGGTCATAGCTGTTTCCTGTGTGAAATTGTT |
| S100A1 hTnT intron 9 ANF 3' | (2236) | ---------------------------------------- |
| h TnnT cardiac Exons 9-10 intron 9 | (1747) | ---------------------------------------- |
| Consensus | (3401) | |
| | | 3441 3480 |
| pTJU28-ssCMV-S100A1+intron-CpG | (3391) | ATCCGCTCACAATTCCACACAACATACGAGCCGGAAGCAT |
| S100A1 hTnT intron 9 ANF 3' | (2236) | ---------------------------------------- |
| h TnnT cardiac Exons 9-10 intron 9 | (1747) | ---------------------------------------- |
| Consensus | (3441) | |
| | | 3481 3520 |
| pTJU28-ssCMV-S100A1+intron-CpG | (3431) | AAAGTGTAAAGCCTGGGGTGCCTAATGAGTGAGCTAACTC |
| S100A1 hTnT intron 9 ANF 3' | (2236) | ---------------------------------------- |
| h TnnT cardiac Exons 9-10 intron 9 | (1747) | ---------------------------------------- |
| Consensus | (3481) | |
| | | 3521 3560 |
| pTJU28-ssCMV-S100A1+intron-CpG | (3471) | ACATTAATTGCGTTGCGCTCACTGCCCGCTTTCCAGTCGG |
| S100A1 hTnT intron 9 ANF 3' | (2236) | ---------------------------------------- |
| h TnnT cardiac Exons 9-10 intron 9 | (1747) | ---------------------------------------- |
| Consensus | (3521) | |

FIG 14K

```
                                                3561                                   3600
   pTJU28-ssCMV-S100A1+intron-CpG  (3511)  GAAACCTGTCGTGCCAGCTGCATTAATGAATCGGCCAACG
       S100A1 hTnT intron 9 ANF 3'  (2236)  ----------------------------------------
h TnnT cardiac Exons 9-10 intron 9  (1747)  ----------------------------------------
                         Consensus  (3561)

                                                3601                                   3640
   pTJU28-ssCMV-S100A1+intron-CpG  (3551)  CGCGGGGAGAGGCGGTTTGCGTATTGGGCGCTCTTCCGCT
       S100A1 hTnT intron 9 ANF 3'  (2236)  ----------------------------------------
h TnnT cardiac Exons 9-10 intron 9  (1747)  ----------------------------------------
                         Consensus  (3601)

                                                3641                                   3680
   pTJU28-ssCMV-S100A1+intron-CpG  (3591)  TCCTCGCTCACTGACTCGCTGCGCTCGGTCGTTCGGCTGC
       S100A1 hTnT intron 9 ANF 3'  (2236)  ----------------------------------------
h TnnT cardiac Exons 9-10 intron 9  (1747)  ----------------------------------------
                         Consensus  (3641)

                                                3681                                   3720
   pTJU28-ssCMV-S100A1+intron-CpG  (3631)  GGCGAGCGGTATCAGCTCACTCAAAGGCGGTAATACGGTT
       S100A1 hTnT intron 9 ANF 3'  (2236)  ----------------------------------------
h TnnT cardiac Exons 9-10 intron 9  (1747)  ----------------------------------------
                         Consensus  (3681)

                                                3721                                   3760
   pTJU28-ssCMV-S100A1+intron-CpG  (3671)  ATCCACAGAATCAGGGGATAACGCAGGAAAGAACATGTGA
       S100A1 hTnT intron 9 ANF 3'  (2236)  ----------------------------------------
h TnnT cardiac Exons 9-10 intron 9  (1747)  ----------------------------------------
                         Consensus  (3721)

                                                3761                                   3800
   pTJU28-ssCMV-S100A1+intron-CpG  (3711)  GCAAAAGGCCAGCAAAAGGCCAGGAACCGTAAAAAGGCCG
       S100A1 hTnT intron 9 ANF 3'  (2236)  ----------------------------------------
h TnnT cardiac Exons 9-10 intron 9  (1747)  ----------------------------------------
                         Consensus  (3761)

                                                3801                                   3840
   pTJU28-ssCMV-S100A1+intron-CpG  (3751)  CGTTGCTGGCGTTTTTCCATAGGCTCCGCCCCCCTGACGA
       S100A1 hTnT intron 9 ANF 3'  (2236)  ----------------------------------------
h TnnT cardiac Exons 9-10 intron 9  (1747)  ----------------------------------------
                         Consensus  (3801)

                                                3841                                   3880
   pTJU28-ssCMV-S100A1+intron-CpG  (3791)  GCATCACAAAAATCGACGCTCAAGTCAGAGGTGGCGAAAC
       S100A1 hTnT intron 9 ANF 3'  (2236)  ----------------------------------------
h TnnT cardiac Exons 9-10 intron 9  (1747)  ----------------------------------------
                         Consensus  (3841)

                                                3881                                   3920
   pTJU28-ssCMV-S100A1+intron-CpG  (3831)  CCGACAGGACTATAAAGATACCAGGCGTTTCCCCCTGGAA
       S100A1 hTnT intron 9 ANF 3'  (2236)  ----------------------------------------
h TnnT cardiac Exons 9-10 intron 9  (1747)  ----------------------------------------
                         Consensus  (3881)
```

FIG 14L

```
                                                3921                                    3960
 pTJU28-ssCMV-S100A1+intron-CpG  (3871) GCTCCCTCGTGCGCTCTCCTGTTCCGACCCTGCCGCTTAC
     S100A1 hTnT intron 9 ANF 3'  (2236) ----------------------------------------
h TnnT cardiac Exons 9-10 intron 9 (1747) ----------------------------------------
                        Consensus (3921)

                                                3961                                    4000
 pTJU28-ssCMV-S100A1+intron-CpG  (3911) CGGATACCTGTCCGCCTTTCTCCCTTCGGGAAGCGTGGCG
     S100A1 hTnT intron 9 ANF 3'  (2236) ----------------------------------------
h TnnT cardiac Exons 9-10 intron 9 (1747) ----------------------------------------
                        Consensus (3961)

                                                4001                                    4040
 pTJU28-ssCMV-S100A1+intron-CpG  (3951) CTTTCTCATAGCTCACGCTGTAGGTATCTCAGTTCGGTGT
     S100A1 hTnT intron 9 ANF 3'  (2236) ----------------------------------------
h TnnT cardiac Exons 9-10 intron 9 (1747) ----------------------------------------
                        Consensus (4001)

                                                4041                                    4080
 pTJU28-ssCMV-S100A1+intron-CpG  (3991) AGGTCGTTCGCTCCAAGCTGGGCTGTGTGCACGAACCCCC
     S100A1 hTnT intron 9 ANF 3'  (2236) ----------------------------------------
h TnnT cardiac Exons 9-10 intron 9 (1747) ----------------------------------------
                        Consensus (4041)

                                                4081                                    4120
 pTJU28-ssCMV-S100A1+intron-CpG  (4031) CGTTCAGCCCGACCGCTGCGCCTTATCCGGTAACTATCGT
     S100A1 hTnT intron 9 ANF 3'  (2236) ----------------------------------------
h TnnT cardiac Exons 9-10 intron 9 (1747) ----------------------------------------
                        Consensus (4081)

                                                4121                                    4160
 pTJU28-ssCMV-S100A1+intron-CpG  (4071) CTTGAGTCCAACCCGGTAAGACACGACTTATCGCCACTGG
     S100A1 hTnT intron 9 ANF 3'  (2236) ----------------------------------------
h TnnT cardiac Exons 9-10 intron 9 (1747) ----------------------------------------
                        Consensus (4121)

                                                4161                                    4200
 pTJU28-ssCMV-S100A1+intron-CpG  (4111) CAGCAGCCACTGGTAACAGGATTAGCAGAGCGAGGTATGT
     S100A1 hTnT intron 9 ANF 3'  (2236) ----------------------------------------
h TnnT cardiac Exons 9-10 intron 9 (1747) ----------------------------------------
                        Consensus (4161)

                                                4201                                    4240
 pTJU28-ssCMV-S100A1+intron-CpG  (4151) AGGCGGTGCTACAGAGTTCTTGAAGTGGTGGCCTAACTAC
     S100A1 hTnT intron 9 ANF 3'  (2236) ----------------------------------------
h TnnT cardiac Exons 9-10 intron 9 (1747) ----------------------------------------
                        Consensus (4201)

                                                4241                                    4280
 pTJU28-ssCMV-S100A1+intron-CpG  (4191) GGCTACACTAGAAGAACAGTATTTGGTATCTGCGCTCTGC
     S100A1 hTnT intron 9 ANF 3'  (2236) ----------------------------------------
h TnnT cardiac Exons 9-10 intron 9 (1747) ----------------------------------------
                        Consensus (4241)
```

FIG 14M

```
                                              4281                                   4320
   pTJU28-ssCMV-S100A1+intron-CpG   (4231)  TGAAGCCAGTTACCTTCGGAAAAAGAGTTGGTAGCTCTTG
       S100A1 hTnT intron 9 ANF 3'  (2236)  ----------------------------------------
h TnnT cardiac Exons 9-10 intron 9  (1747)  ----------------------------------------
                         Consensus  (4281)

                                              4321                                   4360
   pTJU28-ssCMV-S100A1+intron-CpG   (4271)  ATCCGGCAAACAAACCACCGCTGGTAGCGGTGGTTTTTTT
       S100A1 hTnT intron 9 ANF 3'  (2236)  ----------------------------------------
h TnnT cardiac Exons 9-10 intron 9  (1747)  ----------------------------------------
                         Consensus  (4321)

                                              4361                                   4400
   pTJU28-ssCMV-S100A1+intron-CpG   (4311)  GTTTGCAAGCAGCAGATTACGCGCAGAAAAAAAGGATCTC
       S100A1 hTnT intron 9 ANF 3'  (2236)  ----------------------------------------
h TnnT cardiac Exons 9-10 intron 9  (1747)  ----------------------------------------
                         Consensus  (4361)

                                              4401                                   4440
   pTJU28-ssCMV-S100A1+intron-CpG   (4351)  AAGAAGATCCTTTGATCTTTTCTACGGGGTCTGACGCTCA
       S100A1 hTnT intron 9 ANF 3'  (2236)  ----------------------------------------
h TnnT cardiac Exons 9-10 intron 9  (1747)  ----------------------------------------
                         Consensus  (4401)

                                              4441                                   4480
   pTJU28-ssCMV-S100A1+intron-CpG   (4391)  GTGGAACGAAAACTCACGTTAAGGGATTTTGGTCATGAGA
       S100A1 hTnT intron 9 ANF 3'  (2236)  ----------------------------------------
h TnnT cardiac Exons 9-10 intron 9  (1747)  ----------------------------------------
                         Consensus  (4441)

                                              4481                                   4520
   pTJU28-ssCMV-S100A1+intron-CpG   (4431)  TTATCAAAAAGGATCTTCACCTAGATCCTTTTAAATTAAA
       S100A1 hTnT intron 9 ANF 3'  (2236)  ----------------------------------------
h TnnT cardiac Exons 9-10 intron 9  (1747)  ----------------------------------------
                         Consensus  (4481)

                                              4521                                   4560
   pTJU28-ssCMV-S100A1+intron-CpG   (4471)  AATGAAGTTTTAAATCAATCTAAAGTATATATGAGTAAAC
       S100A1 hTnT intron 9 ANF 3'  (2236)  ----------------------------------------
h TnnT cardiac Exons 9-10 intron 9  (1747)  ----------------------------------------
                         Consensus  (4521)

                                              4561                                   4600
   pTJU28-ssCMV-S100A1+intron-CpG   (4511)  TTGGTCTGACAGTTACCAATGCTTAATCAGTGAGGCACCT
       S100A1 hTnT intron 9 ANF 3'  (2236)  ----------------------------------------
h TnnT cardiac Exons 9-10 intron 9  (1747)  ----------------------------------------
                         Consensus  (4561)

                                              4601                                   4640
   pTJU28-ssCMV-S100A1+intron-CpG   (4551)  ATCTCAGCGATCTGTCTATTTCGTTCATCCATAGTTGCCT
       S100A1 hTnT intron 9 ANF 3'  (2236)  ----------------------------------------
h TnnT cardiac Exons 9-10 intron 9  (1747)  ----------------------------------------
                         Consensus  (4601)
```

FIG 14N

```
                                           4641                                   4680
  pTJU28-ssCMV-S100A1+intron-CpG   (4591)  GACTCCCCGTCGTGTAGATAACTACGATACGGGAGGGCTT
      S100A1 hTnT intron 9 ANF 3'  (2236)  ----------------------------------------
h TnnT cardiac Exons 9-10 intron 9 (1747)  ----------------------------------------
                        Consensus  (4641)

                                           4681                                   4720
  pTJU28-ssCMV-S100A1+intron-CpG   (4631)  ACCATCTGGCCCCAGTGCTGCAATGATACCGCGAGACCCA
      S100A1 hTnT intron 9 ANF 3'  (2236)  ----------------------------------------
h TnnT cardiac Exons 9-10 intron 9 (1747)  ----------------------------------------
                        Consensus  (4681)

                                           4721                                   4760
  pTJU28-ssCMV-S100A1+intron-CpG   (4671)  CGCTCACCGGCTCCAGATTTATCAGCAATAAACCAGCCAG
      S100A1 hTnT intron 9 ANF 3'  (2236)  ----------------------------------------
h TnnT cardiac Exons 9-10 intron 9 (1747)  ----------------------------------------
                        Consensus  (4721)

                                           4761                                   4800
  pTJU28-ssCMV-S100A1+intron-CpG   (4711)  CCGGAAGGGCCGAGCGCAGAAGTGGTCCTGCAACTTTATC
      S100A1 hTnT intron 9 ANF 3'  (2236)  ----------------------------------------
h TnnT cardiac Exons 9-10 intron 9 (1747)  ----------------------------------------
                        Consensus  (4761)

                                           4801                                   4840
  pTJU28-ssCMV-S100A1+intron-CpG   (4751)  CGCCTCCATCCAGTCTATTAATTGTTGCCGGGAAGCTAGA
      S100A1 hTnT intron 9 ANF 3'  (2236)  ----------------------------------------
h TnnT cardiac Exons 9-10 intron 9 (1747)  ----------------------------------------
                        Consensus  (4801)

                                           4841                                   4880
  pTJU28-ssCMV-S100A1+intron-CpG   (4791)  GTAAGTAGTTCGCCAGTTAATAGTTTGCGCAACGTTGTTG
      S100A1 hTnT intron 9 ANF 3'  (2236)  ----------------------------------------
h TnnT cardiac Exons 9-10 intron 9 (1747)  ----------------------------------------
                        Consensus  (4841)

                                           4881                                   4920
  pTJU28-ssCMV-S100A1+intron-CpG   (4831)  CCATTGCTACAGGCATCGTGGTGTCACGCTCGTCGTTTGG
      S100A1 hTnT intron 9 ANF 3'  (2236)  ----------------------------------------
h TnnT cardiac Exons 9-10 intron 9 (1747)  ----------------------------------------
                        Consensus  (4881)

                                           4921                                   4960
  pTJU28-ssCMV-S100A1+intron-CpG   (4871)  TATGGCTTCATTCAGCTCCGGTTCCCAACGATCAAGGCGA
      S100A1 hTnT intron 9 ANF 3'  (2236)  ----------------------------------------
h TnnT cardiac Exons 9-10 intron 9 (1747)  ----------------------------------------
                        Consensus  (4921)

                                           4961                                   5000
  pTJU28-ssCMV-S100A1+intron-CpG   (4911)  GTTACATGATCCCCCATGTTGTGCAAAAAAGCGGTTAGCT
      S100A1 hTnT intron 9 ANF 3'  (2236)  ----------------------------------------
h TnnT cardiac Exons 9-10 intron 9 (1747)  ----------------------------------------
                        Consensus  (4961)
```

FIG 14O

```
                                                5001                                  5040
   pTJU28-ssCMV-S100A1+intron-CpG  (4951) CCTTCGGTCCTCCGATCGTTGTCAGAAGTAAGTTGGCCGC
        S100A1 hTnT intron 9 ANF 3'  (2236) ----------------------------------------
h TnnT cardiac Exons 9-10 intron 9  (1747) ----------------------------------------
                          Consensus  (5001)

                                                5041                                  5080
   pTJU28-ssCMV-S100A1+intron-CpG  (4991) AGTGTTATCACTCATGGTTATGGCAGCACTGCATAATTCT
        S100A1 hTnT intron 9 ANF 3'  (2236) ----------------------------------------
h TnnT cardiac Exons 9-10 intron 9  (1747) ----------------------------------------
                          Consensus  (5041)

                                                5081                                  5120
   pTJU28-ssCMV-S100A1+intron-CpG  (5031) CTTACTGTCATGCCATCCGTAAGATGCTTTTCTGTGACTG
        S100A1 hTnT intron 9 ANF 3'  (2236) ----------------------------------------
h TnnT cardiac Exons 9-10 intron 9  (1747) ----------------------------------------
                          Consensus  (5081)

                                                5121                                  5160
   pTJU28-ssCMV-S100A1+intron-CpG  (5071) GTGAGTACTCAACCAAGTCATTCTGAGAATAGTGTATGCG
        S100A1 hTnT intron 9 ANF 3'  (2236) ----------------------------------------
h TnnT cardiac Exons 9-10 intron 9  (1747) ----------------------------------------
                          Consensus  (5121)

                                                5161                                  5200
   pTJU28-ssCMV-S100A1+intron-CpG  (5111) GCGACCGAGTTGCTCTTGCCCGGCGTCAATACGGGATAAT
        S100A1 hTnT intron 9 ANF 3'  (2236) ----------------------------------------
h TnnT cardiac Exons 9-10 intron 9  (1747) ----------------------------------------
                          Consensus  (5161)

                                                5201                                  5240
   pTJU28-ssCMV-S100A1+intron-CpG  (5151) ACCGCGCCACATAGCAGAACTTTAAAAGTGCTCATCATTG
        S100A1 hTnT intron 9 ANF 3'  (2236) ----------------------------------------
h TnnT cardiac Exons 9-10 intron 9  (1747) ----------------------------------------
                          Consensus  (5201)

                                                5241                                  5280
   pTJU28-ssCMV-S100A1+intron-CpG  (5191) GAAAACGTTCTTCGGGGCGAAAACTCTCAAGGATCTTACC
        S100A1 hTnT intron 9 ANF 3'  (2236) ----------------------------------------
h TnnT cardiac Exons 9-10 intron 9  (1747) ----------------------------------------
                          Consensus  (5241)

                                                5281                                  5320
   pTJU28-ssCMV-S100A1+intron-CpG  (5231) GCTGTTGAGATCCAGTTCGATGTAACCCACTCGTGCACCC
        S100A1 hTnT intron 9 ANF 3'  (2236) ----------------------------------------
h TnnT cardiac Exons 9-10 intron 9  (1747) ----------------------------------------
                          Consensus  (5281)

                                                5321                                  5360
   pTJU28-ssCMV-S100A1+intron-CpG  (5271) AACTGATCTTCAGCATCTTTTACTTTCACCAGCGTTTCTG
        S100A1 hTnT intron 9 ANF 3'  (2236) ----------------------------------------
h TnnT cardiac Exons 9-10 intron 9  (1747) ----------------------------------------
                          Consensus  (5321)
```

FIG 14P

```
                                                 5361                                    5400
    pTJU28-ssCMV-S100A1+intron-CpG   (5311)  GGTGAGCAAAAACAGGAAGGCAAAATGCCGCAAAAAAGGG
       S100A1 hTnT intron 9 ANF 3'   (2236)  ----------------------------------------
h TnnT cardiac Exons 9-10 intron 9   (1747)  ----------------------------------------
                         Consensus   (5361)

                                                 5401                                    5440
    pTJU28-ssCMV-S100A1+intron-CpG   (5351)  AATAAGGGCGACACGGAAATGTTGAATACTCATACTCTTC
       S100A1 hTnT intron 9 ANF 3'   (2236)  ----------------------------------------
h TnnT cardiac Exons 9-10 intron 9   (1747)  ----------------------------------------
                         Consensus   (5401)

                                                 5441                                    5480
    pTJU28-ssCMV-S100A1+intron-CpG   (5391)  CTTTTTCAATATTATTGAAGCATTTATCAGGGTTATTGTC
       S100A1 hTnT intron 9 ANF 3'   (2236)  ----------------------------------------
h TnnT cardiac Exons 9-10 intron 9   (1747)  ----------------------------------------
                         Consensus   (5441)

                                                 5481                                    5520
    pTJU28-ssCMV-S100A1+intron-CpG   (5431)  TCATGAGCGGATACATATTTGAATGTATTTAGAAAAATAA
       S100A1 hTnT intron 9 ANF 3'   (2236)  ----------------------------------------
h TnnT cardiac Exons 9-10 intron 9   (1747)  ----------------------------------------
                         Consensus   (5481)

                                                 5521                                    5560
    pTJU28-ssCMV-S100A1+intron-CpG   (5471)  ACAAATAGGGGTTCCGCGCACATTTCCCCGAAAAGTGCCA
       S100A1 hTnT intron 9 ANF 3'   (2236)  ----------------------------------------
h TnnT cardiac Exons 9-10 intron 9   (1747)  ----------------------------------------
                         Consensus   (5521)

                                                 5561                                    5600
    pTJU28-ssCMV-S100A1+intron-CpG   (5511)  CCTGACGTCTAAGAAACCATTATTATCATGACATTAACCT
       S100A1 hTnT intron 9 ANF 3'   (2236)  ----------------------------------------
h TnnT cardiac Exons 9-10 intron 9   (1747)  ----------------------------------------
                         Consensus   (5561)

                                                 5601                                    5640
    pTJU28-ssCMV-S100A1+intron-CpG   (5551)  ATAAAAATAGGCGTATCACGAGGCCCTTTCGTCTCGCGCG
       S100A1 hTnT intron 9 ANF 3'   (2236)  ----------------------------------------
h TnnT cardiac Exons 9-10 intron 9   (1747)  ----------------------------------------
                         Consensus   (5601)

                                                 5641                                    5680
    pTJU28-ssCMV-S100A1+intron-CpG   (5591)  TTTCGGTGATGACGGTGAAAACCTCTGACACATGCAGCTC
       S100A1 hTnT intron 9 ANF 3'   (2236)  ----------------------------------------
h TnnT cardiac Exons 9-10 intron 9   (1747)  ----------------------------------------
                         Consensus   (5641)

                                                 5681                                    5720
    pTJU28-ssCMV-S100A1+intron-CpG   (5631)  CCGGAGACGGTCACAGCTTGTCTGTAAGCGGATGCCGGGA
       S100A1 hTnT intron 9 ANF 3'   (2236)  ----------------------------------------
h TnnT cardiac Exons 9-10 intron 9   (1747)  ----------------------------------------
                         Consensus   (5681)
```

FIG 14Q

```
                                                 5721                                   5760
     pTJU28-ssCMV-S100A1+intron-CpG  (5671)  GCAGACAAGCCCGTCAGGGCGCGTCAGCGGGTGTTGGCGG
       S100A1 hTnT intron 9 ANF 3'  (2236)  ----------------------------------------
h TnnT cardiac Exons 9-10 intron 9  (1747)  ----------------------------------------
                          Consensus  (5721)

                                                 5761                                   5800
     pTJU28-ssCMV-S100A1+intron-CpG  (5711)  GTGTCGGGGCTGGCTTAACTATGCGGCATCAGAGCAGATT
       S100A1 hTnT intron 9 ANF 3'  (2236)  ----------------------------------------
h TnnT cardiac Exons 9-10 intron 9  (1747)  ----------------------------------------
                          Consensus  (5761)

                                                 5801                                   5840
     pTJU28-ssCMV-S100A1+intron-CpG  (5751)  GTACTGAGAGTGCACCATATGCGGTGTGAAATACCGCACA
       S100A1 hTnT intron 9 ANF 3'  (2236)  ----------------------------------------
h TnnT cardiac Exons 9-10 intron 9  (1747)  ----------------------------------------
                          Consensus  (5801)

                                                 5841                                   5880
     pTJU28-ssCMV-S100A1+intron-CpG  (5791)  GATGCGTAAGGAGAAAATACCGCATCAGGCGCCATTCGCC
       S100A1 hTnT intron 9 ANF 3'  (2236)  ----------------------------------------
h TnnT cardiac Exons 9-10 intron 9  (1747)  ----------------------------------------
                          Consensus  (5841)

                                                 5881                                   5920
     pTJU28-ssCMV-S100A1+intron-CpG  (5831)  ATTCAGGCTGCGCAACTGTTGGGAAGGGCGATCGGTGCGG
       S100A1 hTnT intron 9 ANF 3'  (2236)  ----------------------------------------
h TnnT cardiac Exons 9-10 intron 9  (1747)  ----------------------------------------
                          Consensus  (5881)

                                                 5921                                   5960
     pTJU28-ssCMV-S100A1+intron-CpG  (5871)  GCCTCTTCGCTATTACGCCAGCTGGCGAAAGGGGGATGTG
       S100A1 hTnT intron 9 ANF 3'  (2236)  ----------------------------------------
h TnnT cardiac Exons 9-10 intron 9  (1747)  ----------------------------------------
                          Consensus  (5921)

                                                 5961                                   6000
     pTJU28-ssCMV-S100A1+intron-CpG  (5911)  CTGCAAGGCGATTAAGTTGGGTAACGCCAGGGTTTTCCCA
       S100A1 hTnT intron 9 ANF 3'  (2236)  ----------------------------------------
h TnnT cardiac Exons 9-10 intron 9  (1747)  ----------------------------------------
                          Consensus  (5961)

                                                 6001                       6028
     pTJU28-ssCMV-S100A1+intron-CpG  (5951)  GTCACGACGTTGTAAAACGACGGCCAGT
       S100A1 hTnT intron 9 ANF 3'  (2236)  ----------------------------
h TnnT cardiac Exons 9-10 intron 9  (1747)  ----------------------------
                          Consensus  (6001)
```

CONSTRUCTS AND METHODS FOR DELIVERING MOLECULES VIA VIRAL VECTORS WITH BLUNTED INNATE IMMUNE RESPONSES

CROSS REFERENCE TO RELATED APPLICATIONS

The present application is a Continuation Application of co-pending U.S. application Ser. No. 14/211,666, filed Mar. 14, 2014, which in turn claims priority from U.S. Provisional Application No. 61/785,368, filed Mar. 14, 2013. Applicants claim the benefits of 35 U.S.C. § 120 as to the U.S. application and priority under 35 U.S.C. § 119 as to the U.S. Provisional application, and the entire disclosure of each of which applications is incorporated herein by reference in its entirety.

STATEMENT OF FEDERALLY SPONSORED RESEARCH OR DEVELOPMENT

This invention was made with government support under grant numbers HL091096, HL007954 and AI007324 awarded by the National Institutes of Health (NIH). The government has certain rights in the invention.

BACKGROUND OF THE INVENTION

Adeno-associated virus (AAV) is a small, non-enveloped human parvovirus that packages a linear strand of single stranded DNA genome that is 4.7 kb. The capsid of an AAV contains 60 copies (in total) of three viral proteins (VPs), VP1, VP2, and VP3, in a predicted ratio of 1:1:10, arranged with T=1 icosahedral symmetry [H-J Nam, et al., *J Virol.*, 81(22): 12260-12271 (November 2007)]. The three VPs are translated from the same mRNA, with VP1 containing a unique N-terminal domain in addition to the entire VP2 sequence at its C-terminal region [Nam et al., cited above]. VP2 contains an extra N-terminal sequence in addition to VP3 at its C terminus. In X-ray crystal structures of the AAV2 [Q. Xie, et al., *Proc Natl. Acad. Sci. USA* 99:10405-10410 (2002)] and AAV4 [L. Govindasamy, et al., *J. Virol.*, 80:11556-11570] capsids and all other structures determined for parvovirus capsids, only the C-terminal polypeptide sequence in the AAV capsid proteins (~530 amino acids) is observed. The N-terminal unique region of VP1, the VP1-VP2 overlapping region, and the first 14 to 16 N-terminal residues of VP3 are disordered [L. Govindasamy, et al., and Q. Xie et al., cited above].

Productive infection by AAV occurs only in the presence of a helper virus, either adenovirus or herpes virus. In the absence of a helper virus, AAV integrates into a specific point of the host genome (19q 13-qter) at a high frequency, making AAV the only mammalian DNA virus known to be capable of site-specific integration. See, Kotin et at., 1990, PNAS, 87: 2211-2215. However, recombinant AAV, which does not contain any viral genes and only a therapeutic/marker expression cassette packaged in an AAV capsid, does not integrate into the genome. Instead the recombinant viral genome fuses at its ends via inverted terminal repeats to form circular, episomal forms characterized by long term gene expression.

The ability of AAV vectors to achieve long-term expression of the transgene product has been attributed to their relatively low immunogenicity. However, in some experimental settings, attendant immune responses have compromised the outcome of AAV-mediated gene therapy. How AAV activates the innate immune system remains unknown. In a study published by J. Zhu et al, J Clin Invest, Vol 119, No. 8 (August 2009), it is reported that the innate immune recognition of AAV2 by plasmacytoid dendric cells (DC) was mediated by TLR9 and dependent on MyD88. Activation of the TLR9-MyD88 pathway was independent of the nature of the transgene. Similarly, other serotypes of AAV, such as AAV1 and AAV9, also activated innate immunity through the TLR9-MyD88 pathway. The authors conclude that their observations suggest that strategies to block the TLR9-MyD88-type I IFN pathway may improve the clinical outcome of AAV-mediated gene therapy.

There have been attempts to modulate the innate immune response to AAV vectors, which approaches have involved various methods of disrupting the TLR9-MyD88-Type I IFN signaling pathway. One such approach is described by Y. Yang et al, US Published Patent Application No. 2011/0070241, published Mar. 24, 2011, which describes co-administration of an antagonist of this pathway with the viral vector. Another approach is described in Yew et al, US Published Patent Application No. 2012/0009222, published Jan. 12, 2012, which complexes lipidoids with polynucleotides such as CpG oligonucleotides, in an attempt to modulate innate immune responses. See, also, G. L. Rogers, et al, Frontiers in Microbiology, Vol. 2, Article 194 (September 2011), a review article which describes reducing vector load may be an alternative to artificially blocking the immune response with drugs. The authors of this paper also report on evidence that self-complementary (sc) AAV vectors induce a greater immune response than single-stranded (ss) AAV, indicating that there is some speculation this is perhaps due to a lack of stability of the viral capsid in scAAV vector. Rogers et al, further report that the vector cassette does not affect the response and that it is unlikely specific sequences in the DNA are responsible [Rogers et al, cited above, page 8, spanning columns 1 and 2] for the response.

The approaches taken to date to address the innate immune responses to AAV have focused on the AAV capsid. In addition to attempts to modulate Toll-like receptor 9 (TLR9) with short-term immunomodulators, e.g., TLR9 antagonists, attempts have been made to make modifications to the capsid, e.g., generating tyrosine mutant AAV capsids for AAV vectors to address these concerns.

What are needed in the art are constructs and methods for AAV-mediated gene delivery that induce reduced or no detectable innate immune responses.

SUMMARY OF THE INVENTION

In one aspect, an AAV vector having a CpG-reduced or CpG-depleted nucleic acid sequence packaged within an AAV capsid. Because the AAV vector is viral in origin and contains a capsid composed of proteins, no modification to the viral capsid is necessary. A CpG-modified AAV vector of the invention contains AAV inverted terminal repeat (ITR) sequences and an exogenous gene sequence under the control of regulatory sequences that control expression of the gene product. The nucleic acid sequences of one or more, and preferably all, of these elements are modified to reduce CpG di-nucleotides such that an immune response toward the vector and/or transgene is reduced as compared to the unmodified (aka wild type) AAV vector. Suitably, the AAV vector contains no other genomic AAV sequences.

In one embodiment, the transgene sequence contains a reduced number of CpG di-nucleotides as compared to the native coding sequence for the gene product. In another embodiment, the regulatory sequences are mutated to reduce or eliminate CpG di-nucleotides. In still another embodiment, the 5' and/or 3' terminal repeat sequences are mutated to reduce or eliminate native CpG di-nucleotides.

In another aspect, the invention provides a composition comprising a CpG-modified DNA vector as described herein and a pharmaceutically acceptable carrier.

In a further aspect, the invention provides a method for improving adeno-associated virus (AAV)-mediated gene expression by generating an AAV viral particle comprising a modified packaging insert, wherein said packaging insert comprises a nucleic acid molecule comprising AAV inverted terminal repeats (ITRs) sequences or functional equivalents thereof, e.g., 5' AAV ITR and 3' AAV ITR (which ITRs may be independently selected from CpG-modified or wild-type ITRs and optionally CpG-modified self-complementary ITRs) and an exogenous gene sequence under the control of regulatory sequences which control expression of the gene product, wherein said sequences of said nucleic acid molecule are modified to reduce CpG di-nucleotides such that an immune response to the vector is reduced as compared to the unmodified AAV vector without significant reduction in expression of the gene product; and delivering the AAV to a subject intramuscularly.

In still another aspect, the invention provides a regimen for repeat administration of a gene product. The regimen comprises delivering to a subject an AAV vector having an AAV capsid having packaged therein a CpG-modified nucleic acid molecule carrying an exogenous gene sequence and delivering to the subject a second vector comprising the exogenous gene sequence.

Still other aspects and advantages of the invention will be apparent from the following detailed description of the invention.

BRIEF DESCRIPTION OF THE DRAWINGS

FIGS. 9B-9D provide a scattergram which illustrates the results of the study in the mice injected with the AAVrh32.33LacZCpG+ vectors (FIG. 9B), AAVrh32.33LacZCpG− vectors (FIG. 9C) as compared to naïve animals (FIG. 9D), and which charts the concentration of the βgal tetramer (PE-conjugated H-$2K^b$-ICPMYARV tetramer) versus the concentration CD8+ cells.

FIGS. 11A-11E provide the sequences of the wild-type (+CpG) [SEQ ID NO: 6] and CpG-depleted (−CpG) [SEQ ID NO: 7] LacZ coding sequence in an alignment which further provides a consensus sequence.

FIGS. 12A-12G provide the sequences of a CpG-modified human TnT intron with S1001exons (−CpG) [SEQ ID NO: 8] in an alignment with the wild-type sequence (+CpG) [SEQ ID NO: 8] and a consensus sequence.

FIGS. 13A-13C provide the sequences of the wild-type (+CpG) [SEQ ID NO: 10] and CpG-depleted (−CpG) firefly luciferase [SEQ ID NO: 11] coding sequence in an alignment which further provides a consensus sequence.

FIGS. 14A-14Q provide an alignment containing a CpG modified vector (pTJU28-ssCMV-S100A1+intron-CpG) with CpG depleted ITRs CMV-EF1-alpha enhancer/promoter S100A1 therapeutic transgene interrupted by a human troponin T intron 9 modified to be CpG (−) followed by an atrial natriuretic factor (ANF) 3'UTR and poly A+ modified to be CpG (−) [SEQ ID NO: 12] compared to the synthesized DNA fragment containing the S100A1+intron+ANF sequence [SEQ ID NO:13] then compared to the human troponin T intron 9 sequence [SEQ ID NO: 14].

DETAILED DESCRIPTION OF THE INVENTION

Figure 1:
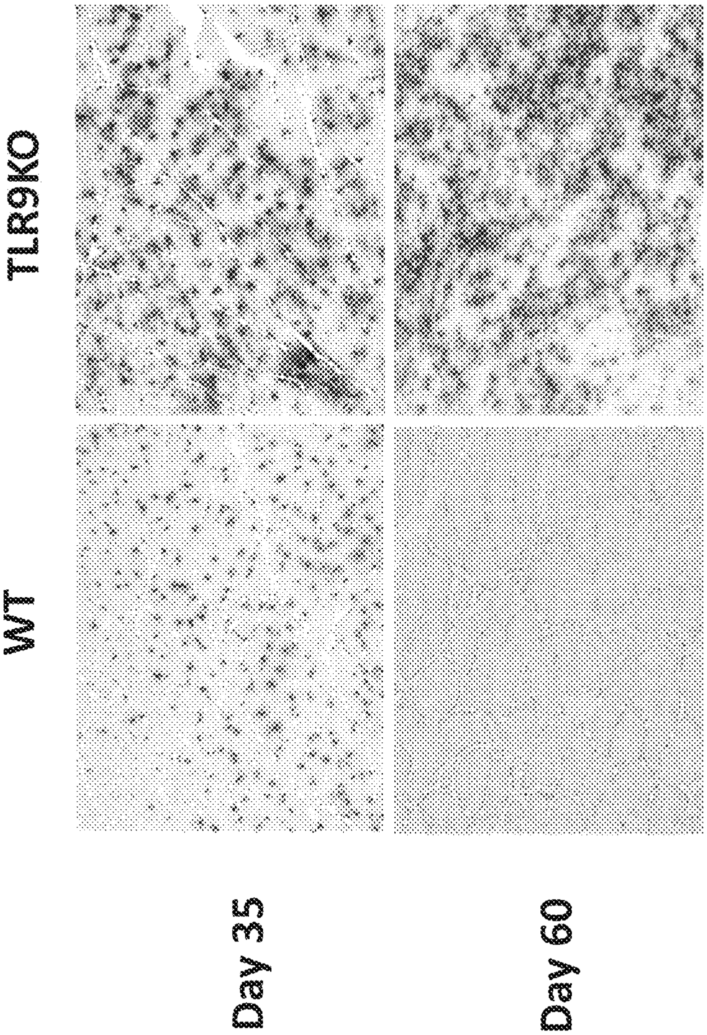
FIG. 1 provides representative sections of X-gal histochemical stain of muscle from wild-type (WT) and TLR9 knock-out (KO) mice injected intramuscularly (IM) with $1\times10^{11}$ genome copies (GC) of AAVrh32.33nLacZ (nuclear LacZ). 4 mice/group.

The present inventors have found that there is a reduction in immune response to a product expressed from a nucleic acid molecule expression cassette carried by an AAV vector in which the expression cassette has been CpG-modified to contain fewer CpG di-nucleotides. This contrasts with previous reports in the literature that AAV expression cassette sequences do not affect innate immune responses and this invention provides constructs and an approach which differs from that previously taken with AAV which involve a focus on the capsid involvement in the immune response.

A CpG-modified adeno-associated viral (AAV) vector is described herein. As used herein, a cytosine monophosphate (C) followed by a guanine monophosphate (G) in a nucleotide sequence is referred to as a CpG dinucleotide. In eukaryotes, the cytosine residues of CpG dinucleotides are often methylated to 5-methyl-cytosine ($^{m}$CpG). In bacterial genomes, CpG dinucleotides are typically unmethylated. As used throughout this specification, both methylated and unmethylated CpG are encompassed by the use of the term "CpG" or "CpG dinucleotide), unless methylated on unmethylated CpG is specified.

In one embodiment, an AAV vector is a viral particle having an AAV capsid in which a nucleic acid molecule is packaged. In one embodiment, the AAV vector lacks any functional AAV coding sequences, e.g., is deleted in AAV rep and cap coding sequences. Preferably, the rep and cap coding regions are entirely deleted. Alternatively, these regions are at least functionally deleted (i.e., incapable of producing rep or cap proteins). To the extent any portion of the coding sequences are retained in the AAV vector, they are CpG-depleted and, preferably, CpG-free. Suitably, the nucleic acid molecule contains sequences exogenous to the AAV capsid source, including a nucleic acid sequence which encodes a desired product for delivery to a selected host cell and regulatory sequences which direct expression thereof. The nucleic acid molecule also contains two AAV ITRs, located 5' and 3' to the coding sequences, or functional equivalents to these AAV ITRs. These AAV ITRs may be from the same source as the capsid, or may be from a different AAV from the capsid which permits replication of the expression cassette and packaging into the viral particle. Two AAV ITRs in a single vector may also be from different sources from each other. Where the AAV ITRs are from a different source than the AAV capsid, the resulting viral vector particle is termed a pseudotyped AAV.

As previously described, the present invention does not require any modifications to the AAV capsid or to the capsid coding sequence in the plasmid utilized for production of the AAV viral vector particle. Rather, it is the sequence carried within the AAV capsid which is modified to reduce CpG di-nucleotides such that the immune response is reduced following delivery of the vector as compared to the response generated by the unmodified AAV vector.

As used herein, the phrase "CpG− reduced" or "CpG-depleted" refers to a nucleic acid sequence which is generated, either synthetically or by mutation of a nucleic acid sequence, such that a majority of the CpG di-nucleotides are removed from the nucleic acid sequence. In some instances, all CpG motifs are removed to provide what is termed herein modified CpG-free sequences. The CpG motifs are suitably reduced or eliminated not just in a coding sequence (e.g., a transgene), but also in the non-coding sequences, including, e.g., 5' and 3' untranslated regions (UTRs), promoter, enhancer, polyA, ITRs, introns, and any other sequences present in the nucleic acid molecule. For the coding sequence, the DNA (5' to 3' direction) and codon triplets must be modified as well as the interface between triplets.

For example, CpG di-nucleotides may be located within a codon triplet for a selected amino acid. In one embodiment, the CpG di-nucleotides allocated within a codon triplet for a selected amino acid is changed to a codon triplet for the same amino acid lacking a CpG di-nucleotide.

| Amino Acid | DNA Triplets Containing CpG | DNA Triplets Lacking CpG |
|---|---|---|
| Serine (Ser or S) | TCG | TCT, TCC, TCA, AGT, AGC |
| Proline (Pro or P) | CCG | CCT, CCC, CCA, |
| Threonine (Thr or T) | ACG | ACA, ACT, ACC |
| Alanine (Ala or A) | GCG | GCT, GCC, GCA |
| Arginine (Arg or R) | CGT, CGC, CGA, CGG | AGA, AGG |
| Asparagine (Asn, N) | | AAT, AAC |
| Aspartic acid (Asp, D) | | GAT, GAC |
| Cysteine (Cys, C) | | TGT, TGC |
| Glutamic acid (Glu, E) | | GAA, GAG |
| Glutamine (Gln, Q) | | CAA, CAG |
| Glycine (Gly, G) | | GGT, GGC, GGA, GGG |
| Histidine (His, H) | | CAT, CAC |
| Isoleucine (Ile, I) | | ATT, ATC, ATA |
| Leucine (Leu, L) | | CTT, CTC, CTA, CTG, TTA, TTG |
| Lysine (Lys, K) | | AAA, AAG |
| Methionine (Met, M) | | ATG |

-continued

| Amino Acid | DNA Triplets Containing CpG | DNA Triplets Lacking CpG |
|---|---|---|
| Phenylalanine (Phe, F) | | TTT, TTC |
| stop | | TAA, TAG, TGA |
| Tryptophan (Trp, W) | | TGG |
| Tyrosine (Tyr, Y) | | TAT, TAC |
| Valine (Val, V) | | GTT, GTC, GTA, GTG |

In addition, within the coding region, the interface between triplets must be taken into consideration. For example, if an amino acid triplet ends in a C-nucleotide which is then followed by an amino acid triplet which can start only with a G-nucleotide (e.g., Valine, Glycine, Glutamic Acid, Alanine, Aspartic Acid), then the triplet for the first amino acid triplet is changed to one which does not end in a C-nucleotide. Illustrative CpG-depleted coding sequences are illustrated in FIG. 12 for LacZ and FIG. 13 for luciferase.

Similarly, non-coding sequences carried within the AAV capsid are also altered to be CpG-depleted and/or CpG-free.

Unless otherwise specified, the source of parental terminal repeats, AAV ITRs, and other selected AAV components described herein, may be readily selected from among any AAV, including, without limitation, AAV2, AAV7, AAV9 or another AAV sequences [e.g., US Published Patent Application No. 2011-0263027 A1; US Published Patent Application No. US-2011-0236353A1, U.S. Pat. No. 7,282,199B1; WO 03/042397 A1; WO 2005/033321; WO 2006/110689]. These parental ITRs or other AAV components may be readily isolated from an AAV sequence using techniques available to those of skill in the art of vector genome generation. Such parental AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like. These parental AAV sequences are the AAV nucleic acid sequences prior to CpG-depletion via synthetic methods or by site directed mutagenesis.

The wild-type ITRs from known AAV serotypes are CpG rich structures from which CpG dinucleotides are reduced according to the invention without significantly impairing the ability of the ITRs to bind rep protein in a packaging host cell, as required in order to package an expression cassette into an AAV viral vector. For example, the AAV2-5' and 3' wild-type ITRs consist of 32 total CpG dinucleotides (16 on each of the 5' and 3' ITR). As illustrated herein, these ITRs can each be reduced to 8 CpG dinucleotides and still generate AAV vectors which transduce mouse tissues. However, due to the location of the rep binding sequence on the AAV ITR, it has been found that these AAV2 ITRs may be difficult to modify due to the CpG-free sequence affecting the rep-binding function of the ITRs. Optionally, more CpG-dinucleotides may be reduced on the AAV2-3' ITR or the AAV2 5' ITRs, or combinations thereof, which do not affect rep binding and vector packaging. Alternatively, ITRs from other non-AAV2 sources may be selected which differ from AAV2 in the amount of CpG di-nucleotides and the location of these motifs vis-à-vis the rep binding sequence, such as to permit the 5' AAV ITR, the 3' AAV ITR, or both, to be rendered CpG-free according to the present invention. Similarly, modified ITRs, e.g., self-complementary ITR, or other sequences (e.g., parvovirus terminal repeats) which are functionally equivalent to AAV 5' ITRs and/or AAV 3' ITRs can also be CpG-depleted and used in the present invention.

In addition to the ITRs, other regulatory sequences are desirably CpG-depleted or rendered CpG-free according to the present invention. Such other regulatory sequences include a variety of elements including, e.g., without limitation, untranslated regions, promoter, enhancer, polyA, intron sequences, microRNAs and the like.

For example, the product encoded by the exogenous nucleic acid sequence is typically under the control of a promoter and/or promoter/enhancer sequence. Desirably, the CpG modifications to the promoters are made in a manner which does not affect the functional characteristics of the promoter and/or enhancer, e.g., without affecting tissue preference.

In an embodiment, where it may not be possible to remove all CpGs from a given nucleic molecule without negatively affecting a desired function, it may be desirable to concentrate on reducing clusters or concentrations of CpG di-nucleotides. For example, promoter regions have been described as natively containing clusters of CpG di-nucleotides and thus have been used in the development of algorithms which can predict whether removal of such CpG dinucleotides in this region will affect function in an unacceptable manner. Examples of such algorithms include, without limitation, those described in . . . . Y. A. Medvedeva, et al, "Algorithms for CpG Islands Search: New Advantages and Old Problems, in Bioinformatics—Trends and Methodologies", p. 449-472 (2011); M. Hackenburg, et al, "Prediction of CpG-island function: CpG clustering vs. sliding-window methods", BMC Genomics, 26 May 2010, 11:327. Synthetic promoter design strategies can be employed to aid in reducing CpG without altering tissue preference.

Similar methods and algorithms can be used to predict which CpG modifications may affect the function of a non-coding region. For other non-coding sequences, however, e.g., an intron, this type of prediction is not required. For example, for an intron, the CpG modifications may be performed so as to ensure that the altered nucleotides do not result in an unwanted coding sequence.

Thus, in one embodiment, an AAV vector of the invention contains within its capsid a nucleic acid sequence which contains a reduced number of CpG di-nucleotides as compared to the sequences for the native elements. In one embodiment, the number of CpG di-nucleotides in the nucleic acid molecule is reduced by at least about 25%, at least about 30%, at least about 45%, at least about 50%, at least about 75%, at least about 80%, at least about 85%, at least about 90%, at least about 95%, or about 95% to 97% CpG-depleted as compared to a nucleic acid molecule having the corresponding native sequences. One or more of the elements of the nucleic acid molecule carried by the AAV vector, e.g., without limitation, the gene coding sequence, a promoter, an enhancer, an intron, the 3' and 5' UTRs, may be CpG-free, i.e., lacking any CpG di-nucleotides.

In one embodiment, the immune response to the vector is reduced without significant reduction in expression of the gene product. More particularly, in certain instances, changing codons to remove CpG di-nucleotides may be result in less preferential codons being utilized for expression in a given type of host, resulting in lower expression levels of a transgene product. Suitably, codon triplets are selected such that the immune response is reduced while retaining expression levels at a therapeutically or immunologically desired level.

In one embodiment, the CpG-depleted AAV vector retains about 100%, at least about 95%, at least about 85%, at least about 80%, at least about 75% of the protein expression levels as compared to a nucleic acid molecule having the corresponding wild-type sequences, e.g., native ITRs, native exogenous gene sequence and other regulatory sequences. Depending upon the amount of reduction of immune response, a more significant reduction in expression level may be found to be acceptable in order to achieve the therapeutic or immunologic expression levels.

Although to this point the specification has focused on AAV vectors which are CpG-depleted, the approach described herein may be applied to other DNA vectors, and particularly viral vectors which are enveloped or which have capsid proteins. Such viral vectors may include those based on a double-stranded DNA virus, e.g., a virus selected from the group consisting of a baculovirus, poxvirus, herpesvirus or adenovirus, or a single-stranded DNA virus, e.g., another member of the parvovirus family of which AAV is a member.

The term "functional" refers to a product (e.g., a protein or peptide) which performs its native function, although not necessarily at the same level as the native product. The term "functional" may also refer to a gene which encodes a product and from which a desired product can be expressed. A "functional deletion" refers to a deletion which destroys the ability of the product to perform its native function.

Unless otherwise specified (as above), the term fragments includes peptides at least 8 amino acids in length, at least 15 amino acids in length, at least 25 amino acids in length. However, fragments of other desired lengths may be readily utilized depending upon the desired context. Such fragments may be produced recombinantly or by other suitable means, e.g., by chemical synthesis.

The term "percent (%) identity" may be readily determined for amino acid sequences, over the full-length of a protein, or a fragment thereof. Suitably, a fragment is at least about 8 amino acids in length, and may be up to about 700 amino acids. Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence.

When alignments are referenced, or when the CpG-modified sequences are compared to the sequences from the parental sequence prior to modification, conventional alignment techniques may be utilized. There are a number of algorithms known in the art that can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similarly, programs are available for performing amino acid alignments. Generally, these programs are used at default settings, although one skilled in the art can alter these settings as needed. Alternatively, one of skill in the art can utilize another algorithm or computer program that provides at least the level of identity or alignment as that provided by the referenced algorithms and programs.

Typically, when an alignment is prepared based upon an amino acid sequence (e.g., an AAV capsid protein), the alignment contains insertions and deletions which are so identified with respect to a reference AAV sequence (e.g., AAV2) and the numbering of the amino acid residues is based upon a reference scale provided for the alignment. However, any given AAV sequence may have fewer amino acid residues than the reference scale. In the present invention, when discussing the parental sequence, the term "the same position" or the "corresponding position" refers to the amino acid located at the same residue number in each of the sequences, with respect to the reference scale for the aligned sequences. However, when taken out of the alignment, each of the proteins may have these amino acids located at different residue numbers. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, *Nucl. Acids. Res.*, "A comprehensive comparison of multiple sequence alignments", 27(13):2682-2690 (1999).

As used throughout this specification and the claims, the terms "comprise" and "contain" and its variants including, "comprises", "comprising", "contains" and "containing", among other variants, is inclusive of other components, elements, integers, steps and the like. The term "consists of" or "consisting of" are exclusive of other components, elements, integers, steps and the like.

AAV Vectors with Expression Cassettes Having CpG–Mutations

CpG-depleted AAV vectors are described as are methods for generating these sequences. More particularly, the sequence of any of the vector elements described herein for CpG-depletion may be synthesized, generated via site-directed mutagenesis, or in some cases obtained commercially [e.g., CpG-free LacZ may be purchased from Invivogen (wild-type LacZ gene contains about 300 CpG di-nucleotides)]. The techniques by which these modifications are made is not a limitation on the present invention. Similarly, once the CpG-depleted sequences are obtained, an AAV vector may be produced using any suitable method.

As previously described, the present invention does not require modifications to the AAV capsid (protein sequence) or to the sequence used to produce same in a packaging host cell. A CpG-depleted AAV vector may be generated according to the invention utilizing any functional AAV capsid. In one embodiment, the capsid is provided by a single AAV source. Suitable AAVs may be selected from among, e.g., AAV2, AAV8, and AAVrh32.22. Still other AAVs may be readily selected from amongst those which have been described [US-2011-0263027A1; US-2011-0236353A1, U.S. Pat. No. 7,282,199B2; WO 03/042397 A1; WO 2005/033321; WO 2006/110689]. Alternatively, the AAV capsid may be derived from more than one AAV.

Optionally, modified AAV capsid may be utilized to generate a CpG-depleted vector of the invention. For example, an AAV capsid containing a heparin binding site may be modified to ablate the heparin binding motif, e.g., using methods such as those described in WO 2008/027084. Still other modifications to the wild-type AAV capsid may be made, e.g., to enhance production, yield and/or recovery of the capsid [see, e.g., US Published Patent Application 2009-0197338A1 describing "singleton" mutations] or an AAV vector having a chimeric or other artificial capsid protein. Other modifications include the modification(s) described in Yew et al, US Published Patent Application No. 2012/0009222, published Jan. 12, 2012.

In one aspect, the invention provides a method of generating a CpG-depleted adeno-associated virus (AAV) having an AAV capsid. Such a method involves culturing a host cell which contains a nucleic acid sequence encoding an AAV capsid; a functional rep gene; and a CpG-depleted expression cassette for packaging into the AAV vector. The components required to be cultured in the host cell to package a CpG-modified expression cassette in an AAV capsid may be provided to the host cell in trans. Alternatively, one or more of the required components (e.g., expression cassette, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The CpG-depleted expression cassette, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, *J. Virol.,* 70:520-532 (1993) and U.S. Pat. No. 5,478,745.

Unless otherwise specified, the source of parental (i.e., wild-type or unmodified) AAV ITRs, and other selected AAV components described herein, may be readily selected from among any AAV, including, those identified herein. These ITRs or other AAV components may be readily isolated using techniques available to those of skill in the art from an AAV sequence. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like. The AAV ITR and other expression cassette elements are CpG-depleted as described earlier in the specification.

While not repeated in each instance in the following description, it will be readily understood that each of the expression cassette elements may be CpG-depleted according to the present invention and optionally, one or more of these elements (e.g., the coding sequence) may be CpG-free.

A. The CpG-Depleted Expression Cassette

The CpG-depleted expression cassette is composed of, at a minimum, at least one copy of AAV inverted terminal repeat sequences, a transgene and its regulatory sequences. In one embodiment, both 5' AAV inverted terminal repeats (ITRs) and 3' ITRs are included in the expression cassette. In one desirable embodiment, the expression cassette contains ITRs from an AAV sequence other than those which provided AAV capsid sequences. For example, pseudotyped vectors containing both 5' and 3' CpG-modified AAV 2 ITRs may be used for convenience. However, a 5' ITR and/or a 3' ITR from other suitable AAVs may be selected and/or CpG-depleted as described herein. In another embodiment, functional equivalents to one or both of the 5' and 3' AAV ITRs may be utilized. Such functional equivalents function as origins of DNA replication and as packaging signals for the viral genome to allow packaging of the DNA molecule into the capsid to form a viral particle. For example, terminal repeats from another parvovirus may provide a functional equivalent and serve as the source of parental terminal repeats (TRs) for CpG-depletion. The CpG-modified expression cassette is packaged into a capsid protein and delivered to a selected host cell.

1. The Transgene

The transgene is a nucleic acid sequence, exogenous to the AAV sequences flanking the transgene and the source of the AAV capsid, which encodes a polypeptide, peptide, protein, enzyme, or other product of interest. In one embodiment, the expression cassette carries a nucleic acid sequence, e.g., an RNA. Desirable RNA molecules include tRNA, dsRNA, RNAi, ribosomal RNA, catalytic RNAs, siRNA, small hairpin RNA, trans-splicing RNA, and antisense RNAs. One example of a useful RNA sequence is a sequence which inhibits or extinguishes expression of a targeted nucleic acid sequence in the treated animal. Typically, suitable target sequences include oncologic targets and viral diseases. This may be useful, e.g., for cancer therapies and vaccines.

The nucleic acid coding sequence is suitably CpG-depleted as described herein and operatively linked to regulatory components in a manner which permits transgene transcription, translation, and/or expression in a host cell.

While any variety of products may be delivered using the constructs of the invention, the invention is particularly well suited for delivery of products useful in diagnosis, treatment, and vaccination of conditions associated with conducting airway cells and amelioration of the symptoms thereof.

2. Regulatory Elements

In addition to the major elements identified above for the expression cassette, the vector may also include conventional control elements which are CpG-depleted and which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [See, e.g., Boshart et al, *Cell,* 41:521-530 (1985)], the SV40 promoter, the dihydrofolate reductase promoter, the β-actin promoter, the phosphoglycerol kinase (PGK) promoter, and the elongation factor 1-alpha (EF1-alpha) promoter [Invitrogen]. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invivogen, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system [International Patent Publication No. WO 98/10088]; the ecdysone insect promoter [No et al, *Proc. Natl. Acad. Sci. USA,* 93:3346-3351 (1996)], the tetracycline-repressible system [Gossen et al, *Proc. Natl. Acad. Sci. USA,* 89:5547-5551 (1992)], the tetracycline-inducible system [Gossen et al, *Science,* 268:1766-1769 (1995), See also Harvey et al, *Curr. Opin. Chem. Biol.,* 2:512-518 (1998)], the RU486-inducible system [Wang et al, *Nat. Biotech.,* 15:239-243 (1997) and Wang et al, *Gene Ther.,* 4:432-441 (1997)] and the rapamycin-inducible system [Magari et al, *J. Clin. Invest.,* 100:2865-2872 (1997)]. Other types of inducible promoters which may be useful in this context are those which are regulated by a specific physiological state, e.g., temperature, acute phase, a particular differentiation state of the cell, or in replicating cells only.

In another embodiment, the native promoter for the transgene will be CpG-depleted and used. This promoter may be preferred when it is desired that expression of the transgene should mimic the native expression, or when expression of the transgene must be regulated temporally or developmentally, in a tissue-specific manner, or in response to specific transcriptional stimuli. In a further embodiment, other CpG-depleted expression control elements, such as enhancer elements, polyadenylation sites or Kozak consensus sequences may also be used to mimic the native expression.

Another embodiment of the transgene includes a CpG-depleted gene operably linked to a tissue-specific promoter. For example, promoters specific for pulmonary tissue and, where available, specific for conducting airway cells, may be used. Examples of such promoters may include, e.g., the forkhead box J1 (FOXJ1) promoter, polyubiquitin promoter UbC, SAM pointed domain-containing ETS transcription factor (SPDEF) promoter, Clara cell secretory protein/uteroglobin (CCSP/UG) promoter, amongst others.
Other lung-specific gene promoters may include, e.g., the surfactant protein B (SPB), surfactant protein C (SPC), and surfactant protein A (SPA), ectogenic human carcinoembryonic antigen (CEA) promoter, Thyroid transcription factor 1 (TTF1) and human surfactant protein A1 (hSPA1), amongst others.

Optionally, therapeutically useful transgenes may also include selectable markers or reporter genes that include sequences encoding geneticin, hygromicin or purimycin resistance, among others. Such selectable reporters or marker genes (preferably located outside the viral genome to be rescued by the method of the invention) can be used to signal the presence of the plasmids in bacterial cells, such as ampicillin resistance. Other components of the plasmid may include an origin of replication. Selection of these and other promoters and vector elements are conventional and many such sequences are available.

The combination of the transgene, promoter/enhancer, and AAV ITRs is referred to as an expression cassette for ease of reference herein. Having been provided with the teachings in this specification, the design of a CpG-depleted expression cassette can readily be made by one of skill in the art.

3. Delivery of the CpG-Depleted Expression Cassette to a Packaging Host Cell

The CpG-depleted expression cassette can be carried on any suitable vector, e.g., a plasmid, which is delivered to a packaging host cell. The plasmids useful in this invention may be engineered such that they are suitable for replication and, optionally, integration in prokaryotic cells, mammalian cells, or both. These plasmids (or other vectors carrying the 5' AAV ITR-exogenous molecule-3' AAV ITR) contain sequences permitting replication of the expression cassette in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components, permit high copy episomal replication in the cells. Preferably, the molecule carrying the expression cassette is transfected into the cell, where it may exist transiently. Alternatively, the expression cassette (carrying the 5' AAV ITR-heterologous molecule-3' ITR) may be stably integrated into the genome of the host cell, either chromosomally or as an episome. In certain embodiments, the expression cassette may be present in multiple copies, optionally in head-to-head, head-to-tail, or tail-to-tail concatamers. Suitable transfection techniques are known and may readily be utilized to deliver the expression cassette to the host cell.

Generally, when delivering the vector comprising the CpG-depleted expression cassette by transfection, the vector is delivered in an amount from about 5 μg to about 100 μg DNA, about 10 μg to about 50 μg DNA to about $1\times10^4$ cells to about $1\times10^{13}$ cells, or about $1\times10^5$ cells. However, the relative amounts of vector DNA to host cells may be adjusted by one of ordinary skill in the art, who may take into consideration such factors as the selected vector, the delivery method and the host cells selected.

B. Rep and Cap Sequences

In addition to the CpG-depleted expression cassette, the host cell contains the sequences which drive expression of an AAV capsid in the host cell and rep sequences of the same source as the source of the AAV ITRs found in the CpG-depleted expression cassette, or a cross-complementing source. The AAV cap and rep sequences may be independently obtained from an AAV source as described above and may be introduced into the host cell in any manner known to one in the art as described above. Additionally, when pseudotyping an AAV vector, the sequences encoding each of the essential rep proteins may be supplied by different AAV sources (e.g., AAV2, AAV8, AAV32/33, AAV5, AAV7, AAV8, AAV9, or one of the other AAV sequences described herein or known in the art). For example, the rep78/68 sequences may be from AAV2, whereas the rep52/40 sequences may be from AAV8.

The transcription units(s) in the replication-deficient rAAVs may be packaged with any AAV capsid protein (Cap) described herein, known in the art, or to be discovered. Caps from serotypes AAV1, AAV6, AAV7, AAV8, AAV9 or rh10 are particularly preferred for generating rAAVs for use in human subjects. In a preferred embodiment, an rAAV Cap is based on serotype AAV8. In another embodiment, an rAAV Cap is based on Caps from two or three or more AAV serotypes. For example, in one embodiment, an rAAV Cap is based on AAV6 and AAV9.

Any serotype of AAV known in the art, e.g., serotypes AAV1, AAV2, AAV3A, AAV3B, AAV4, AAV5, AAV6, AAV7 [see, WO 2003/042397], AAV8 [see, e.g., U.S. Pat. Nos. 7,790,449; 7,282,199], AAV9 [see, WO 2005/033321], AAV10, AAV11, AAV12, rh10, modified AAV [see, e.g., WO 2006/110689], or yet to be discovered, or a recombinant AAV based thereon, may be used as a source for the rAAV capsid.

In one embodiment, the host cell stably contains the capsid under the control of a suitable promoter, such as those described above. Most desirably, in this embodiment, the capsid is expressed under the control of an inducible promoter. In another embodiment, the capsid is supplied to the host cell in trans. When delivered to the host cell in trans, the capsid may be delivered via a plasmid that contains the sequences necessary to direct expression of the selected capsid in the host cell. Most desirably, when delivered to the host cell in trans, the plasmid carrying the capsid also carries other sequences required for packaging the rAAV, e.g., the rep sequences.

In another embodiment, the host cell stably contains the rep sequences under the control of a suitable promoter, such as those described above. Most desirably, in this embodiment, the essential rep proteins are expressed under the control of an inducible promoter. In another embodiment, the rep proteins are supplied to the host cell in trans. When delivered to the host cell in trans, the rep proteins may be delivered via a plasmid which contains the sequences necessary to direct expression of the selected rep proteins in the host cell.

Thus, in one embodiment, the rep and cap sequences may be transfected into the host cell on a single nucleic acid molecule and exist stably in the cell as an episome. In another embodiment, the rep and cap sequences are stably integrated into the chromosome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

Optionally, the rep and/or cap sequences may be supplied on a vector that contains other DNA sequences that are to be introduced into the host cells. For instance, the vector may contain the rAAV construct comprising the expression cassette. The vector may comprise one or more of the genes encoding the helper functions, e.g., the adenoviral proteins E1, E2a, and E4 ORF6, and the gene for VAI RNA.

Preferably, the promoter used in this construct may be any of the constitutive, inducible or native promoters known to one of skill in the art or as discussed above. In one embodiment, an AAV P5 promoter sequence is employed. The selection of the AAV to provide any of these sequences does not limit the invention.

In another embodiment, the promoter for rep is an inducible promoter, such as are discussed above in connection with the transgene regulatory elements. One preferred promoter for rep expression is the T7 promoter. The vector comprising the rep gene regulated by the T7 promoter and the cap gene, is transfected or transformed into a cell that either constitutively or inducibly expresses the T7 polymerase. See International Patent Publication No. WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or a coding sequence with transcriptional controls. Two exemplary sources of spacer sequences are the λ phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell. The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

In another embodiment of this invention, the rep or cap protein may be provided stably by a host cell.

C. The Helper Functions

The packaging host cell also requires helper functions in order to package the rAAV of the invention. Optionally, these functions may be supplied by a herpesvirus. Most desirably, the necessary helper functions are each provided from a human or non-human primate adenovirus source, such as those described above and/or are available from a variety of sources, including the American Type Culture Collection (ATCC), Manassas, Va. (US). In one currently preferred embodiment, the host cell is provided with and/or contains an E1a gene product, an E1b gene product, an E2a gene product, and/or an E4 ORF6 gene product. The host cell may contain other adenoviral genes such as VAI RNA, but these genes are not required. In a preferred embodiment, no other adenovirus genes or gene functions are present in the host cell.

The adenovirus E1a, E1b, E2a, and/or E4ORF6 gene products, as well as any other desired helper functions, can be provided using any means that allows their expression in a cell. Each of the sequences encoding these products may be on a separate vector, or one or more genes may be on the same vector. The vector may be any vector known in the art or disclosed above, including plasmids, cosmids and viruses. Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by other means, e.g., by exogenously added factors.

D. Host Cells and Packaging Cell Lines

The host cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirements for the cell used is that it not carry any adenovirus gene other than E1, E2a and/or E4 ORF6; it not contain any other virus gene which could result in homologous recombination of a contaminating virus during the production of rAAV; and it is capable of infection or transfection of DNA and expression of the transfected DNA. In a preferred embodiment, the host cell is one that has rep and cap stably transfected in the cell.

One host cell useful in the present invention is a host cell stably transformed with the sequences encoding rep and cap, and which is transfected with the adenovirus E1, E2a, and E4ORF6 DNA and a construct carrying the expression cassette as described above. Stable rep and/or cap expressing cell lines, such as B-50 (International Patent Application Publication No. WO 99/15685), or those described in U.S. Pat. No. 5,658,785, may also be similarly employed. Another desirable host cell contains the minimum adenoviral DNA which is sufficient to express E4 ORF6.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

Once generated, the CpG-depleted AAV vectors may be isolated and purified using techniques known to those of skill in the art and used to prepare suitable formulation.

Pharmaceutical Compositions and Uses Therefor

These CpG-depleted AAV vectors may be prepared into a pharmaceutical composition, typically in the form of a suspension with a pharmaceutically acceptable carrier. The CpG-depleted AAV may be delivered to host cells according to published methods. The AAV may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water.

Optionally, the compositions may contain, in addition to the AAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The vectors or AAV targeting moieties are administered in sufficient amounts to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the lung, liver, skeletal muscle, eye, heart), oral, inhalation, intranasal, intratracheal, intraarterial, intraocular, intravenous, intramuscular, subcutaneous, intradermal, and other parental routes of administration. Routes of administration may be combined, if desired.

Dosages of the viral vector or targeting moiety will depend primarily on factors such as the condition being treated, the age, weight and health of the patient, and may thus vary among patients. For example, a therapeutically effective human dosage of the viral vector is generally in the range of from about 0.1 mL to about 100 mL of solution containing concentrations of from about $1\times10^9$ to $1\times10^{16}$ genomes virus vector. A preferred human dosage for delivery to large organs (e.g., liver, muscle, heart and lung) may be about $5\times10^{10}$ to $5\times10^{13}$ AAV genomes, at a volume of about 1 to 100 mL. A preferred dosage for delivery to eye is about $5\times10^9$ to $5\times10^{12}$ genome copies, at a volume of about 0.1 mL to 1 mL. For example, a therapeutically effective human dosage of an airway conducting cell targeting moiety is generally in the range of about 100 μg to about 10 mg of the moiety. This may be delivered in solution, e.g., in about 0.1 mL to about 100 mL of solution. Optionally, dosage regimens similar to those described for therapeutic purposes may be utilized for immunization using the compositions of the invention. For example, an immunogically effective human dosage of the viral vector is generally in the range of from about 0.1 mL to about 100 mL of solution containing concentrations of from about $1\times10^9$ to $1\times10^{16}$ genomes virus vector. One human dosage for delivery to large organs (e.g., liver, muscle, heart and lung) may be about $5\times10^{10}$ to $5\times10^{13}$ AAV genomes, at a volume of about 1 to 100 mL. One dosage for delivery to eye is about $5\times10^9$ to $5\times10^{12}$ genome copies, at a volume of about 0.1 mL to 1 mL.

In another embodiment, an amount of CpG-depleted AAV composition is administered at an effective dose that is in the range of about $1\times10^8$ genome copies (GC) CpG-depleted AAV/kilogram (kg) to about $1\times10^{14}$ GC/kg, and preferably $1\times10^{11}$ GC CpG-depleted AAV/kg to $1\times10^{13}$ GC CpG-depleted AAV/kg to a human patient. Preferably, the amount of CpG-depleted virus composition administered is $1\times10^8$ GC/kg, $5\times10^8$ GC/kg, $1\times10^9$ GC/kg, $5\times10^9$ GC/kg, $1\times10^{10}$ GC/kg, $5\times10^{10}$ GC/kg, $1\times10^{11}$ GC/kg, $5\times10^{11}$ GC/kg, or $1\times10^{12}$ GC/kg, $5\times10^{12}$ GC/kg, $1\times10^{13}$ GC/kg, $5\times10^{13}$ GC/kg, $1\times10^{14}$ GC/kg.

These doses can be given once or repeatedly, such as daily, every other day, weekly, biweekly, or monthly, or until adequate transgene expression is detected in the patient. In an embodiment, virus compositions are given once weekly for a period of about 4-6 weeks, and the mode or site of administration is preferably varied with each administration. Repeated injection is most likely required for complete ablation of transgene expression. The same site may be repeated after a gap of one or more injections. Also, split injections may be given. Thus, for example, half the dose may be given in one site and the other half at another site on the same day.

Examples of therapeutic products and immunogenic products for delivery by include those previously described for delivery via AAV constructs including those in, e.g., WO 2011/126808A2 and US Published Patent Application No. 2009/0227030-A1, incorporated by reference herein. These CpG-depleted AAV vector may be used for a variety of therapeutic or vaccinal regimens, as described herein. Additionally, these CpG-depleted vectors may be delivered in combination with one or more other vectors or active ingredients in a desired therapeutic and/or vaccinal regimen. For example, the CpG-depleted AAV compositions of the invention can be administered to a human or non-human subject by any method described in the following patents and patent applications that relate to methods of using AAV vectors in various therapeutic applications: U.S. Pat. Nos. 7,282,199; 7,198,951; U.S. Patent Application Publication Nos. US 2008-0075737; US 2008-0075740; International Patent Application Publication Nos. WO 2003/024502; WO 2004/108922; WO 20051033321, each of which is incorporated by reference in its entirety.

In an embodiment, AAV compositions are delivered systemically via the liver by injection of a mesenteric tributary of portal vein. In another embodiment, AAV compositions are delivered systemically via muscle by intramuscular injection into e.g., the quadriceps or bicep muscles. In another embodiment, AAV compositions are delivered to the basal forebrain region of the brain containing the nucleus basalis of Meynert (NBM) by bilateral, stereotactic injection. In another embodiment, AAV compositions are delivered to the CNS by bilateral intraputaminal and/or intranigral injection. In another embodiment, the replication-defective virus compositions of the invention are delivered to the joints by intraarticular injection. In another embodiment, AAV compositions are delivered to the heart by intracoronary infusion. In another embodiment, AAV compositions are delivered to the retina by injection into the subretinal space.

In one embodiment, AAV compositions are delivered systemically via the liver by injection of a mesenteric tributary of portal vein at a dose of about $3.0\times10^{12}$ GC/kg. In another embodiment, AAV compositions are delivered systemically via muscle by up to twenty intramuscular injections in to either the quadriceps or bicep muscles at a dose of about $5.0\times10^{12}$ GC/kg. In another embodiment, AAV compositions are delivered to the basal forebrain region of the brain containing the nucleus basalis of Meynert (NBM) by bilateral, stereotactic injection at a dose of about $5.0\times10^{11}$ GC/kg. In another embodiment, AAV compositions are delivered to the CNS by bilateral intraputaminal and/or intranigral injection at a dose in the range of about $1.0\times10^{11}$ GC/kg to about $5.0\times10^{11}$ GC/kg. In another embodiment, AAV compositions are delivered to the joints by intra-articular injection at a dose of about $1.0\times10^{11}$ GC/mL of joint volume for the treatment of inflammatory arthritis. In another embodiment, AAV compositions are delivered to the heart by intracoronary infusion injection at a dose in the range of about $1.4\times10^{11}$ GC/kg to about $3.0\times10^{12}$ GC/kg. In another embodiment, AAV compositions are delivered to the retina by injection into the subretinal space at a dose of about $1.5\times10^{10}$ GC/kg.

Treatment of Diseases and Disorders and Therapeutic Regimens

The invention provides methods for treating any disease or disorder that is amenable to gene therapy. In one embodiment, "treatment" or "treating" refers to an amelioration of a disease or disorder, or at least one discernible symptom thereof. In another embodiment, "treatment" or "treating" refers to an amelioration of at least one measurable physical parameter associated with a disease or disorder, not necessarily discernible by the subject. In yet another embodiment, "treatment" or "treating" refers to inhibiting the progression of a disease or disorder, either physically, e.g., stabilization of a discernible symptom, physiologically, e.g., stabilization of a physical parameter, or both. Other conditions, including cancer, immune disorders, and veterinary conditions, may also be treated.

Types of diseases and disorders that can be treated by methods of the present invention include, but are not limited to age-related macular degeneration; diabetic retinopathy; infectious diseases e.g., HIV, pandemic flu, category 1 and 2 agents of biowarfare, or any new emerging viral infection; autoimmune diseases; cancer; multiple myeloma; diabetes; systemic lupus erythematosus (SLE); hepatitis C; multiple sclerosis; Alzheimer's disease; Parkinson's disease; amyotrophic lateral sclerosis (ALS), Huntington's disease; epilepsy; chronic obstructive pulmonary disease (COPD); joint inflammation, arthritis; myocardial infarction (MI); congestive heart failure (CHF); hemophilia A; or hemophilia B.

Infectious diseases that can be treated or prevented by the methods of the present invention are caused by infectious agents including, but not limited to, viruses, bacteria, fungi, protozoa, helminths, and parasites. The invention is not limited to treating or preventing infectious diseases caused by intracellular pathogens. Many medically relevant microorganisms have been described extensively in the literature, e.g., See C. G. A Thomas, Medical Microbiology, Bailliere Tindall, Great Britain 1983, the entire contents of which are hereby incorporated herein by reference.

Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor $\alpha$ superfamily, including TGF$\alpha$, activins, inhibins, or any of the bone morphogenic proteins (BMP) BMPs 1-15 as well as TGFb proteins, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including IL-2, IL-4, IL-12 and IL-18), monocyte chemoattractant protein, leukemia inhibitory factor, granulocyte-macrophage colony stimulating factor, Fas ligand, tumor necrosis factors $\alpha$ and $\beta$, interferons $\alpha$, $\beta$, TGFb and $\gamma$, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding $\beta$-glucuronidase (GUSB)).

Still other useful gene products include those used for treatment of hemophilia, including hemophilia B (including Factor IX) and hemophilia A (including Factor VIII and its variants, such as the light chain and heavy chain of the heterodimer and the B-deleted domain; U.S. Pat. Nos. 6,200,560 and 6,221,349). The Factor VIII gene codes for 2351 amino acids and the protein has six domains, designated from the amino to the terminal carboxy terminus as A1-A2-B-A3-C1-C2 [Wood et al, Nature, 312:330 (1984); Vehar et al., Nature 312:337 (1984); and Toole et al, Nature, 342:337 (1984)]. Human Factor VIII is processed within the cell to yield a heterodimer primarily comprising a heavy chain containing the A1, A2 and B domains and a light chain containing the A3, C1 and C2 domains. Both the single chain polypeptide and the heterodimer circulate in the plasma as inactive precursors, until activated by thrombin cleavage between the A2 and B domains, which releases the B domain and results in a heavy chain consisting of the A1 and A2 domains. The B domain is deleted in the activated procoagulant form of the protein. Additionally, in the native protein, two polypeptide chains ("a" and "b"), flanking the B domain, are bound to a divalent calcium cation.

In some embodiments, the minigene comprises first 57 base pairs of the Factor VIII heavy chain that encodes the 10 amino acid signal sequence, as well as the human growth hormone (hGH) polyadenylation sequence. In alternative embodiments, the minigene further comprises the A1 and A2 domains, as well as 5 amino acids from the N-terminus of the B domain, and/or 85 amino acids of the C-terminus of the B domain, as well as the A3, C1 and C2 domains. In yet other embodiments, the nucleic acids encoding Factor VIII heavy chain and light chain are provided in a single minigene separated by 42 nucleic acids coding for 14 amino acids of the B domain [U.S. Pat. No. 6,200,560].

As used herein, a therapeutically effective amount is an amount of AAV vector that produces sufficient amounts of Factor VIII to decrease the time it takes for a subject's blood to clot. Generally, severe hemophiliacs having less than 1% of normal levels of Factor VIII have a whole blood clotting time of greater than 60 minutes as compared to approximately 10 minutes for non-hemophiliacs.

The present invention is not limited to any specific Factor VIII sequence. Many natural and recombinant forms of Factor VIII have been isolated and generated. Examples of naturally occurring and recombinant forms of Factor VII can be found in the patent and scientific literature including, U.S. Pat. Nos. 5,563,045, 5,451,521, 5,422,260, 5,004,803, 4,757,006, 5,661,008, 5,789,203, 5,681,746, 5,595,886, 5,045,455, 5,668,108, 5,633,150, 5,693,499, 5,587,310, 5,171,844, 5,149,637, 5,112,950, 4,886,876, WO 94/11503, WO 87/07144, WO 92/16557, WO 91/09122, WO 97/03195, WO 96/21035, WO 91/07490, EP 0 672 138, EP 0 270 618, EP 0 182 448, EP 0 162 067, EP 0 786 474, EP 0 533 862, EP 0 506 757, EP 0 874 057, EP 0 795 021, EP 0 670 332, EP 0 500 734, EP 0 232 112, EP 0 160 457, Sanberg et al., XXth Int. Congress of the World Fed. Of Hemophilia (1992), and Lind et al., Eur. J. Biochem., 232:19 (1995).

Nucleic acids sequences coding for the above-described Factor VIII can be obtained using recombinant methods or by deriving the sequence from a vector known to include the same. Furthermore, the desired sequence can be isolated directly from cells and tissues containing the same, using standard techniques, such as phenol extraction and PCR of cDNA or genomic DNA [See, e.g., Sambrook et al]. Nucleotide sequences can also be produced synthetically, rather than cloned. The complete sequence can be assembled from overlapping oligonucleotides prepared by standard methods and assembled into a complete coding sequence [See, e.g., Edge, Nature 292:757 (1981); Nambari et al, Science, 223: 1299 (1984); and Jay et al, J. Biol. Chem. 259:6311 (1984).

Factor VIII from humans and non-human animals, including but not limited to companion animals (e.g., canine, felines, and equines), livestock (e.g., bovines, caprines and ovines), laboratory animals, marine mammals, large cats, etc. are encompassed. The AAV vectors may contain a nucleic acid coding for fragments of Factor VIII which is itself not biologically active, yet when administered into the subject improves or restores the blood clotting time. For example, as discussed above, the Factor VIII protein comprises two polypeptide chains: a heavy chain and a light chain separated by a B-domain which is cleaved during processing. As demonstrated by the present invention, cotranducing recipient cells with the Factor VIII heavy and light chains leads to the expression of biologically active Factor VIII. Because, however, most hemophiliacs contain a mutation or deletion in only one of the chain (e.g., heavy or light chain), it may be possible to administer only the chain defective in the patient to supply the other chain.

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor associated polypeptides can be used as target polypeptides such as polypeptides which are found at higher levels in tumor cells including the polypeptide recognized by monoclonal antibody 17 1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce "self"-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) and antibodies (Ab) that bind to endogenous antigens and initiate the inflammatory cascade associated with autoimmune diseases.

Immunogenic Transgenes

Suitably, the AAV vectors of the invention avoid the generation of immune responses to the AAV sequences contained within the vector. However, these vectors may nonetheless be formulated in a manner which permits the expression of a transgene carried by the vectors to induce an immune response to a selected antigen. For example, in order to promote an immune response, the transgene may be expressed from a constitutive promoter, the vector can be adjuvanted as described herein, the transgene can optionally be modified to express more CpGs to induce a greater immune response, and/or the vector can be put into degenerating tissue.

Examples of suitable immunogenic transgenes include those selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Other viral families include the astroviruses and the calcivirus family. The calcivirus family encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinatin encephalomyelitis virus (pig), feline infectious peritonitis virus (cats), feline enteric coronavirus (cat), canine coronavirus (dog), and human respiratory coronaviruses, which may cause the common cold and/or non A, B or C hepatitis, and which include the putative cause of sudden acute respiratory syndrome (SARS). Within the coronavirus family, target antigens include the E1 (also called M or matrix protein), E2 (also called S or Spike protein), E3 (also called HE or hemagglutin elterose) glycoprotein (not present in all coronaviruses), or N (nucleocapsid). Still other antigens may be targeted against the arterivirus family and the rhabdovirus family. The rhabdovirus family includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus may be a suitable source of antigens. The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. Another source of antigens is the bornavirus family. The reovirus family includes the genera reovirus, rotavirus (which causes acute gastroenteritis in children), orbiviruses, and cultivirus (Colorado Tick fever, Lebombo (humans), equine encephalosis, blue tongue). The retrovirus family includes the sub family oncorivirinal which encompasses such human and veterinary diseases as feline leukemia virus, HTLVI and HTLVII, lentivirinal (which includes HIV, simian immunodeficiency virus, feline immunodeficiency virus, equine infectious anemia virus, and spumavirinal). The papovavirus family includes the sub-family polyomaviruses (BKU and JCU viruses) and the sub family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub family gammaherpesvirinae, which includes the genera lymphocryptovirus, EBV (Burkitts lymphoma), human herpesviruses 6A, 6B and 7, Kaposi's sarcoma-associated herpesvirus and cercopithecine herpesvirus (B virus), infectious rhinotracheitis, Marek's disease virus, and rhadinovirus. The poxvirus family includes the sub family chordopoxvirinae, which encompasses the genera orthopoxvirus (Variola major (Smallpox) and Vaccinia (Cowpox)), parapoxvirus, avipoxvirus, capripoxvirus, leporipoxvirus, suipoxvirus, and the sub family entomopoxvirinae. The hepadnavirus family includes the Hepatitis B virus. One unclassified virus which may be suitable source of antigens is the Hepatitis delta virus, Hepatitis E virus, and prions. Another virus which is a source of antigens is Nipan Virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram positive cocci include pneumococci; staphylococci (and the toxins produced thereby, e.g., enterotoxin B); and streptococci. Pathogenic gram negative cocci include meningococcus; gonococcus. Pathogenic enteric gram negative bacilli include enterobacteriaceae; *pseudomonas*, acinetobacteria and eikenella; melioidosis; *salmonella; shigella; haemophilus; moraxella; H. ducreyi* (which causes chancroid); *brucella* species (brucellosis); *Francisella tularensis* (which causes tularemia); *Yersinia pestis* (plague) and other *yersinia* (*pasteurella*); *streptobacillus moniliformis* and spirillum; Gram-positive bacilli include *Listeria monocytogenes*; erysipelothrix rhusiopathiae; *Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism (*Clostridum botulinum* and its toxin); *Clostridium perfringens* and its epsilon toxin; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include glanders (*Burkholderia mallei*); actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever (*Coxiella burnetti*), and Rickettsialpox. Examples of *Mycoplasma* and chlamydial infections include: *Mycoplasma pneumoniae*; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii*; Trichans; *Toxoplasma gondii*; babesiosis; giardiasis; trichinosis; filariasis; schistosomiasis; nematodes; trematodes or flukes; and cestode (tapeworm) infections.

Many of these organisms and/or the toxins produced thereby have been identified by the Centers for Disease Control [(CDC), Department of Health and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); *Brucella* species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci*

(psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

The vectors of the invention can be used to deliver immunogens. In rheumatoid arthritis (RA), several specific variable regions of T-cell receptors (TCRs) which are involved in the disease have been characterized. These TCRs include V 3, V 14, V 17 and V 17. Thus, delivery of a nucleic acid sequence that encodes at least one of these polypeptides will elicit an immune response that will target T cells involved in RA. In multiple sclerosis (MS), several specific variable regions of TCRs which are involved in the disease have been characterized. These TCRs include V 7 and V 10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V 6, V 8, V 14 and V 16, V 3C, V 7, V 14, V 15, V 16, V 28 and V 12. Thus, delivery of a nucleic acid molecule that encodes at least one of these polypeptides will elicit an immune response that will target T cells involved in scleroderma.

A CpG-modified AAV viral vector of the invention provides an efficient gene transfer vehicle which can deliver a selected transgene to a selected host cell in vivo or ex vivo even where the organism has neutralizing antibodies to one or more AAV serotypes. In one embodiment, the rAAV and the cells are mixed ex vivo; the infected cells are cultured using conventional methodologies; and the transduced cells are re-infused into the patient.

These compositions are particularly well suited to gene delivery for therapeutic purposes and for immunization, including inducing protective immunity. Further, the compositions of the invention may also be used for production of a desired gene product in vitro. For in vitro production, a desired product (e.g., a protein) may be obtained from a desired culture following transfection of host cells with a rAAV containing the molecule encoding the desired product and culturing the cell culture under conditions which permit expression. The expressed product may then be purified and isolated, as desired. Suitable techniques for transfection, cell culturing, purification, and isolation are known to those of skill in the art.

In one embodiment, a method for improving adeno-associated virus (AAV)-mediated gene expression is described. The method involves generating an AAV viral particle comprising a modified packaging insert, wherein said packaging insert comprises a nucleic acid molecule comprising at least one AAV inverted terminal repeat (ITR) and an exogenous gene sequence under the control of regulatory sequences which control expression of the gene product, wherein said sequences of said nucleic acid molecule are modified to reduce CpG di-nucleotides such that in immune response to the vector is reduced as compared to the unmodified AAV vector without significant reduction in expression of the gene product; and delivering the AAV to a subject intramuscularly. In another embodiment, a regimen for repeat administration of a gene product. The regimen involves delivering to a subject a CpG-depleted adeno-associated viral (AAV) vector. The vector has an AAV capsid having packaged therein a nucleic acid molecule comprising at least one AAV inverted terminal repeat (ITR) and an exogenous gene sequence under the control of regulatory sequences which control expression of the gene product, wherein said sequences of said nucleic acid molecule are modified to reduce CpG di-nucleotides such that in immune response to the vector is reduced as compared to the unmodified AAV vector without significant reduction in expression of the gene product; and delivering to the subject a second vector comprising the exogenous gene sequence. The second vector may be a second CpG-depleted AAV, which may differ from the first CpG-depleted AAV. Alternatively, a CpG-depleted AAV as described herein may be used in a regimen using other types of AAV vector, or other viral and non-viral constructs. For example, regimens analogous to those described in EP 1 742 668B1 and WO 2006/078279A2, published 27 Jul. 2006, may be performed using a CpG-depleted AAV of the invention.

EXAMPLES

The following examples are illustrative only and are not a limitation on the present invention.

Example 1

In the Absence of TLR9 Signaling, AAVrh32.33nLacZ Muscle Gene Transfer Results in Stable Transgene Expression The current study assessed the requirement for TLR9 signaling in T cell immunoreactivity and transgene loss in response to AAVrh32.33. These mechanistic findings were subsequently translated into a modified, CpG-depleted AAVrh32.33 vector that escapes the adaptive immune response and exhibits stable, long-term transgene expression.

A. Material and Methods:

1. Mice:

C57BL/6 wild type (WT) mice were ordered from The Jackson Laboratory. Toll-like receptor 9 knockout (TLR9KO) mice were a kind gift from Dr. Phillip Scott (University of Pennsylvania, Philadelphia, Pa.). All mice were housed under specific pathogen-free conditions in the TRL Animal Facility at the University of Pennsylvania. All animal procedure protocols were approved by the Institutional Animal Care and Use Committee of the University of Pennsylvania.

2. Adeno-Associated Viral Vectors (AAV) Mediated Transduction of the Muscle

An AAV8 and AAVrh32.33 pseudotyped vector flanked with AAV2 ITRs encoded a nuclear targeted form of β-galactosidase (nLacZ) under the transcriptional control of a CMV-enhanced chicken β-actin (CB) promoter [L. Wang, et al., 1999. Sustained correction of bleeding disorder in hemophilia B mice by gene therapy.
Proc Natl Acad Sci USA 96: 3906-3910.] An AAVrh32.33 pseudotyped vector flanked with AAV2 ITRs encoded either a wild type or CpG-depleted cellular targeted form of β-galactosidase (LacZ) (Invivogen). The CpG-depleted promoter and polyA for this construct were also obtained from Invivogen. Over 320 CpGs are present in the wild type LacZ expressing vector (16 CpGs in the inverted terminal repeats (ITRs) and 308 in the transgene); the CpG depleted LacZ vector sequence contains only 16 CpGs located in the ITRs. Outside of the transgene sequence, both vectors are identical in sequence and contain CpG-depleted human elongation factor 1-alpha (E1F-α) promoter, CMV enhancer, intron, SV40 3'UTR, and ITRs. AAV vectors were produced by a scaled-down version of a previously described method by triple transfection of vector genome, AAV helper and adenovirus helper plasmids [M. Lock, et al, 2010. Rapid, simple and versatile manufacturing of recombinant adeno-associated viral vectors at scale. Hum Gene Ther 21: 1259-1271]. Purification of vectors involved a single iodixanol step gradient [Zolotukhin, S., et al., 1999]. Recombinant adeno-associated virus purification using novel methods improves infectious titer and yield. Gene Ther 6: 973-985] and subsequent DNAse treatment. Real-time PCR using a primer/probe set corresponding to the poly A region of the vector and linearized plasmid standards determined genome titer (genome copy/ml) of AAV vectors. All vectors used in this study passed the endotoxin assay (threshold 10 EU/mL) using QCL-1000 chromogenic LAL test kit (Cambrex Bio Science). Vectors were produced by Penn Vector Core at the University of Pennsylvania. Mice were injected in the gastroc with $10^{11}$ vector genomes (VG) of AAV in a 50 μl volume.

3. Immunohistochemistry

To examine expression of nuclear β-gal, X-gal staining of snap-frozen liver cryosections was performed according to standard protocols [Bell, P., et al., Histochem Cell Biol 124: 77-85.] Representative sections from 4 mice per group were imaged by using brightfield microscopy with a 10× objective. To analyze major histocompatibility complex class II (MHC II) expression and CD4+/CD8+ infiltrating cell types within the liver, immunostaining and fluorescent microscopy were performed on acetone-fixed cryosections stained with rat anti-CD4 and anti-CD8 antibodies (Ab) from BD Pharmingen and anti-MHC II Ab (Biolegend) as previously described [Mays, L. E., and J. M. Wilson. 2009. J Gene Med 11:1095-1102].

4. MHC Class I Tetramer Staining

PE-conjugated MHC class I H2-$k^b$-ICPMYARV tetramer complex was obtained from Beckman Coulter. At kinetic time points after vector injection, tetramer staining was performed on heparinized whole blood cells isolated by retro-orbital bleeds. Cells were co-stained for 30 minutes at room temperature with PE-conjugated tetramer and FITC-conjugated anti-CD8a (Ly-2) Ab (BD Pharmingen). Red blood cells were lysed and cells were fixed with iTAg MHC tetramer lysing solution supplemented with fix solution (Beckman Coulter) for 15 minutes at room temperature. The cells were then washed three times in PBS and resuspended in 1×PBS. Data were gathered with an FC500 Flow Cytometer (Beckman Coulter) and were analyzed with FlowJo analysis software (Tree Star). In the analysis, lymphocytes were selected on the basis of forward and side scatter characteristics, followed by selection of CD8+ cells, and subsequently the tetramer-positive CD8+ T cell population.

5. ELISPOT Assays for Cytokine-Producing Cells

T cell medium consisted of the following: DMEM (Cellgro; Mediatech) supplemented with 10% heat-inactivated FBS (Hyclone), 1% penicillin/streptomycin (Cellgro; Mediatech), 1% L-glutamine (Cellgro; Mediatech), 10 mM HEPES buffer (Cellgro; Mediatech), 0.1 mM nonessential amino acids (Invitrogen), 2 mM sodium pyruvate Cellgro; Mediatech) and $10^{-6}$ M 2-ME (Cellgro; Mediatech).

Splenocytes were isolated by mechanical dissociation followed by red blood cell (RBC) lysis via hypotonic shock and resuspended at a concentration of $5\times10^6$ cells/mL and plated at $5\times10^5$ cells/well in triplicate on 96-well round-bottom plates. ELISPOT assays were performed according to the manufacturer's instructions (BD Biosciences). T cell medium supplemented with 2 μg/mL of H2-$k^b$-restricted β-gal CD8 T cell epitope (ICPMYARV) and H2-$k^b$-restricted AAVrh32.33 capsid epitope (SSYELPYVM) (Mimotopes) was used to stimulate splenocytes. Splenocytes were incubated at 37° C., 5% $CO_2$ for 18 hours. Spots were visualized by addition of 3-Amino-9-Ethylcarbazole (AEC) substrate set (BD Biosciences) and counted using the AID ELISPOT reader system (Cell Technology).

6. RNA Isolation and Quantitative RT-PCR

Gastroc tissue was homogenized in 1 ml TRIzol (Life Technologies) and RNA was isolated per the manufacturer's protocol. Total RNA (5 μg) was reverse transcribed using 10×PCR buffer (Roche), 10 mM dNTP, oligo(dt), M-MLV-RT (all from Invitrogen), and RNAsin (Promega). Products were then cleaned with 1:1 phenol/chloroform/isoamyl (25:24:1) and reprecipitated with 7.5 M $NH_4OAC$ in pure ethanol overnight at −80° C.

Real-time PCR was performed on cDNA using a 7500 Real Time PCR System (Applied Biosystems). Primer binding to DNA was detected by SYBR 2× Master Mix (Applied Biosystems). Relative expression of the gene of interest was expressed as the comparative concentration of the gene product to the GAPDH product. Transcript relative expression of target genes were then expressed as fold induction over mock treated (PBS injected) naïve WT mouse gastroc samples. Significance was determined with an unpaired Student t test.

7. Muscle Weight

Muscle weight was determined by weighing the vector injected gastroc and comparing it to the total body weight of the animal on day 60 post-injection.

8. Statistical Analysis

Data were analyzed with GraphPad Prism 4.0c software using unpaired Student t-tests. p values of ≤0.05 were considered statistically significant.

RESULTS:

B. In the Absence of TLR9 Signaling, AAVrh32.33nLacZ Muscle Gene Transfer Results in Stable Transgene Expression.

Studies in C57BL/6 mice demonstrate that AAVrh32.33 intramuscular gene transfer induces a robust adaptive immune response towards both capsid and transgene antigen, heavy cellular infiltrate, and a loss of detectable transgene expression [Mays, L. E., et al, 2009. J of Immunol 182: 6051-6060]. To evaluate the role of TLR9 signaling in the induction of this adaptive immune response and transgene loss, WT and TLR9KO mice were intramuscularly (I.M.) injected with $1\times10^{11}$ viral particles of AAVrh32.33 expressing a nuclear-targeted β gal (nLacZ) reporter gene under the direction of a chicken β-actin promoter. Gastroc tissue was recovered from the WT and TLR9KO mice and β gal expression in the muscle was assessed by X-gal histochemical stain (FIG. 1). WT controls exhibited a complete loss of β-gal positive cells at 60 days post-injection. In contrast, abrogation of TLR9 signaling resulted in stable transgene expression. These results suggest that TLR9 signaling is required for transgene loss following AAVrh32.33 muscle gene transfer.

C. A Deficiency in TLR9 Signaling Reduces Immunoreactivity Toward AAVrh32.33 Capsid and Transgene Antigen.

In WT C57BL/6 mice, AAVrh32.33 muscle gene transfer is associated with a robust Th1 response and a significant percentage of nLacZ reactive CD8+ T cells [Mays et al, 2009, J Immunol, cited above]. To investigate the relationship between TLR9 signaling and immunoreactivity, MHC I tetramer stain and ELISPOT assays were used to quantify transgene reactive CD8+ T cells and primed transgene and capsid responsive IFNγ-producing cells (FIG. 2). Peripheral blood cells isolated from whole blood were co-stained with a FITC-conjugated anti-CD8 Ab and a PE-conjugated H-2K$^b$-ICPMYARV tetramer to determine the percentage of nLacZ-reactive CD8+ T cells in the total CD8+ T cell population (FIG. 2A). TLR9 deficient mice exhibited a significant reduction in the percentage of nLacZ responsive CD8+ T cell population compared to WT mice.

Figure 2B:
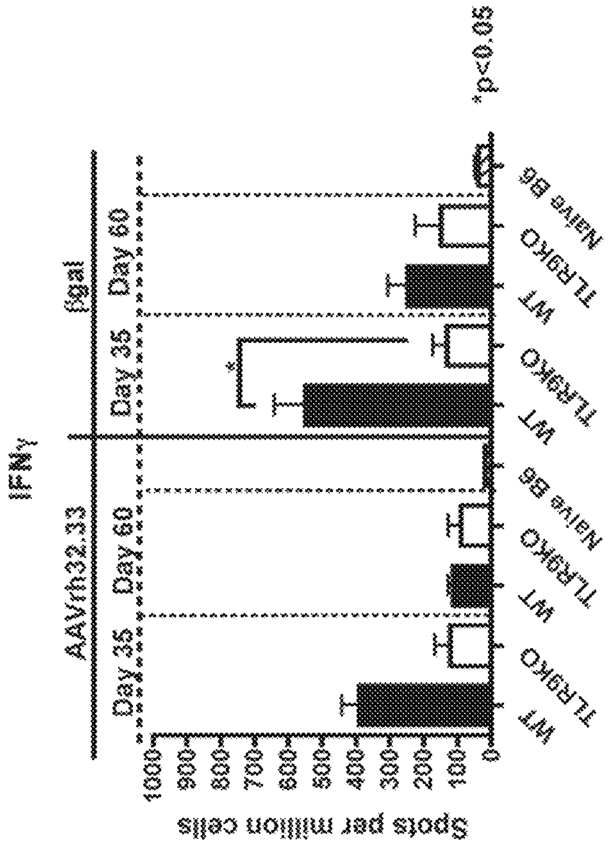
FIG. 2B is a bar chart showing gamma interferon (IFNγ) levels for both wild-type and TLR9 knock out mice on days 35 and 60 following intramuscular injection with $1\times10^{11}$ GC of AAVrh32.33nLacZ. Results represent the mean+/−SEM of cytokine-producing cells that are reactive toward transgene (nLacZ) and AAVrh32.33 capsid antigen from at least n=3 per group.
Figure 2A:
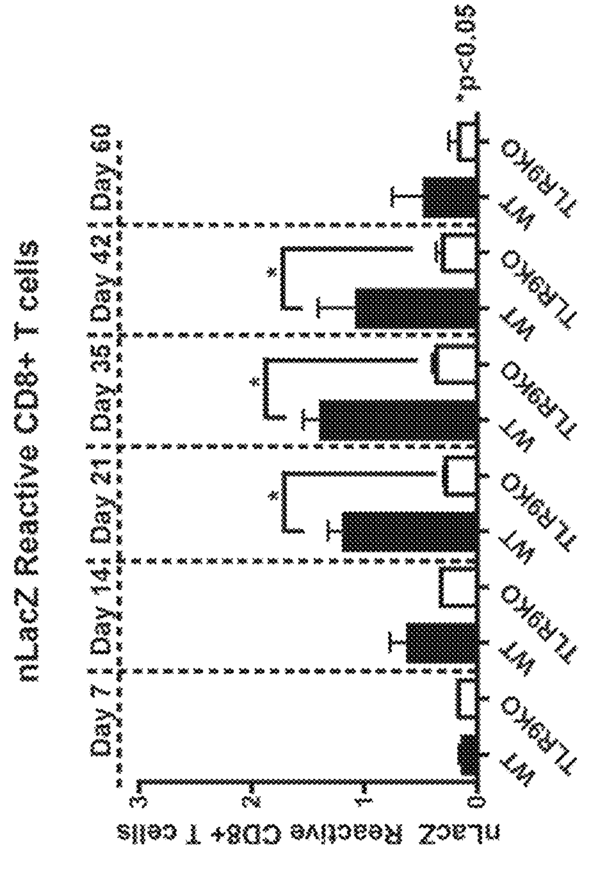
FIG. 2A is a bar chart comparing nLacZ reactive CD8+ T cells in WT and TLR9KO mice on days 7, day 14, day 21, day 35, day 42 and day 60 following intramuscular injection with $1\times10^{11}$ GC of AAVrh32.33nLacZ. Results represent the mean+/−SEM of tetramer positive or cytokine-producing cells from at least n=3 per group.

To determine whether TLR9 signaling regulates AAVrh32.33nLacZ cellular immune responses, we used ELISPOT to quantify the number of in vivo primed capsid and transgene Th1 (IFNγ) responses (FIG. 2B). Elevated capsid and transgene reactive Th1 responses were observed in WT but not TLR9KO vector recipients indicating an abrogation of Th1 responses in the absence of TLR9 signaling. These findings demonstrate the inhibitory effect of TLR9 signaling blockade on T cell effector function following stimulation with AAVrh32.33 capsid and transgene antigens.

Figure 3:
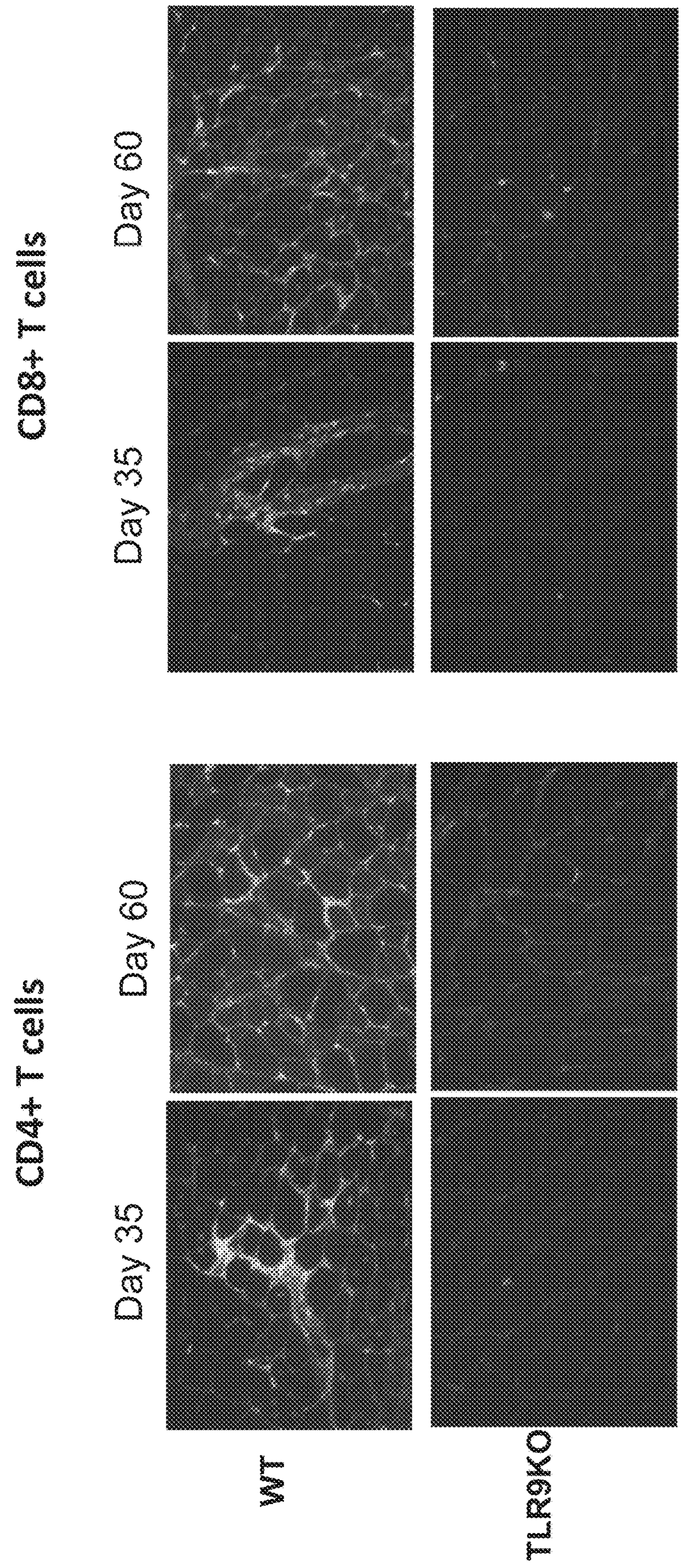
FIG. 3 provides photographs of representative muscle sections (4 mice per group) recovered from WT and TLR9KO mice that received I.M. injection of $1\times10^{11}$ GC of AAVrh32.33nLacZ. Sections were stained with anti-CD4 and anti-CD8 antibody (Ab) and examined by fluorescent miscroscopy. 4 mice per group.

D. Minimal Cellular Infiltrate Observed in Muscle Following AAVrh32.33nLacZ I.M. Injection Observed in TLR9 Deficient Mice Heavy CD4+ and CD8+ cellular infiltrate has been observed in WT C57BL/6 mice following AAVrh32.33 intramuscular vector transduction [Mays et al, J Immunol, 2009, cited above]. To determine the requirement for TLR9 signaling in the induction of this extensive infiltrate, WT and TLR9KO muscle sections were stained with anti-CD4 and anti-CD8 Ab and examined by fluorescent microscopy at 35 and 60 days vector post-administration (FIG. 3). As expected, significant cellular infiltrate was detected in WT mice. In contrast, minimal cellular infiltrate was observed in TLR9KO mice. These results are consistent with a TLR9 dependent mechanism of cellular infiltrate in response to intramuscular AAVrh32.33nLacZ transduction.

E. Enhanced Transgene Expression Observed in the Muscles of TLR9 Deficient Mice Injected with AAV8

Figure 4:
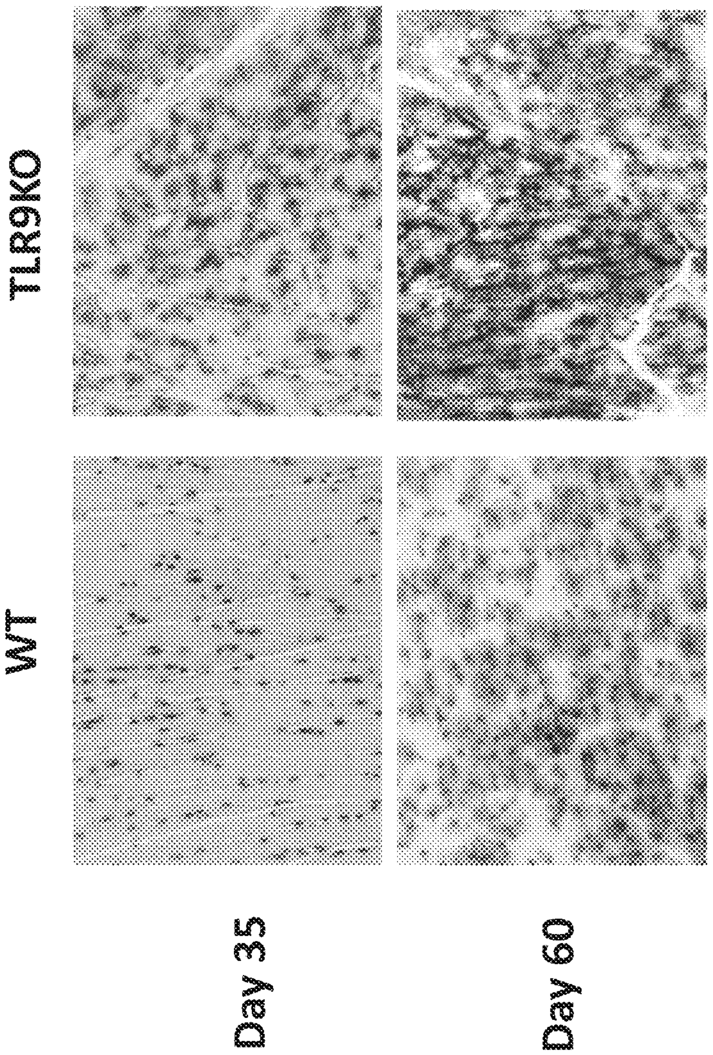
FIG. 4 shows photographs of X-gal histochemical stains of muscle from WT and TLR9KO mice injected intramuscularly with $1\times10^{11}$ GC of AAVrh32.33nLacZ. Representative sections are from 35 and 60 days post-injection. 4 mice per group.

Historically, AAV8 gene delivery to WT C57BL/6 muscle tissue results in minimal Th1 responses, negligible cellular infiltrate and prolonged transgene expression [Mays et al, J Immunol, 2009, cited above]. To investigate the role of TLR9 detection of AAV8 and its effect, if any, on AAV8 gene expression, WT and TLR9KO mice were injected intramuscularly with $1\times10^{11}$ GC of AAV8nLacZ. X-gal histochemical stain of muscle sections 35 and 60 days post vector administration (FIG. 4). Enhanced expression is detected in the muscle of TLR9KO mice indicating the detection of AAV8 through this innate immune sensor and an effect on transgene expression even in the case of an AAV vector that induces a minimal immune response.

Figure 5:
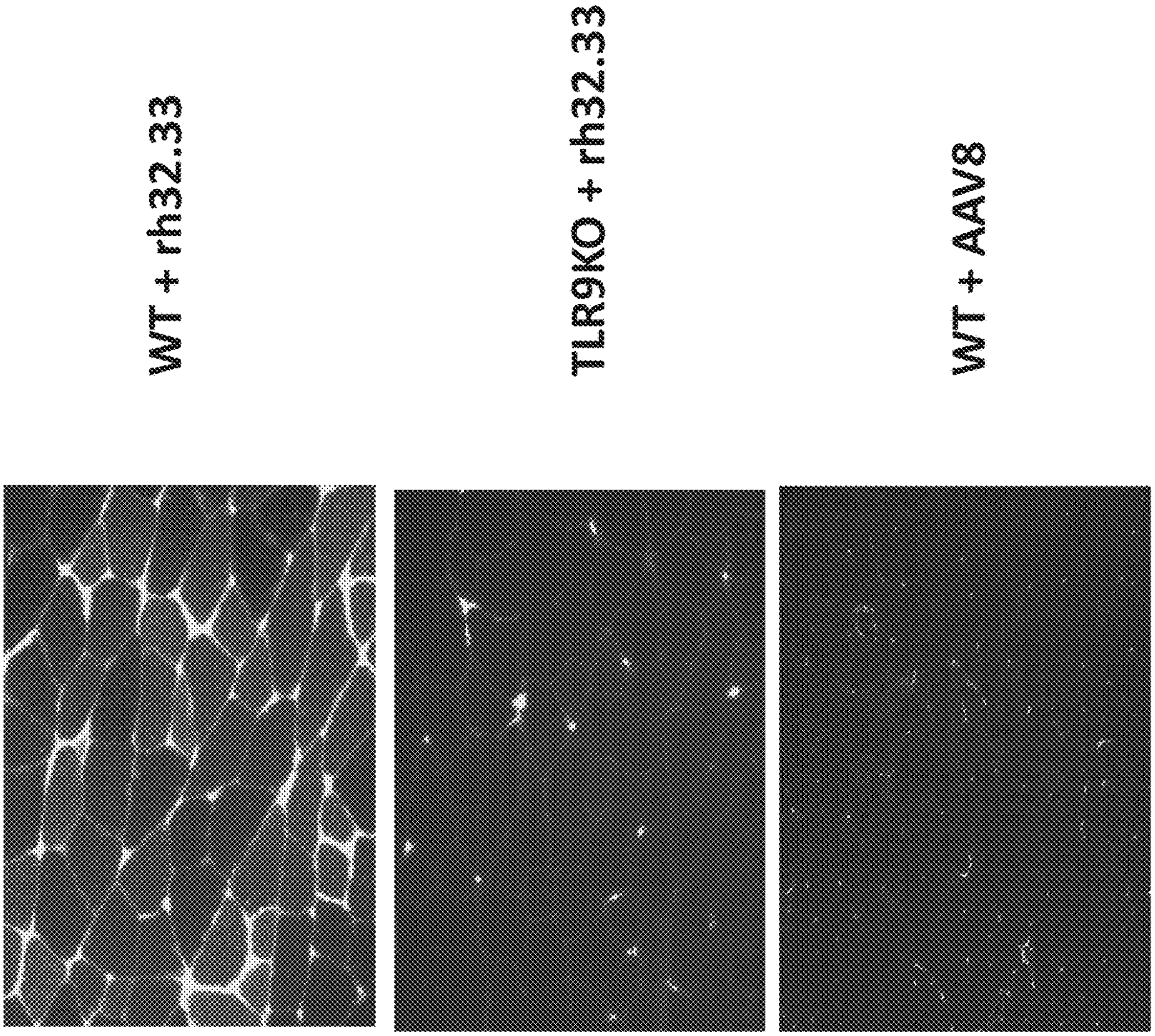
FIG. 5 provides photographs of muscle section that was recovered from WT and TLR9KO mice that received I.M. injection of either $1\times10^{11}$ GC of AAVrh32.33 or AAV8 expressing nLacZ. Sections recovered on days 35 and 60 were stained with anti-MHC II Ab and examined by fluorescent miscroscopy. Representative sections are shown. 4 mice per group.

F. TLR9 Signaling is Both Necessary and Sufficient to Upregulate MHC II Expression on a Muscle Tissue Muscle tissue possesses a unique function as a non-professional antigen presenting cell (APC) that can effectively stimulate both CD4+ and CD8+ T cells to survive, proliferate, and acquire effector function. To assess the ability of AAVrh32.33 to induce MHC II expression on skeletal muscle, gastroc sections from WT and TLR9KO mice that received I.M. injection of $1\times10^{11}$ GC of AAV8rh32.33nLacZ or AAV8nLacZ, were stained with an anti-MHC II Ab and examined by fluorescent microscopy 35 days post gene transfer (FIG. 5). WT muscle tissue transduced with AAVrh32.33nLacZ revealed significant upregulation of MHC II on skeletal muscle, which was not present on muscle tissue from TLR9 deficient mice administered AAVrh32.33nLacZ or WT mice that received AAV8. These findings reveal the requirement of TLR9 signaling for MHC II expression on muscle following AAVrh32.33, while AAV8 minimally induces MHC II expression.

Figure 6:
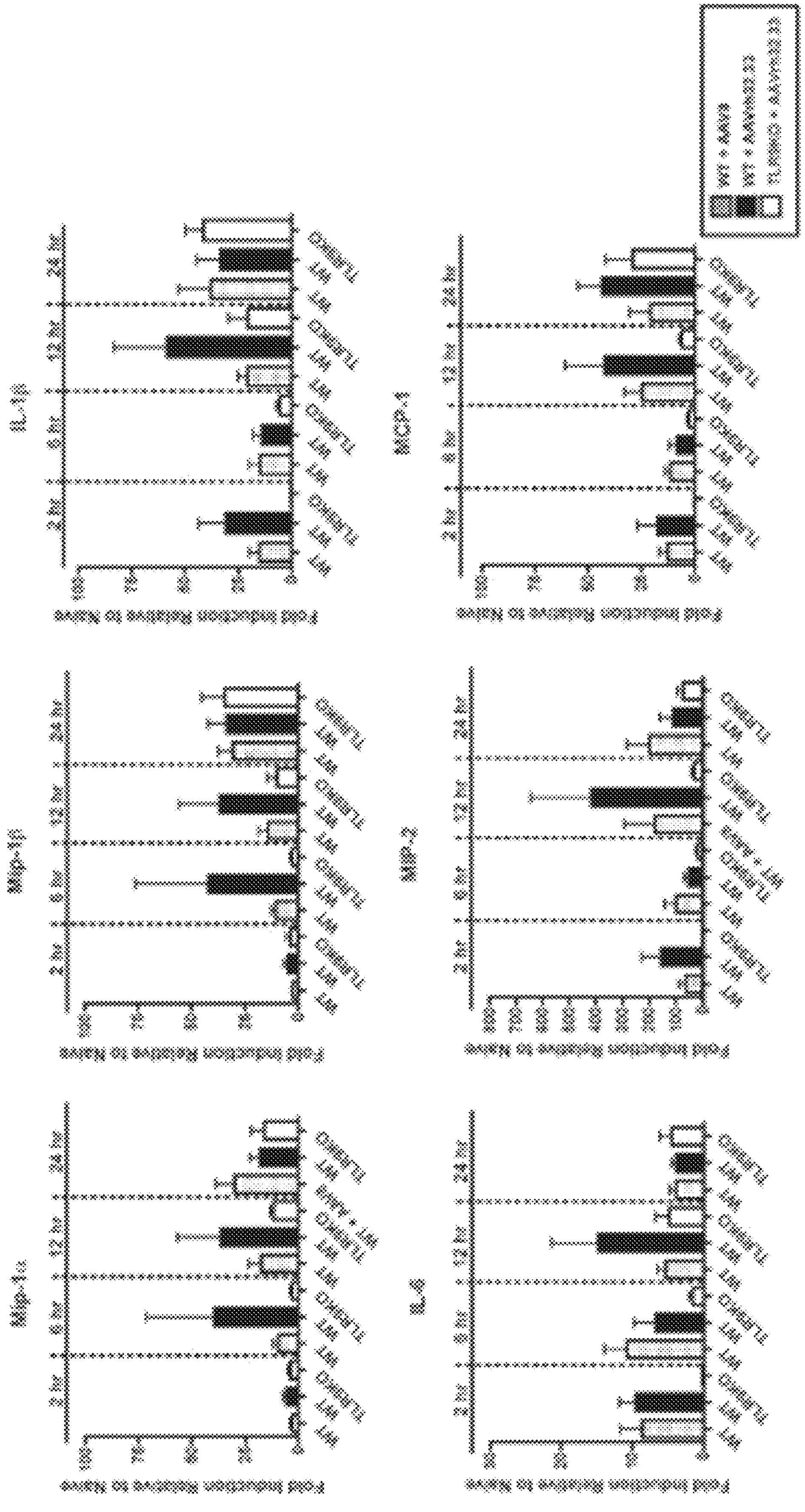
FIG. 6 provides a series of bar charts providing transcript levels of various cytokines assessed by quantitative reverse transcriptase (RT) polymerase chain reaction (PCR) following isolation of RNA from the gastric muscle of WT and TLRKO mice administered $1\times10^{11}$ GC AAVrh32.33nLacZ or AAV8nLacZ at kinetic time points (2, 6, 12, 24 hours). Transcript levels of MIP-1α, MIP-1β, IL-1β, IL-6, MIP-2 and MCP-1 were assessed by quantitative RT-PCR. Results depict the mean of RNA expression. n=4 mice per group.

G. AAVrh32.33 Induces Early Innate Immune Gene Transcript Induction in WT, but not TLR9, Deficient Mice Zaiss et al. demonstrated that adenovirus vector transduction of human HeLa cells and murine renal epithelium-derived cells induce the expression of numerous chemokines and inflammatory cytokines [Zaiss, A., et al., 2002. *J of Virol* 76 (9) 4580-4590]. To assay for innate immune gene transcript induction following intramuscular injection of AAVrh32.33 and AAV8 in WT or TLR9 deficient mice, we performed quantitative RT-PCR at early kinetic time points to detect innate chemokine and inflammatory transcript levels following gene transfer (FIG. 6). Transcript levels of MIP-1α, MIP-1β, MIP-2, MCP-1, IL-1α and IL-6 were quantified and expressed as fold induction over mock treated (PBS injected) WT mice. A dramatic induction of both chemokine and cytokine transcripts was observed in WT mice transduced with AAVrh32.33, but not in TLR9KO mice, or in WT mice administered AAV8. Collectively, our data suggests that TLR9 signaling is both necessary and sufficient to induce innate (FIG. 6) and adaptive (FIG. 2) immune responses toward an immunogenic AAV vector. Our observation that TLR9 deficient AAVrh32.33 vector recipients exhibit minimal immunoreactivity and stable transgene expression led us to hypothesize that CpG depleted AAVrh32.33 vectors would escape immune detection and exhibit long-term transgene expression.

H. CpG Depleted Vector Generation

Figure 7A:
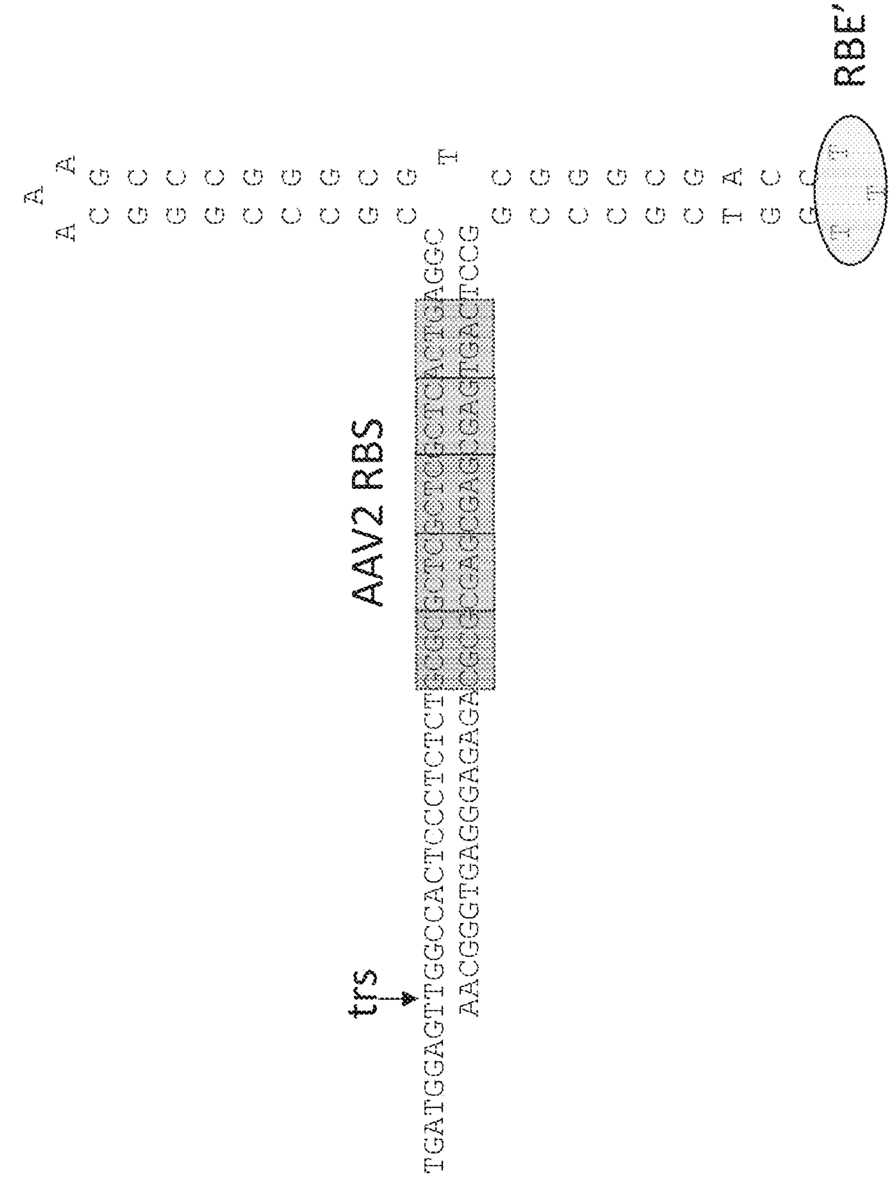
FIG. 7A illustrates the structure and sequence of the wild-type AAV2 inverted terminal repeat showing AAV2 Rep binding site (RBS), spacer sequence, terminal resolution site (trs), and rep binding element [SEQ ID NO:4].
Figure 7B:
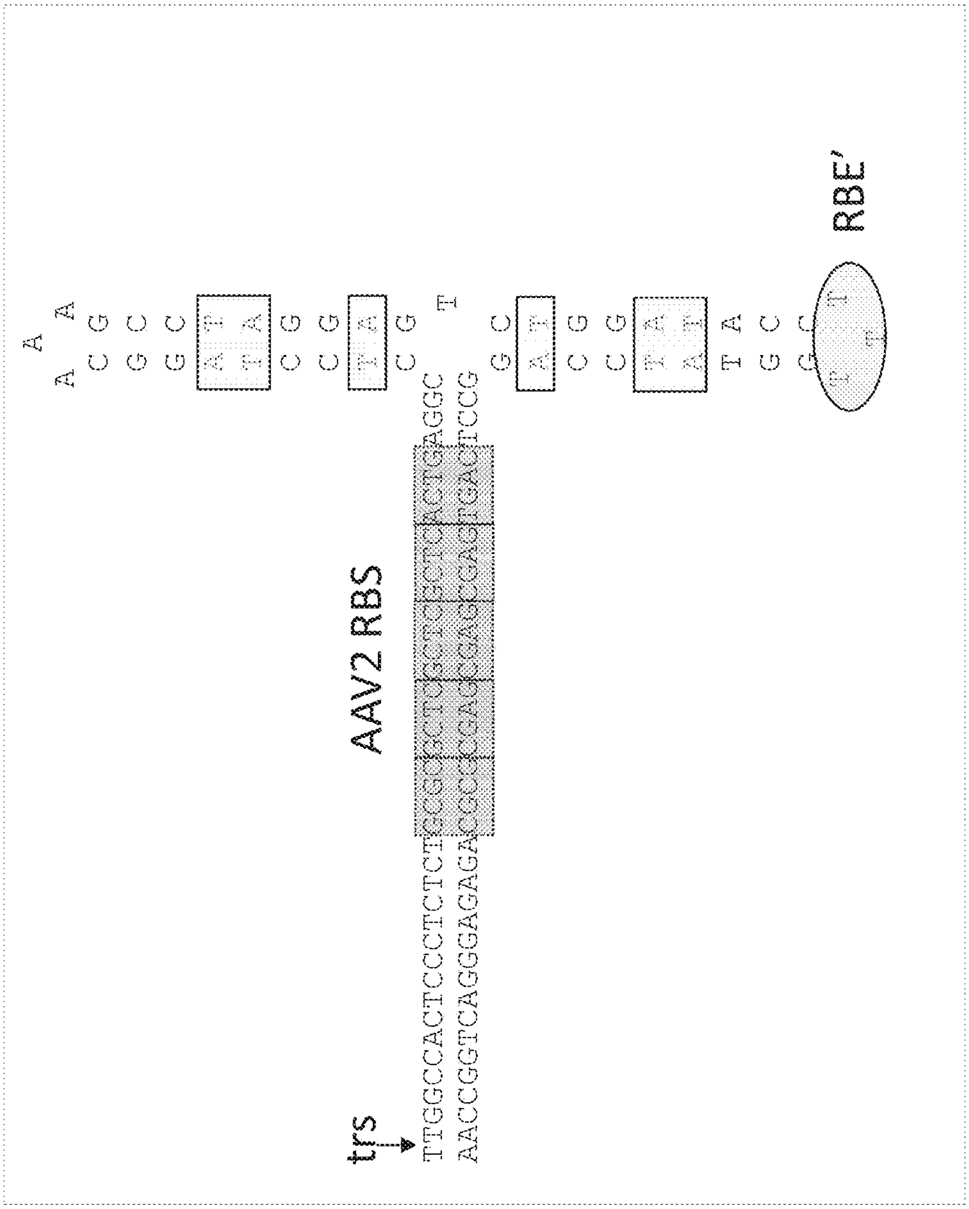
FIG. 7B illustrates the AAV2 inverted terminal repeat with CpG dinucleotides outside of the RBS deleted [SEQ ID NO:5].

TLR9 acts as an innate immune sensor that specifically recognizes and responds to unmethylated CpG motifs present in ~7% of microbial genomes compared to ~1% vertebrate DNA. Systemic delivery of cationic lipid-plasmid DNA (pDNA) vectors that contain CpG motifs stimulate acute inflammatory responses with adverse effects on transgene expression [Yew, N. S., et al, 2002, Mol Ther 5(6): 731-738]. CpG depleted plasmid DNA vectors, on the other hand, exhibit long-term expression and enhanced safety. To determine whether CpG depleted AAVrh32.33 vectors would abrogate the robust cellular immune response and transgene loss we observed in the previous experiments (FIG. 1-3, 5, 6), we generated a LacZ CpG depleted vector genome that retained a mere 16 CpGs located in the inverted terminal repeat sequence (FIGS. 7A and 7B; SEQ ID NO: 4 and 5). See, also, sequences provided below. CpGs in the EF1-α promoter, CMV enhancer, LacZ transgene, intron, and SV40 polyA were reduced in the CpG depleted vector (CpG-), while the WT vector (CpG+), which contained the same backbone sequence, retained 16 CpGs in the ITRs as well as 308 CpGs in the LacZ transgene (total=324 CpGs). The sequence of the CpG-modified LacZ transgene is provided in FIG. 11 [SEQ ID NO: 7].

AAV2 ITR alignment document

```
SEQ ID NO: 1: AAV2 ITR
SEQ ID NO: 2: CpG depleted ITR
SEQ ID NO: 3: Consensus ITR

                     1                                                 50
        AAV2 ITR   (1)  AGGAACCCCTAGTGATGGAGTTGGCCACTCCCTCTCTGCGCGCTCGCTCG

CpG depleted ITR   (1)  ----------------------GGCCAGTCCCTCTCTGCGCGCTCGCTCG

       Consensus   (1)                        GGCCA TCCCTCTCTGCGCGCTCGCTCG

                        51                                              100
        AAV2 ITR  (51)  CTCACTGAGGCCGGGCGACCAAAGGTCGCCCGACGCCCGGGCTTTGCCCG

CpG depleted ITR  (29)  CTCACTGAGGCCTGGATACCAAAGGTATCCAGACTCCTAGGCTTTGCCTA

       Consensus  (51)  CTCACTGAGGCC GG  ACCAAAGGT  CC GAC CC  GGCTTTGCC

                        101                                             150
        AAV2 ITR (101)  GGCGGCCTCAGTGAGCGAGCGAGCGCGCAGAGAGGGAGTGGCCAA-----

CpG depleted ITR  (79)  GGAGGCCTCAGTGAGCGAGCGAGCGCGCAGAGAGGGAGTGGCCAACTCCA

       Consensus (101)  GG GGCCTCAGTGAGCGAGCGAGCGCGCAGAGAGGGAGTGGCCAA

                        151
        AAV2 ITR (146)  --------
CpG depleted ITR (129)  TCACTAGG
       Consensus (151)
```

I. CpG Depleted AAV2/Rh32.33 Vectors Exhibit Stable Transgene Expression

Figure 8:
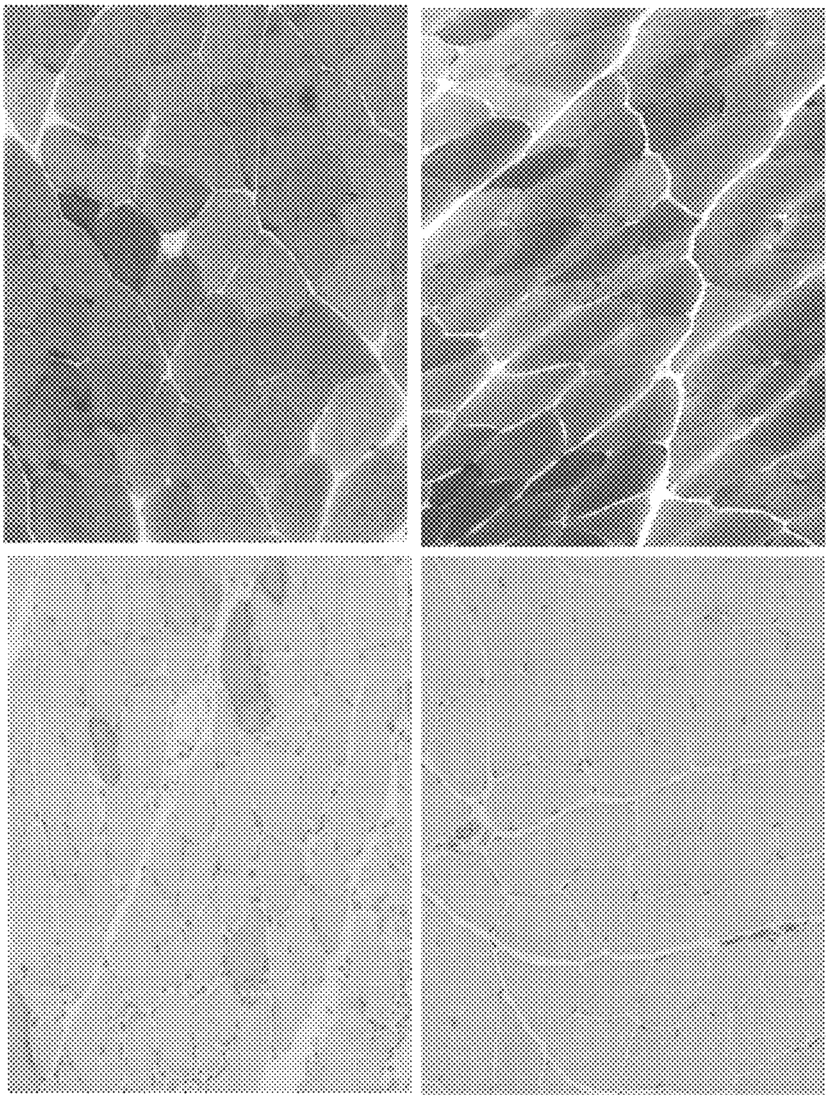
FIG. 8 provides photographs of representative sections of X-gal histochemical stains of muscle from WT mice injected I.M. with $1\times10^{11}$ GC of AAVrh32.33LacZCpG+ or of AAVrh32.33LacZCpG− vectors. Muscle was harvested at day 35 or day 60 post-injection. 4 mice per group.

To test our hypothesis that CpG depleted AAVrh32.33 vectors would exhibit prolonged transgene expression, X-gal histochemical stain of gastroc tissues from WT mice injected I.M. with 1E11 GC of AAVrh32.33LacZCpG+ or AAVrh32.33LacZCpG− were assessed (FIG. 8). As expected, X-gal stain of WT AAVrh32.33LacZCpG+ transduced muscle exhibited a steady loss of detectable βgal expression. Conversely, the muscle sections from CpG depleted AAVrh32.33LacZ transduced mice displayed robust and stable transgene expression. Hence, the steady loss of LacZ transgene expression following AAVrh32.33LacZ gene transfer is dependent on vector genome CpG motifs.

J. Evidence of Hypertrophy in AAVrh32.33LacZCpG+ Transduced Muscle

Figure 9A:
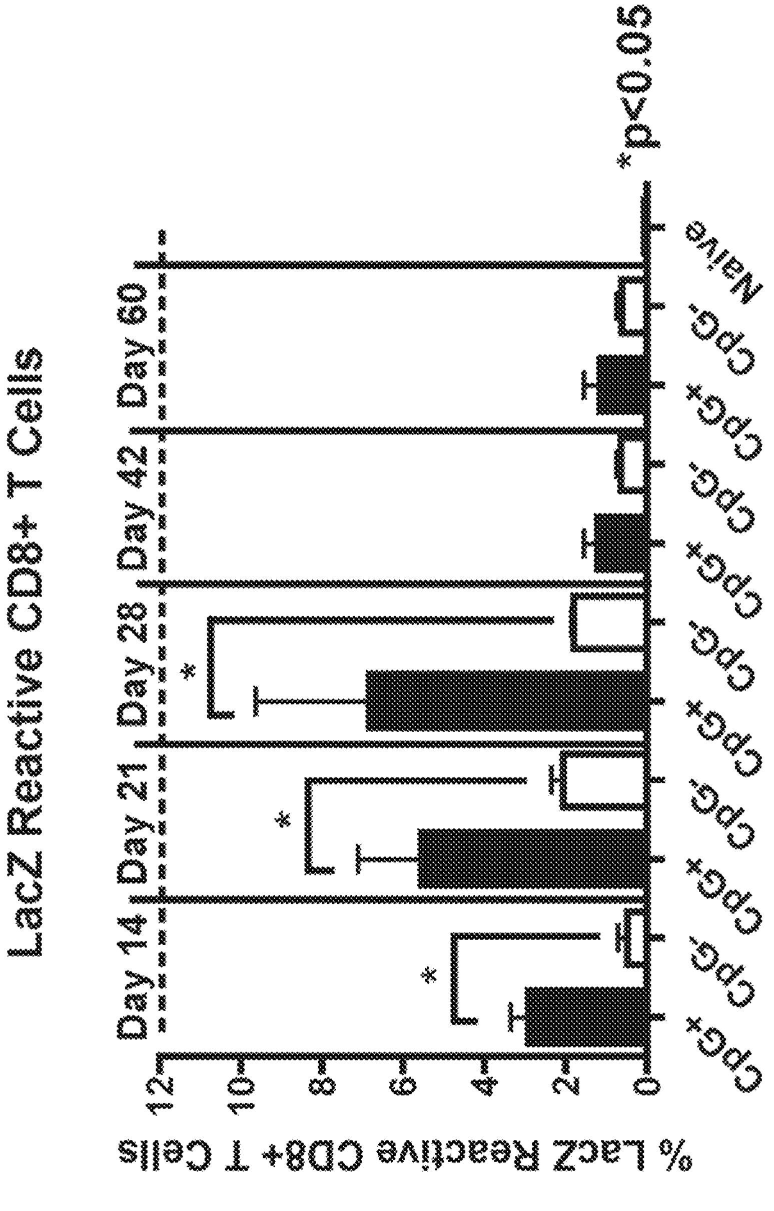
FIG. 9A is a bar chart illustrating the percentage of LacZ reactive CD8+ T cells in wild-type mice that were injected I.M. with $1\times10^{11}$ GC of AAVrh32.33LacZCpG+ or CpG− vectors. Lymphocytes from the mice were isolated from whole blood at various time points post-injection, i.e., days 14, 21, 28, 42 and 60. Lymphocytes were subsequently stained using the PE-conjugated H-$2K^b$-ICPMYARV tetramer together with a FITC-conjugated anti-CD8 Ab to determine the percentage of LacZ-specific CD8+ T cells in the total CD8+ T cell population. Results represent the mean+/−SEM of tetramer positive cells from at least n=3 recipients per group.
Figures 9B, 9C, 9D:
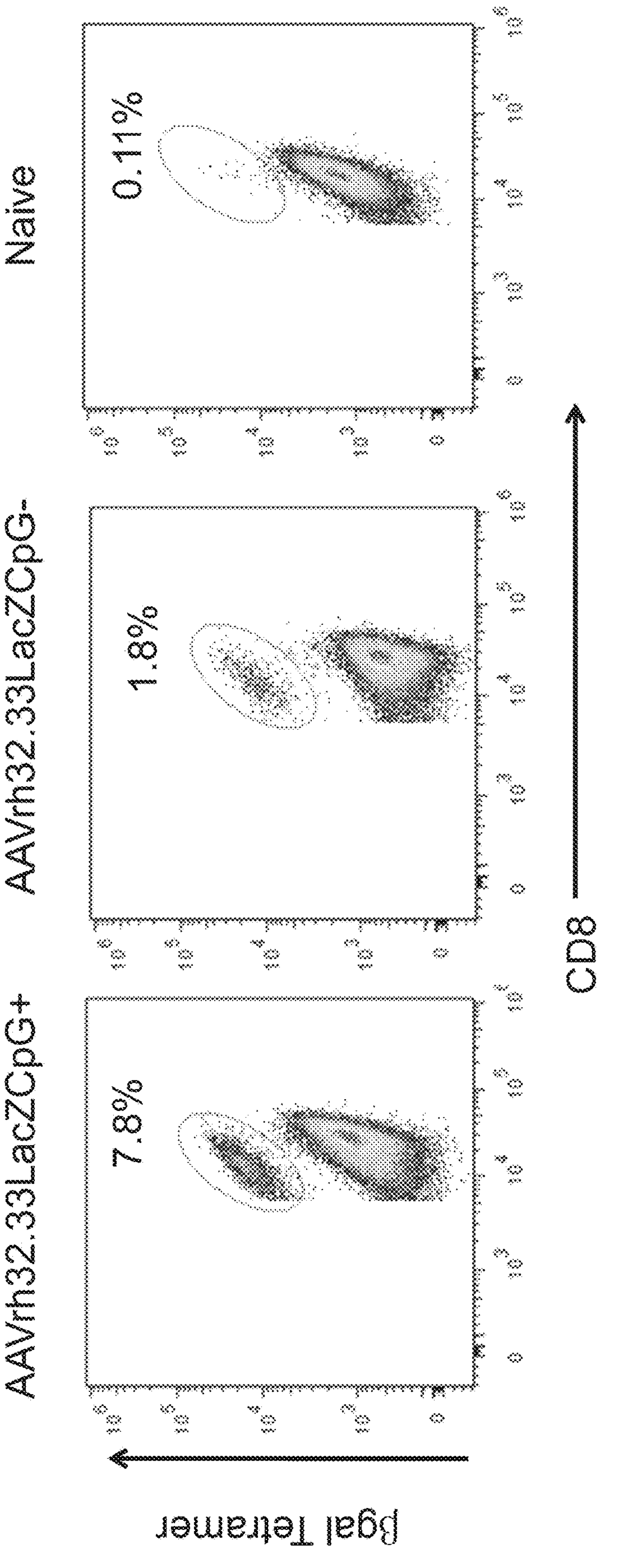
FIGS. 9B-9D are scattergrams illustrating the results of the same experiment as described in FIG. 9A.
Figure 9E:
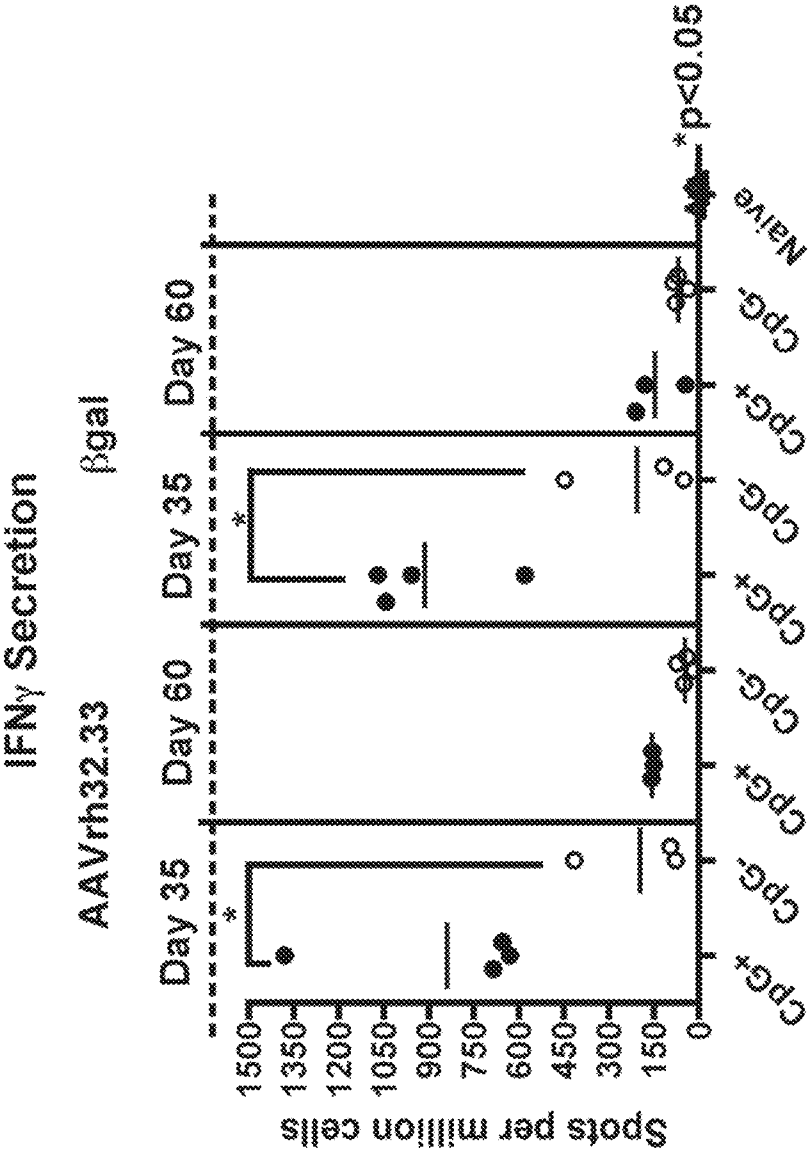
FIG. 9E is a bar chart showing gamma interferon (IFNγ) levels for wild-type mice on days 35 and 60 following intramuscular injection with $1\times10^{11}$ GC of AAVrh32.33LacZCpG+ or AAVrh32.33LacZCpG− vectors. Results represent the mean+/−SEM of cytokine-producing cells that are reactive toward transgene (nLacZ) and AAVrh32.33 capsid antigen from at least n=3 per group.

Acute and chronic inflammatory responses are strongly implicated in the induction of a pro-fibrotic environment [Faust, S. M., et al, 2009, J of Immunol 183: 7297-7803]. This inflammatory response stimulates collagen deposition and is commonly associated with the development of cellular hypertrophy. To investigate the impact of TLR9 signaling and the development of hypertrophy following intramuscular AAV gene transfer, gastroc tissue from AAVrh32.33LacZCpG+ or CpG− vector transduced mice was weighed and compared to total body weight (FIG. 9). A statistically significant increase in muscle weight was observed in AAAVrh32.33CpG+ compared to CpG depleted vector transduced mice. These data reveal the association of AAVrh32.33CpG+ gene transfer and TLR9 stimulated inflammation in the development of muscle hypertrophy.

K. CpG Depletion Significantly Reduces the Percentage of LacZ Reactive CD8+ T Cells and T Cell Effector Function Transgene stability observed in the AAVrh32.33LacZCpG− transduced muscle sections (FIG. 8) strongly suggests an abrogated adaptive immune response toward transgene and capsid antigen. To assess the requirement for CpG motifs in the induction of an adaptive immune response toward AAVrh32.33, MHC I tetramer stain and ELISPOT assays were used to quantify transgene reactive CD8+ T cells and primed transgene and capsid responsive IFNγ-producing cells as described above (FIG. 9). Mice that received the CpG depleted AAVrh32.33LacZ vector exhibited a significant reduction in the percentage of LacZ responsive CD8+ T cell population compared to control mice (FIG. 9A). Furthermore, a significant decrease in primed transgene and capsid antigen reactive Th1 responses were observed in mice that received the AAVrh32.33CpG− but not CpG+ vector (9B). These findings indicate the ability of a CpG depleted vector to escape immunoreactivity following gene transfer.

Figure 10:
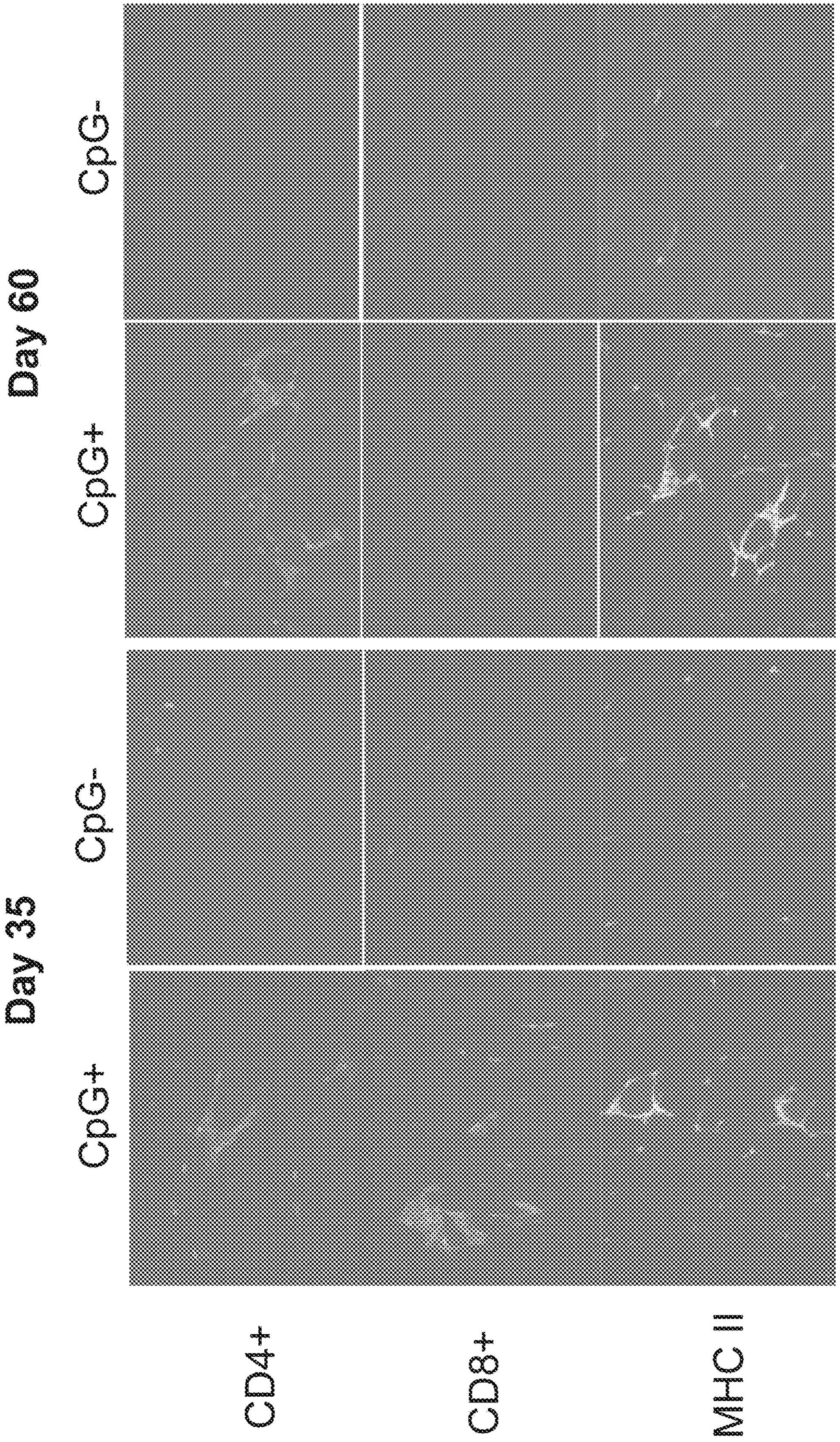
FIG. 10 provides photographs of representative muscle sections harvested from WT mice that received I.M. injection of $1\times10^{11}$ GC of AAVrh32.33nLacZCpG+ or CpG− vector. Sections from days 35 and 60 following vector administration were stained with anti-CD4 and anti-CD8 Ab and examined by fluorescent microscopy.
Figure 15A:
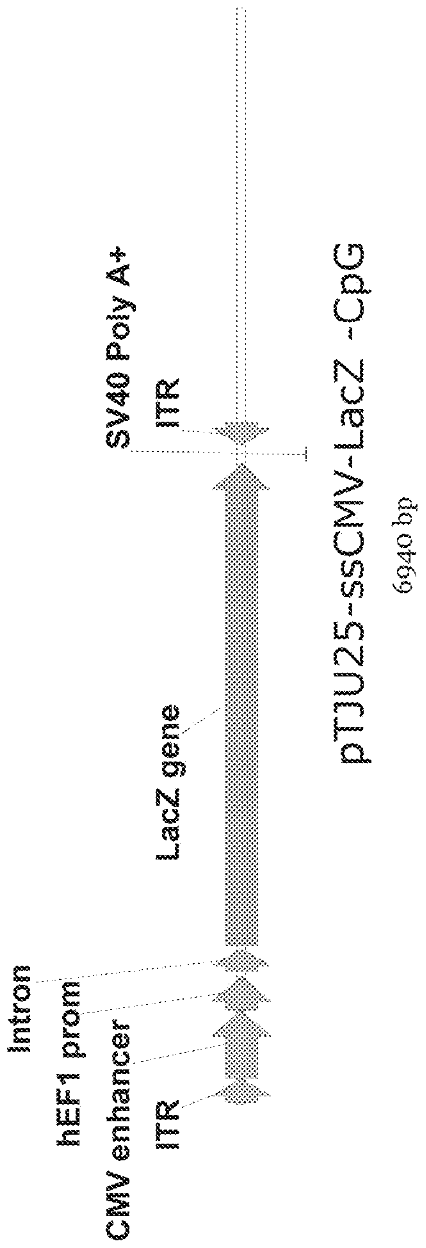
FIGS. 15A-15C provides diagrams of three pTJU vectors containing CpG depleted ITRs, CpG (−) transgenes (LacZ, firefly luciferase and human S100A1) and CpG (−) control elements.
Figure 15B:
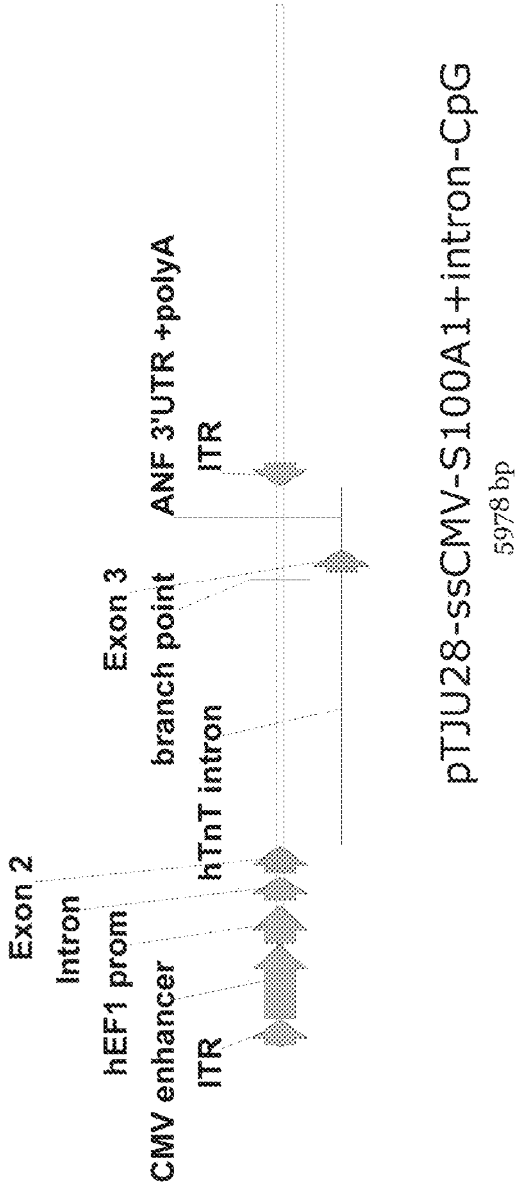
Figure 15C:
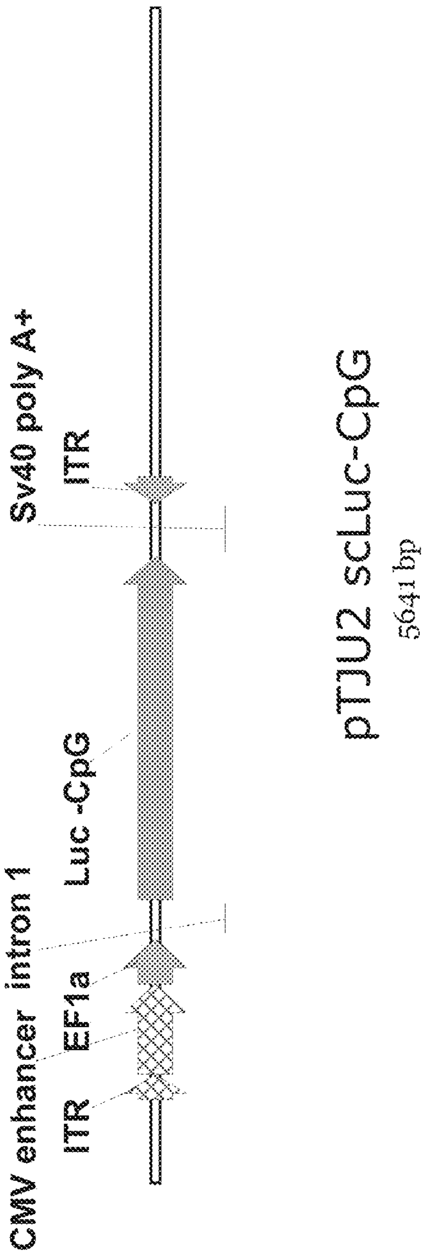
Figure 16:
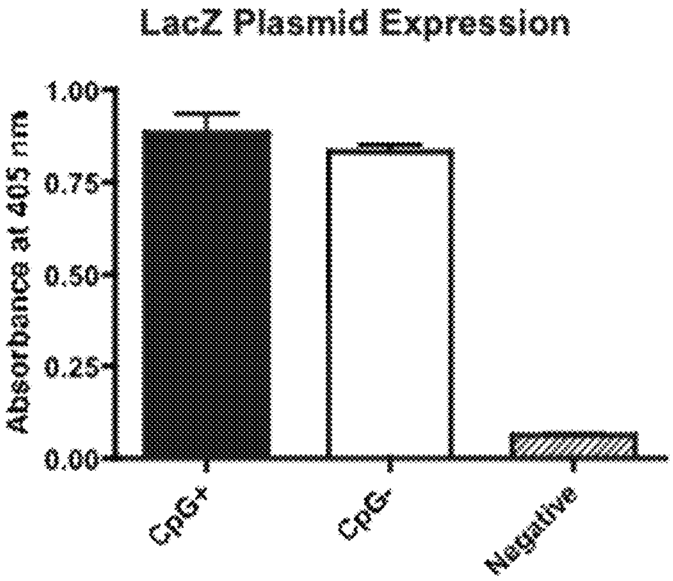
FIG. 16 is a chart showing comparable LacZ plasmid expression for CpG+ and CpG−AAV vector constructs. HeLa cells were transfected with CpG+ and CpG− AAV expression plasmids. Four days post transfection cells were assayed for β-galactosidase activity using the mammalian β-galactosidase assay kit as instructed for adherent cells. Absorbance was measured at 405 nm on a TECAN® Infinite M1000 PRO plate reader.

L. CpG Depleted AAVrh32.33LacZ Vector Gene Transfer Corresponds with Minimal Cellular Infiltrate and MHC II Expression Minimal cellular infiltrate and MHC II expression was revealed in muscle sections in the absence of TLR9 signaling following AAVrh32.33nLacZ gene transfer (FIGS. 3 and 5). These data are consistent with a TLR9 dependent mechanism of cellular infiltrate and MHC II skeletal muscle gene induction in response to the immunogenic AAV vector. If TLR9 signaling is both necessary and significant for these phenomenon, it is reasonable to suggest that CpG depleted AAVrh32.33LacZ vectors should exhibit similar histological findings to TLR9KO mice. To test this hypothesis, $1\times10^{11}$ GC of AAVrh32.33LacZCpG+ and CpG− vectors were injected intramuscularly and muscle sections were stained with anti-CD4, anti-CD8 and anti-MHC II Ab (FIG. 10). Consistent with our theory, muscle transduced with AAVrh32.33CpG-vector revealed minimal cellular infiltrate and MHC II expression compared to AAVrh32.33CpG+ transduced muscle. These data reveal the ability of CpG depleted AAV vectors to establish long-term transgene expression (FIG. 8), evade immune activation (FIG. 9), prevent the infiltration of effector T cells, and subvert the induction of skeletal muscle MHC II expression (FIG. 10).

Example 2

To measure LacZ expression of RhCpG+ and CpG− constructs, HeLa cells were transfected with CpG+ and CpG− AAV expression plasmids. Four days post transfection cells were assayed for β-galactosidase activity using the Mammalian 3-galactosidase assay kit as instructed for adherent cells. Absorbance was measured at 405 nm on a TECAN Infinite M1000 PRO plate reader. CpG+ and CpG− AAV vector constructs exhibited comparable LacZ plasmid expression. These data demonstrate that transgene loss in the skeletal muscle of RhCpG+ gene transferred is not due to differential 3-gal expression levels at the plasmid level.

To assess transgene stability and cellular infiltrate at an early kinetic time point, mice were injected intramuscularly with $1\times10^{11}$ GC of RhCpG+ or RhCpG− vector. 14 days post vector injection, gastrocnemius was harvested and skeletal muscle cryosections were stained with CD4 or CD8 monoclonal antibody (MAb) as well as X-gal. Stable transgene expression and minimal cellular infiltrate was observed in animals that receive RhCpG− vector. This indicates that reduced cellular immunity is observed as early as day 14 post vector transduction.

To examine adaptive immunity toward AAV associated antigen, splenocytes were harvested 7 and 14 days post intramuscular injection of RhCpG+ or RhCpG−. ELISPOT analysis was performed to quantify spots of IFNγ per million cells. Similar Th1 responses were observed at the early time point. In contrast, a robust Th1 response toward transgene antigen is observed only in the RhCpG+ vector transduced animals at day 14. These data demonstrate suppressed Th1 responses following RhCpG− administration at an early kinetic time point.

To determine whether tolerance is induced toward the β-gal transgene following RhCpG− gene transfer, mice were injected with $1\times10^{11}$ GC of RhCpG+ or RhCpG− in the right gastrocnemius muscle. 60 days post primary administration, mice were injected in the contralateral muscle with $1\times10^{11}$ GC of RhCpG+. Both right and left gastrocnemius tissue was harvested and muscle cryosections were stained with CD4/CD8 MAb as well as X-gal 35 days post-secondary injection. Transgene expression and minimal cellular infiltrate was exhibited in the right gastrocnemius of the RhCpG− gene transferred mice indicating a localized tolerance in the skeletal muscle even following an immunogenic vector administration.

Figure 17:
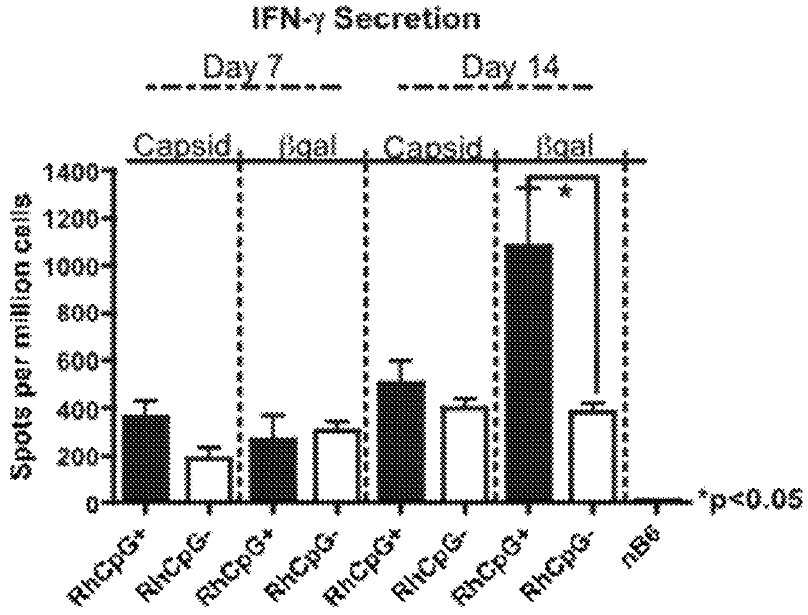
FIG. 17 is a chart showing significantly reduced Th1 responses in mice that receive RhCpG− vector on day 14 post administration. Splenocytes were harvested 7 and 14 days intramuscular injection of RhCpG+ or RhCpG− vector. ELISPOT was performed to quantify spots of IFN-gamma per million cells. Transgene reactive Th1 responses are similar between RhCpG+ and RhCpG− injected mice on day 7 but significantly reduced in RhCpG− gene transferred mice on day 14.

To analyze the Th1 response in the animals that receive a secondary injection of RhCpG+, mice were injected with RhCpG+ or RhCpG− in the right gastrocnemius muscle and 60 days post primary administration, injected in the contralateral muscle with RhCpG+(FIG. 17). Splenocytes were harvested 35 days post-secondary administrations and ELISPOT was performed to quantify spots of IFNγ per million cells. Interestingly, comparable Th1 responses in mice gene transferred initially with RhCpG+ or RhCpG− vector and readministered RhCpG+ vector, even in the presence of localized tolerance in the skeletal muscle of RhCpG− transduced animals. These data suggests that even in the presence of transgene reactive T cells, a factor localized in the skeletal muscle of mice administered the CpG depleted vector prevents the extinguishment of β-gal expression.

All publications cited in this specification are incorporated herein by reference, is U.S. Patent Application No. 61/785,368, filed Mar. 14, 2013. The sequence listing filed herewith, file "UPN_Y6335US_ST25.txt", is hereby incorporated by reference. While the invention has been described with reference to a particularly preferred embodiment, it will be appreciated that modifications can be made without departing from the spirit of the invention. Such modifications are intended to fall within the scope of the appended claims.

The invention claimed is:

1. A recombinant adeno-associated viral (AAV) vector comprising an AAV capsid and a deoxyribonucleic acid molecule comprising a 5' AAV inverted terminal repeat (ITR) sequence, a 3' AAV ITR sequence, at least one exogenous sequence and at least one regulatory sequence, wherein the at least one regulatory sequence controls the expression of an RNA or protein product of the exogenous sequence, wherein the deoxyribonucleic acid molecule is packaged within the AAV capsid, wherein both the exogenous sequence and the regulatory sequence are modified to reduce the number of CpG di-nucleotides, such that the vector has a reduced toll-like receptor 9-mediated innate immune response in a subject when compared to an unmodified AAV vector, and wherein each of the 5' AAV ITR sequence and the 3' AAV ITR sequence is a wild-type AAV ITR, wherein the at least one regulatory sequence is selected from the group consisting of a promoter, an enhancer, an intron, a microRNA and a polyA signal sequence.

2. The recombinant AAV vector according to claim 1, wherein the deoxyribonucleic acid molecule is deleted of functional AAV capsid coding sequences and functional AAV rep coding sequences.

3. The recombinant AAV vector according to claim 1, wherein the at least one regulatory sequence is CpG-free.

4. The recombinant AAV vector according to claim 3, wherein the at least one regulatory sequence is a polyA signal sequence.

5. The recombinant AAV vector according to claim 1, wherein the 5' AAV ITR is selected from the group consisting of a wild-type AAV2 ITR and a wild-type AAV5 ITR.

6. The recombinant AAV vector according to claim 1, wherein the 3' AAV ITR is selected from the group consisting of a wild-type AAV2 ITR and a wild-type AAV5 ITR.

7. The recombinant AAV vector according to claim 1, wherein any untranslated regions and/or any vector DNA sequences are modified to reduce or eliminate the number of CpG dinucleotides.

8. The recombinant AAV vector according to claim 1, wherein the number of CpG di-nucleotides in the deoxyribonucleic acid molecule is reduced by at least 30% as compared to an unmodified deoxyribonucleic acid molecule.

9. The recombinant AAV vector according to claim 1, wherein the AAV vector retains at least 95% of a protein expression level as compared to an unmodified AAV vector.

10. A pharmaceutical composition comprising the recombinant AAV vector according to claim 1 and a pharmaceutically acceptable carrier.

11. The composition according to claim 10, wherein said composition is formulated for parenteral delivery.

12. The composition according to claim 11, wherein the parenteral delivery comprises delivery to the lung, delivery to the liver, delivery to a skeletal muscle, delivery to the eye, delivery to the heart, intratracheal delivery, intraarterial delivery, intraocular delivery, intravenous delivery, intramuscular delivery, subcutaneous delivery or intradermal delivery.

13. The composition according to claim 10, wherein said composition is formulated for intramuscular delivery.

14. The composition according to claim 10, wherein the composition is formulated for oral delivery, delivery via inhalation or intranasal delivery.

15. The composition according to claim 10, wherein the composition is formulated for systemic delivery.

16. The composition according to claim 10, wherein the composition is formulated for delivery to a target organ.

17. The composition according to claim 16, wherein the target organ is central nervous system.

18. The recombinant AAV vector according to claim 1, wherein the deoxyribonucleic acid molecule comprises a synthetically generated deoxyribonucleic acid sequence.

19. The recombinant AAV vector according to claim 1, wherein said AAV vector comprises a capsid selected from the group consisting of AAV1, AAV2, AAV3A, AAV3B, AAV4, AAV5, AAV6, AAV7, AAV8, AAV9, AAV10, AAV11, AAV12, rh10, and rh32/33.

20. The recombinant AAV vector according to claim 1, wherein the AAV vector is a self-complementary AAV vector.

21. The recombinant AAV vector according to claim 1, wherein the AAV vector is a single-stranded AAV vector.

22. The recombinant AAV vector according to claim 1, wherein the AAV vector retains at least 75% of the protein expression level as compared to an unmodified AAV vector.

23. The recombinant AAV vector according to claim 1, wherein the AAV vector retains at least 85% of the protein expression level as compared to an unmodified AAV vector.

24. The recombinant AAV vector according to claim 1, wherein the deoxyribonucleic acid molecule retains the ability to fuse at its ends via inverted terminal repeats to form circular, episomal forms and does not integrate into the genome.

25. The recombinant AAV vector according to claim 1, wherein the 5' AAV ITR and the 3' AAV ITR each contain 16 CpG dinucleotides.

26. The recombinant AAV vector according to claim 1, wherein the at least one regulatory sequence is a polyA signal sequence.

27. A recombinant adeno-associated viral (AAV) vector comprising an AAV capsid and a deoxyribonucleic acid molecule comprising a 5' AAV inverted terminal repeat (ITR) sequence, a 3' AAV ITR sequence, at least one exogenous sequence and at least one regulatory sequence, wherein the at least one regulatory sequence controls the expression of an RNA or protein product of the exogenous sequence, wherein the deoxyribonucleic acid molecule is packaged within the AAV capsid, wherein both the exogenous sequence and the regulatory sequence are CpG-free and the 5' AAV ITR sequence and the 3' AAV ITR sequence each is independently selected from the group consisting of a wild-type AAV2 ITR, a wild-type AAV5 ITR, and a CpG-modified ITR, wherein the CpG modified ITR has a reduced number of CpG di-nucleotides relative to a wild-type AAV2 ITR or a wild-type AAV5 ITR and wherein the CpG modified ITR is not CpG-free, wherein the at least one regulatory sequence is selected from the group consisting of a promoter, an enhancer, an intron, a microRNA and a polyA signal sequence.

28. The recombinant AAV vector according to claim 27, wherein the deoxyribonucleic acid molecule retains the ability to fuse at its ends via inverted terminal repeats to form circular, episomal forms and does not integrate into the genome.

29. The recombinant AAV vector according to claim 27, wherein each of the 5' AAV ITR sequence and the 3' AAV ITR sequence are CpG modified ITRs.

30. The recombinant AAV vector according to claim 29, wherein the 5' AAV ITR sequence and the 3' AAV ITR sequence each contain 8 CpG dinucleotides.

31. The recombinant AAV vector according to claim 29, wherein the recombinant viral genome retains the ability to fuse at its ends via inverted terminal repeats to form circular, episomal forms and does not integrate into the genome.

32. A recombinant adeno-associated viral (AAV) vector comprising an AAV capsid and a deoxyribonucleic acid molecule comprising a 5' AAV2 inverted terminal repeat (ITR) sequence, a 3' AAV2 ITR sequence, at least one exogenous sequence and at least one regulatory sequence,
- wherein the at least one regulatory sequence controls the expression of an RNA or protein product of the exogenous sequence,
- wherein the deoxyribonucleic acid molecule is packaged within the AAV capsid,
- wherein both the exogenous sequence and the regulatory sequence are CpG-free, and
- wherein the 5' AAV2 ITR sequence and the 3' AAV2 ITR sequence each comprise 16 CpG di-nucleotides, wherein the at least one regulatory sequence is selected from the group consisting of a promoter, an enhancer, an intron, a microRNA and a polyA signal sequence.

33. A recombinant adeno-associated viral (AAV) vector comprising an AAV capsid and a deoxyribonucleic acid molecule comprising a 5' AAV inverted terminal repeat (ITR) sequence, a 3' AAV ITR sequence, at least one exogenous sequence and at least one regulatory sequence,
- wherein the at least one regulatory sequence controls the expression of an RNA or protein product of the exogenous sequence and wherein the at least one regulatory sequence is selected from the group consisting of a promoter, an enhancer, an intron, a microRNA and a polyA signal sequence,
- wherein the deoxyribonucleic acid molecule is packaged within the AAV capsid,
- wherein both the exogenous sequence and the regulatory sequence are modified to reduce the number of CpG di-nucleotides, such that the vector has a reduced toll-like receptor 9-mediated innate immune response in a subject when compared to an unmodified AAV vector, and
- wherein the 5' AAV ITR sequence and the 3' AAV ITR sequence each is independently selected from the group consisting of a wild-type AAV ITR, a wild-type AAV ITR, and a CpG-modified ITR, wherein the CpG-modified ITR has a reduced number of CpG di-nucleotides relative to a wild-type AAV ITR and wherein the CpG-modified ITR is not CpG-free.

34. The recombinant AAV vector according to claim 33, wherein the exogenous sequence is CpG-free.

35. The recombinant AAV vector according to claim 33, wherein the at least one regulatory sequence is CpG-free.

36. The recombinant AAV vector according to claim 33, wherein both the exogenous sequence and the at least one regulatory sequence are CpG-free.

37. The recombinant AAV vector according to claim 36, wherein the at least one regulatory sequence is a polyA signal sequence.

* * * * *

SEQUENCE LISTING

```
<160> NUMBER OF SEQ ID NOS: 14

<210> SEQ ID NO 1
<211> LENGTH: 145
<212> TYPE: DNA
<213> ORGANISM: adeno-associated virus 2

<400> SEQUENCE: 1

aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag agagggagtg gccaa                                          145


<210> SEQ ID NO 2
<211> LENGTH: 136
<212> TYPE: DNA
<213> ORGANISM: Artificial sequence
<220> FEATURE:
<223> OTHER INFORMATION: Synthetic (CPG Depleted ITR)

<400> SEQUENCE: 2

ggccagtccc tctctgcgcg ctcgctcgct cactgaggcc tggataccaa aggtatccag     60

actcctaggc tttgcctagg aggcctcagt gagcgagcga gcgcgcagag agggagtggc    120

caactccatc actagg                                                    136


<210> SEQ ID NO 3
<211> LENGTH: 123
<212> TYPE: DNA
```

<213> ORGANISM: Artificial Sequence
<220> FEATURE:
<223> OTHER INFORMATION: Synthetic sequence (consensus AAV ITR)
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(67)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t

<400> SEQUENCE: 3
ggccantccc tctctgcgcg ctcgctcgct cactgaggcc nggnnaccaa aggtnnccng 60
acnccnnggc tttgccnngg nggcctcagt gagcgagcga gcgcgcagag agggagtggc 120
caa 123

<210> SEQ ID NO 4
<211> LENGTH: 138
<212> TYPE: DNA
<213> ORGANISM: adeno-associated virus 2

<400> SEQUENCE: 4
tgatggagtt ggccactccc tctctgcgcg ctcgctcgct cactgaggcc ggccccgggg 60
caaagcccgg gcgtcgggcg acctttggtc gccccggcct cagtgagcga gcgagcgcgc 120
agagagggag tggggcaa 138

<210> SEQ ID NO 5
<211> LENGTH: 125
<212> TYPE: DNA
<213> ORGANISM: Artificial Sequence
<220> FEATURE:
<223> OTHER INFORMATION: Synthetic Sequence (AAV ITRs with GpG outside
of RBS)

<400> SEQUENCE: 5
ttggccactc cctctctgcg cgctcgctcg ctcactgagg cctcctaggc aaagcctagg 60
agtctggaga cctttggtat ccaggcctca gtgagcgagc gagcgcgcag agagggactg 120
gccaa 125

<210> SEQ ID NO 6
<211> LENGTH: 3072
<212> TYPE: DNA
<213> ORGANISM: Escherichia coli

<400> SEQUENCE: 6
atgaccatga ttacggattc actggccgtc gttttacaac gtcgtgactg ggaaaaccct 60
ggcgttaccc aacttaatcg ccttgcagca catccccctt tcgccagctg gcgtaatagc 120
gaagaggccc gcaccgattg cccttcccaa cagttgcgca gcctgaatgg cgaatggcgc 180
tttgcctggt ttccggcacc agaagcggtg ccggaaagct ggctggagtg cgatcttcct 240
gaggccgata ctgtcgtcgt cccctcaaac tggcagatgc acggttacga tgcgcccatc 300
tacaccaacg tgacctatcc cattacggtc aatccgccgt ttgttcccac ggagaatccg 360
acgggttgtt actcgctcac atttaatgtt gatgaaagct ggctacagga aggccagacg 420
cgaattattt ttgatggcgt taactcggcg tttcatctgt ggtgcaacgg gcgctgggtc 480
ggttacggcc aggacagtcg tttgccgtct gaatttgacc tgagcgcatt tttacgcgcc 540
ggagaaaacc gcctcgcggt gatggtgctg cgctggagtg acggcagtta tctggaagat 600
caggatatgt ggcggatgag cggcattttc cgtgacgtct cgttgctgca taaaccgact 660
acacaaatca gcgatttcca tgttgccact cgctttaatg atgatttcag ccgcgctgta 720
ctggaggctg aagttcagat gtgcggcgag ttgcgtgact acctacgggt aacagtttct 780
ttatggcagg gtgaaacgca ggtcgccagc ggcaccgcgc ctttcggcgg tgaaattatc 840
gatgagcgtg gtggttatgc cgatcgcgtc acactacgtc tgaacgtcga aaacccgaaa 900
ctgtggagcg ccgaaatccc gaatctctat cgtgcggtgg ttgaactgca caccgccgac 960
ggcacgctga ttgaagcaga agcctgcgat gtcggtttcc gcgaggtgcg gattgaaaat 1020
ggtctgctgc tgctgaacgg caagccgttg ctgattcgag gcgttaaccg tcacgagcat 1080
catcctctgc atggtcaggt catggatgag cagacgatgg tgcaggatat cctgctgatg 1140
aagcagaaca actttaacgc cgtgcgctgt tcgcattatc cgaaccatcc gctgtggtac 1200
acgctgtgcg accgctacgg cctgtatgtg gtggatgaag ccaatattga aacccacggc 1260
atggtgccaa tgaatcgtct gaccgatgat ccgcgctggc taccggcgat gagcgaacgc 1320
gtaacgcgaa tggtgcagcg cgatcgtaat cacccgagtg tgatcatctg gtcgctgggg 1380
aatgaatcag gccacggcgc taatcacgac gcgctgtatc gctggatcaa atctgtcgat 1440
ccttcccgcc cggtgcagta tgaaggcggc ggagccgaca ccacggccac cgatattatt 1500
tgcccgatgt acgcgcgcgt ggatgaagac cagcccttcc cggctgtgcc gaaatggtcc 1560
atcaaaaaat ggctttcgct acctggagag acgcgcccgc tgatcctttg cgaatacgcc 1620
cacgcgatgg gtaacagtct tggcggtttc gctaaatact ggcaggcgtt tcgtcagtat 1680
ccccgtttac agggcggctt cgtctgggac tgggtggatc agtcgctgat taaatatgat 1740
gaaaacggca acccgtggtc ggcttacggc ggtgattttg gcgatacgcc gaacgatcgc 1800
cagttctgta tgaacggtct ggtctttgcc gaccgcacgc cgcatccagc gctgacggaa 1860
gcaaaacacc agcagcagtt tttccagttc cgtttatccg ggcaaaccat cgaagtgacc 1920
agcgaatacc tgttccgtca tagcgataac gagctcctgc actggatggt ggcgctggat 1980
ggtaagccgc tggcaagcgg tgaagtgcct ctggatgtcg ctccacaagg taaacagttg 2040
attgaactgc ctgaactacc gcagccggag agcgccgggc aactctggct cacagtacgc 2100
gtagtgcaac cgaacgcgac cgcatggtca gaagccgggc acatcagcgc ctggcagcag 2160

-continued tggcgtctgg cggaaaacct cagtgtgacg ctccccgccg cgtcccacgc catcccgcat 2220
ctgaccacca gcgaaatgga tttttgcatc gagctgggta ataagcgttg gcaatttaac 2280
cgccagtcag gctttctttc acagatgtgg attggcgata aaaaacaact gctgacgccg 2340
ctgcgcgatc agttcacccg tgcaccgctg gataacgaca ttggcgtaag tgaagcgacc 2400
cgcattgacc ctaacgcctg ggtcgaacgc tggaaggcgg cgggccatta ccaggccgaa 2460
gcagcgttgt tgcagtgcac ggcagataca cttgctgatg cggtgctgat tacgaccgct 2520
cacgcgtggc agcatcaggg gaaaacctta tttatcagcc ggaaaaccta ccggattgat 2580
ggtagtggtc aaatggcgat taccgttgat gttgaagtgg cgagcgatac accgcatccg 2640
gcgcggattg gcctgaactg ccagctggcg caggtagcag agcgggtaaa ctggctcgga 2700
ttagggccgc aagaaaacta tcccgaccgc cttactgccg cctgttttga ccgctgggat 2760
ctgccattgt cagacatgta taccccgtac gtcttcccga gcgaaaacgg tctgcgctgc 2820
gggacgcgcg aattgaatta tggcccacac cagtggcgcg gcgacttcca gttcaacatc 2880
agccgctaca gtcaacagca actgatggaa accagccatc gccatctgct gcacgcggaa 2940
gaaggcacat ggctgaatat cgacggtttc catatgggga ttggtggcga cgactcctgg 3000
agcccgtcag tatcggcgga attccagctg agcgccggtc ggtaccatta ccagttggtc 3060
tggtgtcaaa aa 3072

<210> SEQ ID NO 7
<211> LENGTH: 3056
<212> TYPE: DNA
<213> ORGANISM: Artificial sequence
<220> FEATURE:
<223> OTHER INFORMATION: Synthetic sequence (CpG-depleted LacZ)
<220> FEATURE:
<221> NAME/KEY: misc_feature
<222> LOCATION: (7)..(8)
<223> OTHER INFORMATION: n is a, c, g, or t

<400> SEQUENCE: 7
atggacnncc tgttgtgctg caaaggagag actgggagaa ccctggagtg acccagctca 60
acagactggc tgcccaccct ccctttgcct cttggaggaa ctctgaggaa gccaggacag 120
acaggcccag ccagcagctc aggtctctca atggagagtg gaggtttgcc tggttccctg 180
cccctgaagc tgtgcctgag tcttggctgg agtgtgacct cccagaggct gacactgttg 240
tggtgcccag caactggcag atgcatggct atgatgcccc catctacacc aatgtcacct 300
accccatcac tgtgaacccc ccttttgtgc ccactgagaa ccccactggc tgctacagcc 360
tgaccttcaa tgttgatgag agctggctgc aagaaggcca gaccaggatc atctttgatg 420
gagtcaactc tgccttccac ctctggtgca atggcaggtg ggttggctat ggccaagaca 480
gcaggctgcc ctctgagttt gacctctctg ccttcctcag agctggagag aacaggctgg 540
ctgtcatggt gctcaggtgg tctgatggca gctacctgga agaccaagac atgtggagga 600
tgtctggcat cttcagggat gtgagcctgc tgcacaagcc caccacccag atttctgact 660
tccatgttgc caccaggttc aatgatgact tcagcagagc tgtgctggag gctgaggtgc 720
agatgtgtgg agaactcaga gactacctga gagtcacagt gagcctctgg caaggtgaga 780
cccaggtggc ctctggcaca gccccctttg gaggagagat cattgatgag agaggaggct 840
atgctgacag agtcaccctg aggctcaatg tggagaaccc caagctgtgg tctgctgaga 900
tccccaacct ctacagggct gttgtggagc tgcacactgc tgatggcacc ctgattgaag 960

-continued ctgaagcctg tgatgttgga ttcagagaag tcaggattga gaatggcctg ctgctgctca 1020
atggcaagcc tctgctcatc aggggagtca acaggcatga gcaccaccct ctgcatggac 1080
aagtgatgga tgaacagaca atggtgcaag atatcctgct aatgaagcag aacaacttca 1140
atgctgtcag gtgctctcac taccccaacc accctctctg gtacaccctg tgtgacaggt 1200
atggcctgta tgttgttgat gaagccaaca ttgagacaca tggcatggtg cccatgaaca 1260
ggctcacaga tgaccccagg tggctgcctg ccatgtctga gagagtgacc aggatggtgc 1320
agagagacag gaaccacccc tctgtgatca tctggtctct gggcaatgag tctggacatg 1380
gagccaacca tgatgctctc tacaggtgga tcaagtctgt tgaccccagc agacctgtgc 1440
agtatgaagg aggtggagca gacaccacag ccacagacat catctgcccc atgtatgcca 1500
gggttgatga ggaccagccc ttccctgctg tgcccaagtg gagcatcaag aagtggctct 1560
ctctgcctgg agagaccaga cctctgatcc tgtgtgaata tgcacatgca atgggcaact 1620
ctctgggagg ctttgccaag tactggcaag ccttcagaca gtaccccagg ctgcaaggag 1680
gatttgtgtg ggactgggtg gaccaatctc tcatcaagta tgatgagaat ggcaacccct 1740
ggtctgccta tggaggagac tttggtgaca cccccaatga caggcagttc tgcatgaatg 1800
gcctggtctt tgcagacagg acccctcacc ctgccctcac agaggccaag caccagcaac 1860
agttcttcca gttcaggctg tctggacaga ccattgaggt gacatctgag tacctcttca 1920
ggcactctga caatgagctc ctgcactgga tggtggccct ggatggcaag cctctggctt 1980
ctggtgaggt gcctctggat gtggcccctc aaggaaagca gctgattgaa ctgcctgagc 2040
tgcctcagcc agagtctgct ggacaactgt ggctaacagt gagggtggtt cagcccaatg 2100
caacagcttg gtctgaggca ggccacatct ctgcatggca gcagtggagg ctggctgaga 2160
acctctctgt gaccctgcct gctgcctctc atgccatccc tcacctgaca acatctgaaa 2220
tggacttctg cattgagctg ggcaacaaga gatggcagtt caacaggcag tctggcttcc 2280
tgtctcagat gtggattgga gacaagaagc agctcctcac ccctctcagg gaccaattca 2340
ccagggctcc tctggacaat gacattggag tgtctgaggc caccaggatt gacccaaatg 2400
cttgggtgga gaggtggaag gctgctggac actaccaggc tgaggctgcc ctgctccagt 2460
gcacagcaga caccctggct gatgctgttc tgatcaccac agcccatgct tggcagcacc 2520
aaggcaagac cctgttcatc agcagaaaga cctacaggat tgatggctct ggacagatgg 2580
caatcacagt ggatgtggag gttgcctctg acacacctca ccctgcaagg attggcctga 2640
actgtcaact ggcacaggtg gctgagaggg tgaactggct gggcttaggc cctcaggaga 2700
actaccctga caggctgaca gctgcctgct ttgacaggtg ggacctgcct ctgtctgaca 2760
tgtacacccc ttatgtgttc ccttctgaga atggcctgag gtgtggcacc agggagctga 2820
actatggtcc tcaccagtgg aggggagact tccagttcaa catctccagg tactctcagc 2880
aacagctcat ggaaacctct cacaggcacc tgctccatgc agaggaggga acctggctga 2940
acattgatgg cttccacatg ggcattggag gagatgactc ttggtctcct tctgtgtctg 3000
ctgagttcca gttatctgct ggcaggtacc actatcagct ggtgtggtgc cagaag 3056

<210> SEQ ID NO 8
<211> LENGTH: 1856
<212> TYPE: DNA
<213> ORGANISM: Artificial sequence
<220> FEATURE:
<223> OTHER INFORMATION: Synthetic sequence (CpG-modified human TnT
intron w S10001 exons -continued

<400> SEQUENCE: 8
gaattctgta cagtagcttc caccatgggc tctgagctgg agacagctat ggagaccctg 60
atcaatgtgt tccatgccca ctctggcaag gagggagaca agtacaagct gagcaagaag 120
gagctgaagg agctgctcca gacagagctg tctggcttcc tggatgccca gaaggtgagt 180
gccatgctgt ccccagccca gcatctccat ctcacactcc tcctggttca ctgggtcctg 240
gtaatactgg tccctgggtc cctgtcccta ttccccaaca gccccccttca gctcctgcat 300 ctgcccctgc tgcctggcct tcagcagtgt tccatgtcca cccattgacc actgcttgct 360
ggaagtgtct gagagctcct ggggctgagc agagacactt tcctggtgtt ccaaccctgg 420
gggtctccaa cacttgaggc agcagctcag tgatctgagc tggttacaag gacctggatg 480
caccaagcca agcagctcag tgatctgagc tggttacaag gaccaggatg caccaagcca 540
ggacccccag tggaagggga gtgctgccaa cagagaggtg cttctcccca catacaccca 600
aggtcctggt gtgggcacaa ttaggctgag cctcaagctc acagtctttg gagtcctatg 660
tgcactaatg agggtcttag gtgaacagac actggcaagg aaatggctta gaggacactg 720
atgctgcata ccatgagctt agacctgggc ccagtccttc cttacccacc acccccagcc 780
cctggtccct agggcctctt tgctacctaa gggaagaact tcagcttccc ctggaaggtc 840
tcctttgctg ctcctgccaa accactcctc cctgggcaag aagcccctgc tgggctggct 900
tggctacggg tactcccacc tcccaatagg agagaggctg tattgcctgg tgacagtggc 960
atggactttg gagccataat gcctgggttg aatttctacc tgtgcccctc actggctgtg 1020
tgacattggc agagttagtc cactgttcct tgcctccatt tccacatggt aacactacaa 1080
tatacttcag agggtgattg tgagggttac agagataata ctaattgtta ttattgctat 1140
agtgttccaa ccactgttcc aagcatgtcc catgggtgct cagaagagcc tggcacccac 1200
taaatgctca gcatgtcagc cattgttatg gcctctctag tcctgtgcct tccacttttt 1260
tctctttttt tggttccaca ctgaactctg caccaagcca aaggacacag atttgccaaa 1320
ctttggggca gcacctgggt ggtgcatggg gatgctactg ctcaaagggc acagcttcct 1380
gggatggtgg gcagctgggc atgggtgccc cagaggggtc tggggctggg ctgctaggag 1440
ggctccatga cacagcctcc agctttgtgc ccagctctca gaggcccttc ttatgggact 1500
ctcatatcct gaacctatta tggccctggg accccacagt gggaggccca tgaggcatcc 1560
tggaaggctt ctccttggct tctgcctgtg gtacaaggcc cctcctgtcc cttaactatc 1620
ctacccctcc tactcttcca tgctcctcct tctcctcctg cactgctgca ctcagccccc 1680
ttctccccat cccctggcca cccctgacca tcctcccttg ctctttgtcc ttccccttttt 1740 cttgcaggat gtggatgctg tggacaaggt gatgaaggag ctggatgaga atggagatgg 1800
cctgcaacaa cttcttctgg gagaacagct gatggtctgc tagctctaga ggatcc 1856

<210> SEQ ID NO 9
<211> LENGTH: 1746
<212> TYPE: DNA
<213> ORGANISM: homo sapiens

<400> SEQUENCE: 9
gagaaggcca aggagctgtg gcagagcatc tataacttgg aggcagagaa gttcgacctg 60
caggagaagt tcaagcagca gaaatatgag gtgggccgcc atgctgtccc cgcccagcat 120
ctccatctca cactcctcct ggttcactgg gtccggtaat actgctgcag gtccctgggt 180
ccctgtccct attccccaac agcccccttc agctcctgca tctgcccctg ctgcctggcc 240

-continued ttcagcagtg ttccatgtcc accgcattga cgactgcttg ctggaagtgt ctgagagctc 300
gctggggctg agcagagaca ctttcctggt gttccaaccc tgggggtctc caacacgttg 360
aggcagcagc tcagtgatct gagctggtta caaggaccag gatgcaccaa gccaggaccc 420
ccagtggaag gggagtgctg ccaacagaga ggtgcttctc cccacataca cccaaggtcc 480
tggtgtgggc acaattaggc tgagcctcaa gctcacagtc tttcggagtc ctatgtgcac 540
taatgagggt cttaggtgaa cagacaccag gcaaggaaat ggcttagagg acactgatgc 600
tgcataccgg agcttagacc tgggcgccag tccttcctta cccaccaccc ccgagccccg 660
gtcccagggc ctctttgcta cctaagggaa gaattcagct tcccctggaa ggtctccttt 720
gctgctcctg ccaaaccact cctccctggg caagaagccc ctcgctgggc aggctcaggc 780
tgcagtggct acagggtact cccacctccc aatacggaga gaggctgtat tgcctggtga 840
cagtggcatg gactttggag ccataatgcc tgggttgaat ttctacctgt gcccctcact 900
ggctgtgtga cattgggtga gttagtccac tgttccttgc ctccatttcc acaggtaaca 960
ctacaatata cttcagaggg tgattgtgag ggttacagag ataatactaa ttgttattat 1020
tgctatagtg ttccaaccac tgttccaagc atgtcccatg tattaactta ctatgccctc 1080
atagcagccc tatgggttca tatctgggaa ggtgctcagg acagagcctg gcacccacta 1140
aatgctcagc aggtgtcagc cattgttatg gcctctctag tcctgtgcct tccacttttt 1200
tctctttttt tggttccaca ctgaactctg caccggccaa caggacacag atttgccaaa 1260
ctttggggca gcaccctgca ggggtggtgc atggggatgc tactgctcaa agggcacagc 1320
ttccgggatg gtgggcagct gggcaggggt gccccagagg ggtctggggc tgggctgcta 1380
ggagggctcc atgacacagc ctccagcttt gtgcccagct ctcagaggcc cttcttatgg 1440
gactctcata tcctgaacct attatggccc tgggacccca cagtgggagg cccatgaggc 1500
atcctggaag cttctccttg gcttctgcct gtggtacacg ggcccctcct gacccttaac 1560
tatcctaacc cctcctactc ttccatgctc ctccttctcc tcctgcactg ctgcactcag 1620 ccccttctc cccatcccca ggccacctgg gacctgagcc agtcagctcc agcgttgctc 1680
tttgtccttc ccacttttct tgcagatcaa tgttctccga aacaggatca acgataacca 1740
gaaagt 1746

<210> SEQ ID NO 10
<211> LENGTH: 1700
<212> TYPE: DNA
<213> ORGANISM: Photinus pyralis

<400> SEQUENCE: 10
atggaagatg ccaaaaacat taagaagggc ccagcgccat tctacccact cgaagacggg 60
accgccggcg agcagctgca caaagccatg aagcgctacg ccctggtgcc cggcaccatc 120
gcctttaccg acgcacatat cgaggtggac attacctacg ccgagtactt cgagatgagc 180
gttcggctgg cagaagctat gaagcgctat gggctgaata caaaccatcg gatcgtggtg 240
tgcagcgaga atagcttgca gttcttcatg cccgtgttgg gtgccctgtt catcggtgtg 300
gctgtggccc cagctaacga catctacaac gagcgcgagc tgctgaacag catgggcatc 360
agccagccca ccgtcgtatt cgtgagcaag aaagggctgc catgggcatc agccagccca 420
cagtggtatt tgtgagcaag aaagggctgc aaaagatcct caacgtgcaa aagaagctac 480
cgatcataca aaagatcatc atcatggata gcaagaccga ctaccagggc ttccaaagca 540

```
tgtacacctt cgtgacttcc catttgccac ccggcttcaa cgagtacgac ttcgtgcccg    600

agagcttcga ccgggacaaa accatcgccc tgatcatgaa cagtagtggc agtaccggat    660

tgcccaaggg cgtagcccta ccgcaccgca ccgcttgtgt ccgattcagt catgcccgcg    720

accccatctt cggcaaccag atcatccccg acaccgctat cctcagcgtg gtgccatttc    780

accacggctt cggcatgttc accacgctgg gctacttgat ctgcggcttt cgggtcgtgc    840

tcatgtaccg cttcgaggag gagctattct tgcgcagctt gcaagactat aagattcaat    900

ctgccctgct ggtgcccaca ctatttagct tcttcgctaa gagcactctc atcgacaagt    960

acgacctaag caacttgcac gagatcgcca gcggcggggc gccgctcagc aaggaggtag   1020

gtgaggccgt ggccaaacgc ttccacctac caggcatccg ccagggctac ggcctgacag   1080

aaacaaccag cgccattctg atcacccccg aaggggacga caagcctggc gcagtaggca   1140

aggtggtgcc cttcttcgag gctaaggtgg tggacttgga caccggtaag acactgggtg   1200

tgaaccagcg cggcgagctg tgcgtccgtg gccccatgat catgagcggc tacgttaaca   1260

accccgaggc tacaaacgct ctcatcgaca aggacggctg gctgcacagc ggcgacatcg   1320

cctactggga cgaggacgag cacttcttca tcgtggaccg gctgaagagc ctgatcaaat   1380

acaagggcta ccaggtagcc ccagccgaac tggagagcat cctgctgcaa caccccaaca   1440

tcttcgacgc cggggtcgcc ggcctgcccg acgacgatgc cggcgagctg cccgccgcag   1500

tcgtcgtgct ggaacacggt aaaaccatga ccgagaagga gatcgtggac tatgtggcca   1560

gccaggttac aaccgccaag aagctgcgcg gtggtgttgt gttcgtggac gaggtgccta   1620

aaggactgac cggcaagttg gacgcccgca agatccgcga gattctcatt aaggccaaga   1680

agggcggcaa gatcgccgtg                                               1700
```

```
<210> SEQ ID NO 11
<211> LENGTH: 1650
<212> TYPE: DNA
<213> ORGANISM: Artificial sequence
<220> FEATURE:
<223> OTHER INFORMATION: Synthetic sequence (cpg-depleted firefly
      luciferase)

<400> SEQUENCE: 11

atggaagatg ccaaaaacat taagaagggc ccagctccat tctacccact ggaagatggg     60

acagctggag agcagctgca caaagccatg aagagatatg ccctggtgcc tggcaccatt    120

gcctttacag atgcacatat tgaggtggac attacctatg ctgagtactt tgagatgtct    180

gttagactgg cagaagctat gaagagatat gggctgaata caaaccatag gattgtggtg    240

tgctctgaga atagcttgca gttcttcatg cctgtgttgg gtgccctgtt cattggtgtg    300

gctgtggccc cagctaatga catctacaat gagagagagc tgctgaacag catgggcatc    360

agccagccca cagtggtatt tgtgagcaag aaagggctgc aaaagatcct caatgtgcaa    420

aagaagctac ccatcataca aaagatcatc atcatggata gcaagacaga ctaccagggc    480

ttccaaagca tgtatacctt tgtgacttcc catttgccac ctggcttcaa tgagtatgac    540

tttgtgcctg agagctttga cagagacaaa accattgccc tgatcatgaa cagtagtggc    600

agtacaggat tgcccaaggg agtagcccta cctcacagaa cagcttgtgt cagattcagt    660

catgccaggg accccatctt tggcaaccag atcatccctg acacagctat cctctctgtg    720

gtgccatttc atcatggctt tggcatgttc accaccctgg gctacttgat ctgtggcttt    780

agggtggtgc tcatgtatag atttgaggag gagctattct tgaggagctt gcaagactat    840
```

```
aagattcaat ctgccctgct ggtgcccaca ctatttagct tctttgctaa gagcactctc    900

attgacaagt atgacctaag caacttgcat gagattgcct ctggaggggc ccctctcagc    960

aaggaggtag gtgaggctgt ggccaaaagg ttccacctac caggcatcag gcagggctat   1020

ggcctgacag aaacaacctc tgccattctg atcacccctg aaggggatga caagcctgga   1080

gcagtaggca aggtggtgcc cttctttgag gctaaggtgg tggacttgga cacaggtaag   1140

acactgggtg tgaaccagag aggagagctg tgtgtcaggg gccccatgat catgtctggc   1200

tatgttaaca accctgaggc tacaaatgct ctcattgaca aggatggctg gctgcactct   1260

ggagacattg cctactggga tgaggatgag cacttcttca ttgtggacag gctgaagagc   1320

ctgatcaaat acaagggcta ccaggtagcc ccagctgaac tggagagcat cctgctgcaa   1380

caccccaaca tctttgatgc tggggtggct ggcctgcctg atgatgatgc aggagagctg   1440

ccagcagcag ttgtggtgct ggaacatggt aaaaccatga cagagaagga gattgtggac   1500

tatgtggcca gccaggttac aacagccaag aagctgagag gtggtgttgt gtttgtggat   1560

gaggtgccta aaggactgac aggcaagttg gatgccagaa agatcagaga gattctcatt   1620

aaggccaaga agggaggcaa gattgctgtg                                    1650


<210> SEQ ID NO 12
<211> LENGTH: 5978
<212> TYPE: DNA
<213> ORGANISM: Artificial sequence
<220> FEATURE:
<223> OTHER INFORMATION: Synthetic sequence (CpG-modified vector)

<400> SEQUENCE: 12

gaattcttgg ccagtccctc tctgcgcgct cgctcgctca ctgaggcctg gataccaaag     60

gtatccagac tcctaggctt tgcctaggag gcctcagtga gcgagcgagc gcgcagagag    120

ggagtggcca actccatcac taggggttcc tgcaggagtc aatgggaaaa acccattgga    180

gccaagtaca ctgactcaat agggactttc cattgggttt tgcccagtac ataaggtcaa    240

tagggggtga gtcaacagga aagtcccatt ggagccaagt acattgagtc aatagggact    300

ttccaatggg ttttgcccag tacataaggt caatgggagg taagccaatg ggtttttccc    360

attactgaca tgtatactga gtcattaggg actttccaat gggttttgcc cagtacataa    420

ggtcaatagg ggtgaatcaa caggaaagtc ccattggagc caagtacact gagtcaatag    480

ggactttcca ttgggttttg cccagtacaa aaggtcaata gggggtgagt caatgggttt    540

ttcccattat tggcacatac ataaggtcaa taggggtgac tagtggagaa gagcatgctt    600

gagggctgag tgcccctcag tgggcagaga gcacatggcc cacagtccct gagaagttgg    660

ggggaggggt gggcaattga actggtgcct agagaaggtg gggcttgggt aaactgggaa    720

agtgatgtgg tgtactggct ccaccttttt ccccagggtg ggggagaacc atatataagt    780

gcagtagtct ctgtgaacat tcaagcttct gccttctccc tcctgtgagt ttggtaagtc    840

actgactgtc tatgcctggg aaagggtggg caggagatgg ggcagtgcag gaaaagtggc    900

actatgaacc ctgcagccct aggaatgcat ctagacaatt gtactaacct tcttctcttt    960

cctctcctga caggttggtg tacagtagct tccaccatgg gctctgagct ggagacagct   1020

atggagaccc tgatcaatgt gttccatgcc cactctggca aggagggaga caagtacaag   1080

ctgagcaaga aggagctgaa ggagctgctc cagacagagc tgtctggctt cctggatgcc   1140

cagaaggtga gtgccatgct gtccccagcc cagcatctcc atctcacact cctcctggtt   1200

cactgggtcc tggtaatact ggtccctggg tccctgtccc tattccccaa cagccccctt   1260
```

-continued

```
cagctcctgc atctgcccct gctgcctggc cttcagcagt gttccatgtc cacccattga   1320
ccactgcttg ctggaagtgt ctgagagctc ctggggctga gcagagacac tttcctggtg   1380
ttccaaccct gggggtctcc aacacttgag gcagcagctc agtgatctga gctggttaca   1440
aggacctgga tgcaccaagc caaggacccc cagtggaagg ggagtgctgc caacagagag   1500
gtgcttctcc ccacatacac ccaaggtcct ggtgtgggca caattaggct gagcctcaag   1560
ctcacagtct ttggagtcct atgtgcacta atgagggtct taggtgaaca gacactggca   1620
aggaaatggc ttagaggaca ctgatgctgc ataccatgag cttagacctg ggcccagtcc   1680
ttccttaccc accaccccca gcccctggtc cctagggcct ctttgctacc taagggaaga   1740
acttcagctt cccctggaag gtctcctttg ctgctcctgc caaaccactc ctccctgggc   1800
aagaagcccc tgctgggctg gcttggctag ggtactccca cctcccaata ggagagaggc   1860
tgtattgcct ggtgacagtg gcatggactt tggagccata atgcctgggt tgaatttcta   1920
cctgtgcccc tcactggctg tgtgacattg gcagagttag tccactgttc cttgcctcca   1980
tttccacatg gtaacactac aatatacttc agagggtgat tgtgcagggt tacagagata   2040
atactaattg ttattattgc tatagtgttc caaccactgt tccaagcatg tcccatgtat   2100
taacttacta tgccctcata gcagccctat gggttcatat ctgggaaggt gctcagaaga   2160
gcctggcacc cactaaatgc tcagcatgtc agccattgtt atggcctctc tagtcctgtg   2220
ccttccactt ttttctcttt ttttggttcc acactgaact ctgcaccaag ccaaaggaca   2280
cagatttgcc aaactttggg gcagcacctg ggtggtgcat ggggatgcta ctgctcaaag   2340
ggcacagctt cctgggatgg tgggcagctg ggcatgggtg ccccagaggg gtctggggct   2400
gggctgctag gagggctcca tgacacagcc tccagctttg tgcccagctc tcagaggccc   2460
ttcttatggg actctcatat cctgaaccta ttatggccct gggaccccac agtgggaggc   2520
ccatgaggca tcctggaagg cttctccttg gcttctgcct gtggtacaag gcccctcctg   2580
tcccttaact atcctacccc tcctactctt ccatgctcct ccttctcctc ctgcactgct   2640
gcactcagcc cccttctccc catcccctgg ccacccctga ccatcctccc ttgctctttg   2700
tccttcccct tttcttgcag gatgtggatg ctgtggacaa ggtgatgaag gagctggatg   2760
agaatggaga tggggaggtg gacttccagg agtatgtggt gctggtggct gccctgacag   2820
tggcctgcaa caacttcttc tgggagaaca gctgaagata acagccaggg aggacaagca   2880
gggctgggcc tagggacaga ctgcaagagg ctcctgtccc ctggggtctc tgctgcattt   2940
gtgtcatctt gttgatggag ttgtgatcat cccatctaag ctagcttcct gtcaacactt   3000
ctcacatctt atgctaactg tagataaagt ggtttgatgg tgacttcctc ctctcccacc   3060
ccatgcatta aattttaagg tagaacctca cctgttactg aaagtggttt gaaagtgaat   3120
aaacttcagc accatacaga agacaaatgc ctgcttggtg tgctttcttt cttcttggga   3180
agatggtctg ctagctctag aggatcccct agtgatggag ttggccactc cctctctgcg   3240
cgctcgctcg ctcactgagg cctcctaggc aaagcctagg agtctggata cctttggtat   3300
ccaggcctca gtgagcgagc gagcgcgcag agagggactg gccaagcttg gcgtaatcat   3360
ggtcatagct gtttcctgtg tgaaattgtt atccgctcac aattccacac aacatacgag   3420
ccggaagcat aaagtgtaaa gcctggggtg cctaatgagt gagctaactc acattaattg   3480
cgttgcgctc actgcccgct ttccagtcgg gaaacctgtc gtgccagctg cattaatgaa   3540
tcggccaacg cgcggggaga ggcggtttgc gtattgggcg ctcttccgct tcctcgctca   3600
```

-continued

```
ctgactcgct gcgctcggtc gttcggctgc ggcgagcggt atcagctcac tcaaaggcgg   3660
taatacggtt atccacagaa tcaggggata acgcaggaaa gaacatgtga gcaaaaggcc   3720
agcaaaaggc caggaaccgt aaaaaggccg cgttgctggc gtttttccat aggctccgcc   3780
cccctgacga gcatcacaaa aatcgacgct caagtcagag gtggcgaaac ccgacaggac   3840
tataaagata ccaggcgttt ccccctggaa gctccctcgt gcgctctcct gttccgaccc   3900
tgccgcttac cggatacctg tccgcctttc tcccttcggg aagcgtggcg ctttctcata   3960
gctcacgctg taggtatctc agttcggtgt aggtcgttcg ctccaagctg ggctgtgtgc   4020
acgaaccccc cgttcagccc gaccgctgcg ccttatccgg taactatcgt cttgagtcca   4080
acccggtaag acacgactta tcgccactgg cagcagccac tggtaacagg attagcagag   4140
cgaggtatgt aggcggtgct acagagttct tgaagtggtg gcctaactac ggctacacta   4200
gaagaacagt atttggtatc tgcgctctgc tgaagccagt taccttcgga aaaagagttg   4260
gtagctcttg atccggcaaa caaaccaccg ctggtagcgg tggttttttt gtttgcaagc   4320
agcagattac gcgcagaaaa aaaggatctc aagaagatcc tttgatcttt tctacggggt   4380
ctgacgctca gtggaacgaa aactcacgtt aagggatttt ggtcatgaga ttatcaaaaa   4440
ggatcttcac ctagatcctt ttaaattaaa aatgaagttt taaatcaatc taaagtatat   4500
atgagtaaac ttggtctgac agttaccaat gcttaatcag tgaggcacct atctcagcga   4560
tctgtctatt tcgttcatcc atagttgcct gactccccgt cgtgtagata actacgatac   4620
gggagggctt accatctggc cccagtgctg caatgatacc gcgagaccca cgctcaccgg   4680
ctccagattt atcagcaata aaccagccag ccggaagggc cgagcgcaga agtggtcctg   4740
caactttatc cgcctccatc cagtctatta attgttgccg ggaagctaga gtaagtagtt   4800
cgccagttaa tagtttgcgc aacgttgttg ccattgctac aggcatcgtg gtgtcacgct   4860
cgtcgtttgg tatggcttca ttcagctccg gttcccaacg atcaaggcga gttacatgat   4920
cccccatgtt gtgcaaaaaa gcggttagct ccttcggtcc tccgatcgtt gtcagaagta   4980
agttggccgc agtgttatca ctcatggtta tggcagcact gcataattct cttactgtca   5040
tgccatccgt aagatgcttt tctgtgactg gtgagtactc aaccaagtca ttctgagaat   5100
agtgtatgcg gcgaccgagt tgctcttgcc cggcgtcaat acgggataat accgcgccac   5160
atagcagaac tttaaaagtg ctcatcattg gaaaacgttc ttcggggcga aaactctcaa   5220
ggatcttacc gctgttgaga tccagttcga tgtaacccac tcgtgcaccc aactgatctt   5280
cagcatcttt tactttcacc agcgtttctg ggtgagcaaa aacaggaagg caaaatgccg   5340
caaaaaaggg aataagggcg acacggaaat gttgaatact catactcttc ctttttcaat   5400
attattgaag catttatcag ggttattgtc tcatgagcgg atacatattt gaatgtattt   5460
agaaaaataa acaaataggg gttccgcgca catttccccg aaaagtgcca cctgacgtct   5520
aagaaaccat tattatcatg acattaacct ataaaaatag gcgtatcacg aggccctttc   5580
gtctcgcgcg tttcggtgat gacggtgaaa acctctgaca catgcagctc ccggagacgg   5640
tcacagcttg tctgtaagcg gatgccggga gcagacaagc ccgtcagggc gcgtcagcgg   5700
gtgttggcgg gtgtcggggc tggcttaact atgcggcatc agagcagatt gtactgagag   5760
tgcaccatat gcggtgtgaa ataccgcaca gatgcgtaag gagaaaatac cgcatcaggc   5820
gccattcgcc attcaggctg cgcaactgtt gggaagggcg atcggtgcgg gcctcttcgc   5880
tattacgcca gctggcgaaa gggggatgtg ctgcaaggcg attaagttgg gtaacgccag   5940
ggttttccca gtcacgacgt tgtaaaacga cggccagt                           5978
```

<210> SEQ ID NO 13
<211> LENGTH: 2235
<212> TYPE: DNA
<213> ORGANISM: Artificial sequence
<220> FEATURE:
<223> OTHER INFORMATION: Synthetic sequence (S100A1+intron+ANF)

<400> SEQUENCE: 13
gaattctgta cagtagcttc caccatgggc tctgagctgg agacagctat ggagaccctg 60
atcaatgtgt tccatgccca ctctggcaag gagggagaca agtacaagct gagcaagaag 120
gagctgaagg agctgctcca gacagagctg tctggcttcc tggatgccca gaaggtgagt 180
gccatgctgt ccccagccca gcatctccat ctcacactcc tcctggttca ctgggtcctg 240
gtaatactgg tccctgggtc cctgtcccta ttccccaaca gccccccttca gctcctgcat 300 ctgcccctgc tgcctggcct tcagcagtgt tccatgtcca cccattgacc actgcttgct 360
ggaagtgtct gagagctcct ggggctgagc agagacactt tcctggtgtt ccaaccctgg 420
gggtctccaa cacttgaggc agcagctcag tgatctgagc tggttacaag gacctggatg 480
caccaagcca aggaccccca gtggaagggg agtgctgcca acagagaggt gcttctcccc 540
acatacaccc aaggtcctgg tgtgggcaca attaggctga gcctcaagct cacagtcttt 600
ggagtcctat gtgcactaat gagggtctta ggtgaacaga cactggcaag gaaatggctt 660
agaggacact gatgctgcat accatgagct tagacctggg cccagtcctt ccttacccac 720
cacccccagc ccctggtccc tagggcctct ttgctaccta agggaagaac ttcagcttcc 780
cctggaaggt ctcctttgct gctcctgcca aaccactcct ccctgggcaa gaagcccctg 840
ctgggctggc ttggctaggg tactcccacc tcccaatagg agagaggctg tattgcctgg 900
tgacagtggc atggactttg gagccataat gcctgggttg aatttctacc tgtgcccctc 960
actggctgtg tgacattggc agagttagtc cactgttcct tgcctccatt tccacatggt 1020
aacactacaa tatacttcag agggtgattg tgcagggtta cagagataat actaattgtt 1080
attattgcta tagtgttcca accactgttc caagcatgtc ccatgtatta acttactatg 1140
ccctcatagc agccctatgg gttcatatct gggaaggtgc tcagaagagc ctggcaccca 1200
ctaaatgctc agcatgtcag ccattgttat ggcctctcta gtcctgtgcc ttccactttt 1260
ttctcttttt ttggttccac actgaactct gcaccaagcc aaaggacaca gatttgccaa 1320
actttggggc agcacctggg tggtgcatgg ggatgctact gctcaaaggg cacagcttcc 1380
tgggatggtg ggcagctggg catgggtgcc ccagaggggt ctggggctgg gctgctagga 1440
gggctccatg acacagcctc cagctttgtg cccagctctc agaggccctt cttatgggac 1500
tctcatatcc tgaacctatt atggccctgg gaccccacag tgggaggccc atgaggcatc 1560
ctggaaggct tctccttggc ttctgcctgt ggtacaaggc ccctcctgtc ccttaactat 1620
cctacccctc ctactcttcc atgctcctcc ttctcctcct gcactgctgc actcagcccc 1680
cttctcccca tcccctggcc acccctgacc atcctccctt gctctttgtc cttccccttt 1740
tcttgcagga tgtggatgct gtggacaagg tgatgaagga gctggatgag aatggagatg 1800
gggaggtgga cttccaggag tatgtggtgc tggtggctgc cctgacagtg gcctgcaaca 1860
acttcttctg ggagaacagc tgaagataac agccagggag gacaagcagg gctgggccta 1920
gggacagact gcaagaggct cctgtcccct ggggtctctg ctgcatttgt gtcatcttgt 1980
tgatggagtt gtgatcatcc catctaagct agcttcctgt caacacttct cacatcttat 2040

```
gctaactgta gataaagtgg tttgatggtg acttcctcct ctcccacccc atgcattaaa   2100
ttttaaggta gaacctcacc tgttactgaa agtggtttga aagtgaataa acttcagcac   2160
catacagaag acaaatgcct gcttggtgtg ctttctttct tcttgggaag atggtctgct   2220
agctctagag gatcc                                                    2235
```

<210> SEQ ID NO 14
<211> LENGTH: 1706
<212> TYPE: DNA
<213> ORGANISM: homo sapiens

<400> SEQUENCE: 14

```
gagaaggcca aggagctgtg gcagagcatc tataacttgg aggcagagaa gttcgacctg     60
caggagaagt tcaagcagca gaaatatgag gtgggccgcc atgctgtccc cgcccagcat    120
ctccatctca cactcctcct ggttcactgg gtccggtaat actgctgcag gtccctgggt    180
ccctgtccct attccccaac agccccccttc agctcctgca tctgcccctg ctgcctggcc    240
ttcagcagtg ttccatgtcc accgcattga cgactgcttg ctggaagtgt ctgagagctc    300
gctggggctg agcagagaca ctttcctggt gttccaaccc tgggggtctc caacacgttg    360
aggcagcagc tcagtgatct gagctggtta caaggaccag gatgcaccaa gccaggaccc    420
ccagtggaag gggagtgctg ccaacagaga ggtgcttctc cccacataca cccaaggtcc    480
tggtgtgggc acaattaggc tgagcctcaa gctcacagtc tttcggagtc ctatgtgcac    540
taatgagggt cttaggtgaa cagacaccag gcaaggaaat ggcttagagg acactgatgc    600
tgcataccgg agcttagacc tgggcgccag tccttcctta cccaccaccc ccgagccccg    660
gtcccagggc ctctttgcta cctaagggaa gaattcagct cctccctggg caagaagccc    720
ctcgctgggc aggctcaggc tgcagtggct acagggtact cccacctccc aatacggaga    780
gaggctgtat tgcctggtga cagtggcatg gactttggag ccataatgcc tgggttgaat    840
ttctacctgt gcccctcact ggctgtgtga cattgggtga gttagtccac tgttccttgc    900
ctccatttcc acaggtaaca ctacaatata cttcagaggg tgattgtgag ggttacagag    960
ataatactaa ttgttattat tgctatagtg ttccaaccac tgttccaagc atgtcccatg   1020
tattaactta ctatgccctc atagcagccc tatgggttca tatctgggaa ggtgctcagg   1080
acagagcctg gcacccacta aatgctcagc aggtgtcagc cattgttatg gcctctctag   1140
tcctgtgcct tccacttttt tctctttttt tggttccaca ctgaactctg caccggccaa   1200
caggacacag atttgccaaa ctttggggca gcaccctgca ggggtggtgc atggggatgc   1260
tactgctcaa agggcacagc ttccgggatg gtgggcagct gggcaggggt gccccagagg   1320
ggtctggggc tgggctgcta ggagggctcc atgacacagc ctccagcttt gtgcccagct   1380
ctcagaggcc cttcttatgg gactctcata tcctgaacct attatggccc tgggacccca   1440
cagtgggagg cccatgaggc atcctggaag cttctccttg gcttctgcct gtggtacacg   1500
ggcccctcct gacccttaac tatcctaacc cctcctactc ttccatgctc ctccttctcc   1560
tcctgcactg ctgcactcag ccccccttctc cccatcccca ggccacctgg gacctgagcc   1620
agtcagctcc agcgttgctc tttgtccttc ccacttttct tgcagatcaa tgttctccga   1680
aacaggatca acgataacca gaaagt                                        1706
```